(12) United States Patent
Kram et al.

(10) Patent No.: US 8,911,815 B2
(45) Date of Patent: Dec. 16, 2014

(54) THIN FILM PROCESSING APPARATUSES FOR ADJUSTABLE VOLUME ACCOMMODATION

(75) Inventors: Brian Howard Kram, Tucson, AZ (US); Kevin David Marshall, Tucson, AZ (US); Christine Tse, Tucson, AZ (US); Timothy James Keller, Oro Valley, AZ (US); Austin Micheil Ashby, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 243 days.

(21) Appl. No.: 13/509,785

(22) PCT Filed: Nov. 15, 2010

(86) PCT No.: PCT/US2010/056752
§ 371 (c)(1),
(2), (4) Date: Nov. 12, 2012

(87) PCT Pub. No.: WO2011/060387
PCT Pub. Date: May 19, 2011

(65) Prior Publication Data
US 2013/0052331 A1 Feb. 28, 2013

Related U.S. Application Data

(60) Provisional application No. 61/261,267, filed on Nov. 13, 2009.

(51) Int. Cl.
*A61L 33/00* (2006.01)
*G01N 1/28* (2006.01)
*G01N 1/31* (2006.01)

(52) U.S. Cl.
CPC .............. *G01N 1/2813* (2013.01); *G01N 1/312* (2013.01)
USPC ............................................ 427/2.11; 422/65

(58) Field of Classification Search
USPC ............................................ 427/2.11; 422/65
See application file for complete search history.

(56) References Cited

U.S. PATENT DOCUMENTS

| 3,551,023 A | 12/1970 | Brackett |
| 3,556,633 A | 1/1971 | Mutschmann et al. |

(Continued)

FOREIGN PATENT DOCUMENTS

| EP | 0310399 A2 | 4/1989 |
| EP | 0334534 A2 | 9/1989 |

(Continued)

OTHER PUBLICATIONS

International Searching Authority, International Search Report and Written Opinion, counterpart PCT/US2010/056752, mailed Apr. 29, 2011, 8 pages.

(Continued)

*Primary Examiner* — Dah-Wei D Yuan
*Assistant Examiner* — Andrew Bowman
(74) *Attorney, Agent, or Firm* — Perkins Coie LLP

(57) ABSTRACT

An apparatus can be used to apply and remove fluid substances for processing biological samples. The fluid substances can be delivered between a first substrate and a second substrate. One substrate carries a specimen. A layer of the fluid substance is retained in a gap defined by the first and second substrates. One substrate is moved with respect to the second substrate to disperse the fluid substance in the gap.

22 Claims, 40 Drawing Sheets

(56) References Cited

U.S. PATENT DOCUMENTS

| | | | |
|---|---|---|---|
| 3,672,745 | A | 6/1972 | Speelman |
| 3,961,346 | A | 6/1976 | White |
| 3,972,423 | A | 8/1976 | Tipton |
| 4,023,949 | A | 5/1977 | Schlom et al. |
| 4,107,940 | A | 8/1978 | Schlom et al. |
| 4,146,414 | A | 3/1979 | Stormby |
| 4,156,351 | A | 5/1979 | Schlom et al. |
| 4,203,797 | A | 5/1980 | Stormby |
| 4,359,013 | A | 11/1982 | Prevo |
| 4,392,450 | A | 7/1983 | Prevo |
| 4,418,527 | A | 12/1983 | Schlom et al. |
| 4,428,793 | A | 1/1984 | Sato et al. |
| 4,597,982 | A | 7/1986 | Delameter |
| 4,731,335 | A | 3/1988 | Brigati |
| 4,777,020 | A | 10/1988 | Brigati |
| 4,790,640 | A | 12/1988 | Nason |
| 4,801,431 | A | 1/1989 | Cuomo et al. |
| 4,849,340 | A | 7/1989 | Oberhardt |
| 4,911,782 | A | 3/1990 | Brown |
| 5,002,736 | A | 3/1991 | Babbitt et al. |
| 5,023,187 | A | 6/1991 | Koebler et al. |
| 5,075,079 | A | 12/1991 | Kerr et al. |
| 5,188,963 | A | 2/1993 | Stapleton |
| 5,256,241 | A | 10/1993 | Noever |
| 5,273,905 | A | 12/1993 | Muller et al. |
| 5,503,803 | A | 4/1996 | Brown |
| 5,527,510 | A | 6/1996 | Atwood et al. |
| 5,580,414 | A | 12/1996 | Ljungmann |
| 5,658,723 | A | 8/1997 | Oberhardt |
| 5,681,741 | A | 10/1997 | Atwood et al. |
| 5,812,312 | A | 9/1998 | Lorincz |
| 5,830,028 | A * | 11/1998 | Zovko et al. ............ 446/15 |
| 5,985,669 | A | 11/1999 | Palander |
| 5,989,386 | A | 11/1999 | Elliott |
| 6,037,168 | A | 3/2000 | Brown |
| 6,083,759 | A | 7/2000 | Teshima |
| 6,180,314 | B1 | 1/2001 | Berndt |
| 6,197,494 | B1 | 3/2001 | Oberhardt |
| 6,239,906 | B1 | 5/2001 | Lorincz |
| 6,302,985 | B1 | 10/2001 | Takahashi et al. |
| 6,358,475 | B1 | 3/2002 | Berndt |
| 6,382,693 | B1 | 5/2002 | Ljungmann |
| 6,385,987 | B2 | 5/2002 | Schlom et al. |
| 6,474,386 | B2 | 11/2002 | Takahashi et al. |
| 6,485,918 | B1 | 11/2002 | Schermer et al. |
| 6,486,947 | B2 | 11/2002 | Modlin et al. |
| 6,544,395 | B1 | 4/2003 | Merchant et al. |
| 6,544,793 | B2 | 4/2003 | Berndt |
| 6,544,798 | B1 | 4/2003 | Christensen et al. |
| 6,567,214 | B2 | 5/2003 | Lorincz |
| 6,568,447 | B1 | 5/2003 | Sakai et al. |
| 6,589,650 | B1 | 7/2003 | Govek et al. |
| 6,626,224 | B1 | 9/2003 | Ljungmann |
| 6,717,657 | B2 | 4/2004 | Berndt |
| 6,796,353 | B2 | 9/2004 | Lang et al. |
| 7,063,758 | B2 | 6/2006 | Sakayori et al. |
| 7,186,383 | B2 | 3/2007 | Webster et al. |
| 7,271,006 | B2 | 9/2007 | Reinhardt et al. |
| 7,300,804 | B2 | 11/2007 | Sellek-Prince |
| 7,378,055 | B2 | 5/2008 | Lemme et al. |
| 7,468,160 | B2 | 12/2008 | Thompson et al. |
| 7,468,161 | B2 | 12/2008 | Reinhardt et al. |
| 7,470,541 | B2 | 12/2008 | Copeland et al. |
| 7,615,371 | B2 | 11/2009 | Kram |
| 7,820,381 | B2 | 10/2010 | Lemme et al. |

| Publication Number | | Date | Inventor |
|---|---|---|---|
| 2002/0182115 | A1 | 12/2002 | Aghassi et al. |
| 2003/0087292 | A1 | 5/2003 | Chen et al. |
| 2003/0203493 | A1 | 10/2003 | Lemme et al. |
| 2003/0231987 | A1 | 12/2003 | Carmack et al. |
| 2004/0082058 | A1 | 4/2004 | Schleifer et al. |
| 2004/0092024 | A1 | 5/2004 | Reinhardt et al. |
| 2005/0153453 | A1 | 7/2005 | Copeland et al. |
| 2005/0164374 | A1 | 7/2005 | Kram |
| 2005/0186114 | A1* | 8/2005 | Reinhardt et al. ............ 422/65 |
| 2005/0270642 | A1 | 12/2005 | McLellan et al. |
| 2006/0019302 | A1 | 1/2006 | Lemme et al. |
| 2006/0035369 | A1 | 2/2006 | Gauer et al. |
| 2006/0051253 | A1 | 3/2006 | Gausepohl |
| 2006/0105462 | A1 | 5/2006 | Sellek-Prince |
| 2006/0120921 | A1 | 6/2006 | Elliot et al. |
| 2006/0166371 | A1 | 7/2006 | Testa et al. |
| 2008/0050511 | A1 | 2/2008 | Sellek-Prince |
| 2011/0217731 | A1 | 9/2011 | Burgart et al. |
| 2013/0052331 | A1 | 2/2013 | Kram et al. |

FOREIGN PATENT DOCUMENTS

| | | |
|---|---|---|
| EP | 0502108 A1 | 9/1992 |
| EP | 0334534 B1 | 3/1994 |
| EP | 0611598 A2 | 8/1994 |
| EP | 0310399 B1 | 4/1997 |
| EP | 0801732 A1 | 10/1997 |
| EP | 0611598 B1 | 3/1999 |
| EP | 0502108 B2 | 10/2002 |
| EP | 0801732 B1 | 7/2005 |
| GB | 1562643 A | 3/1980 |
| JP | 0743278 A | 2/1995 |
| JP | 7043278 | 2/1995 |
| JP | 2008507701 A | 3/2008 |
| WO | WO-93/19207 A1 | 9/1993 |
| WO | WO-9319207 A1 | 9/1993 |
| WO | WO-9520176 A1 | 7/1995 |
| WO | WO-96/21142 A1 | 7/1996 |
| WO | WO-9621142 A1 | 7/1996 |
| WO | WO 97/09616 A1 | 3/1997 |
| WO | WO-9709616 A1 | 3/1997 |
| WO | WO-99/34190 A1 | 7/1999 |
| WO | WO-9934190 A1 | 7/1999 |
| WO | WO-2005064309 A1 | 7/2005 |
| WO | WO-2005064309 A1 | 7/2005 |
| WO | WO-2006012498 | 2/2006 |
| WO | WO-2006055096 A2 | 5/2006 |
| WO | WO-2006055096 A2 | 5/2006 |
| WO | WO-2011060387 A1 | 5/2011 |
| WO | WO-2011060387 A1 | 5/2011 |

OTHER PUBLICATIONS

English Translation of Japanese Office Action (related to present application) mailed Oct. 2, 2013, Japanese Patent Office, JP Patent Application No. 2012-539061, International Filing Date: Nov. 15, 2010, Applicant: Ventana Medical Systems, Inc., 3 pages.

English Translation of Japanese Office Action mailed Oct. 2, 2013, Japanese Patent Office, JP Patent Application No. 2012-539061 (related to present application), International Filing Date: Nov. 15, 2010, Applicant: Ventana Medical Systems, Inc., 3 pages.

International Search Report and Written Opinion for Application No. PCT/US2010/056752 (related to present application); Applicant: Ventana Medical Systems, Inc. et al; Date of Mailing: Apr. 29, 2011 (6 pages).

* cited by examiner

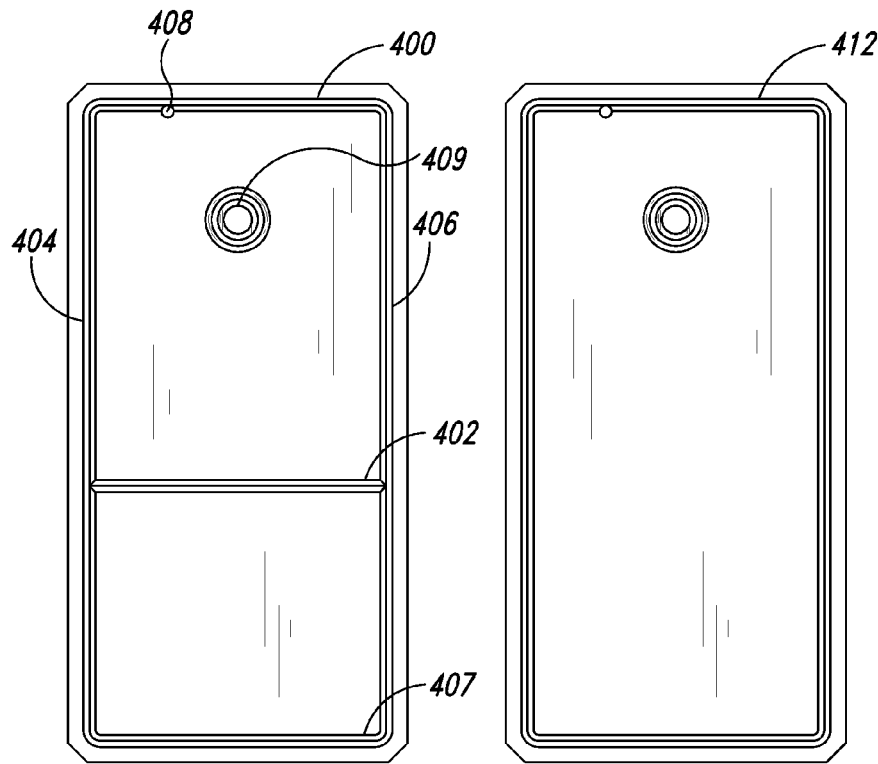
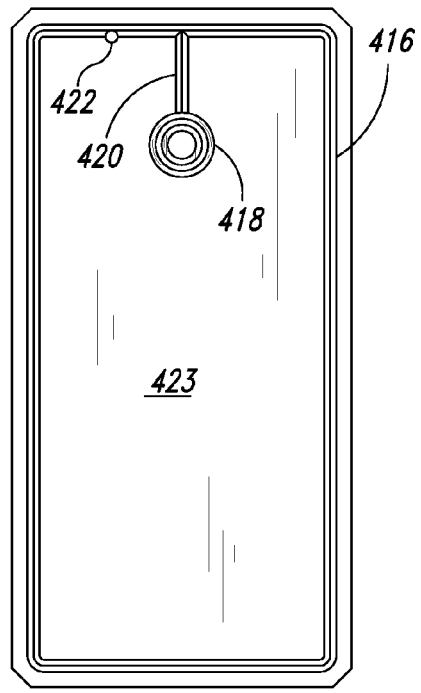
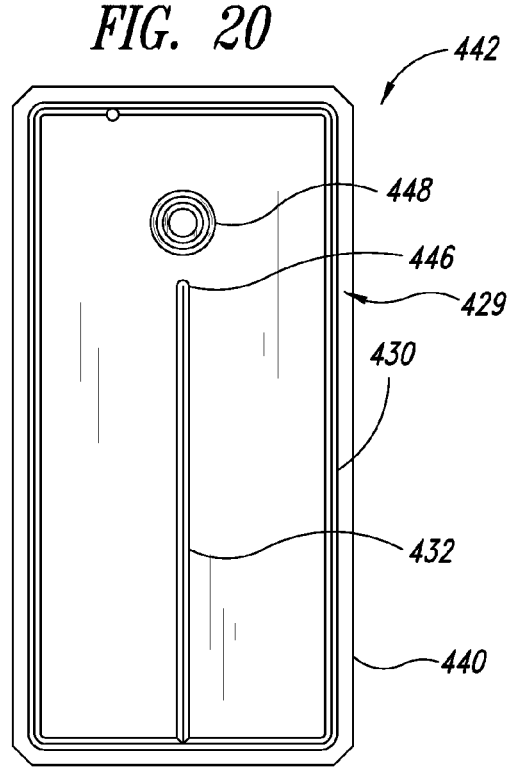
FIG. 19    FIG. 20    FIG. 21    FIG. 22

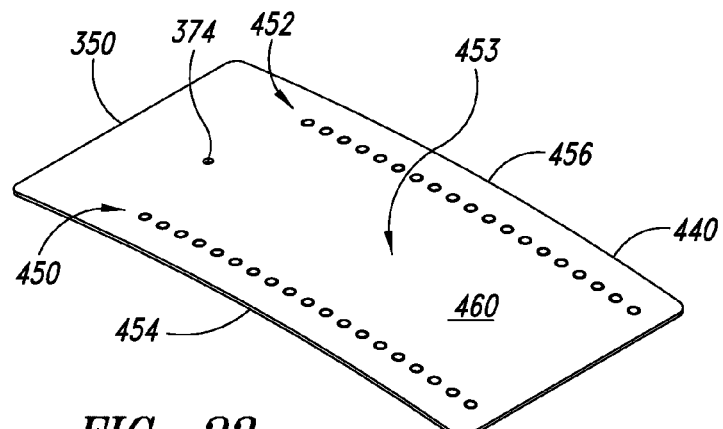
FIG. 23
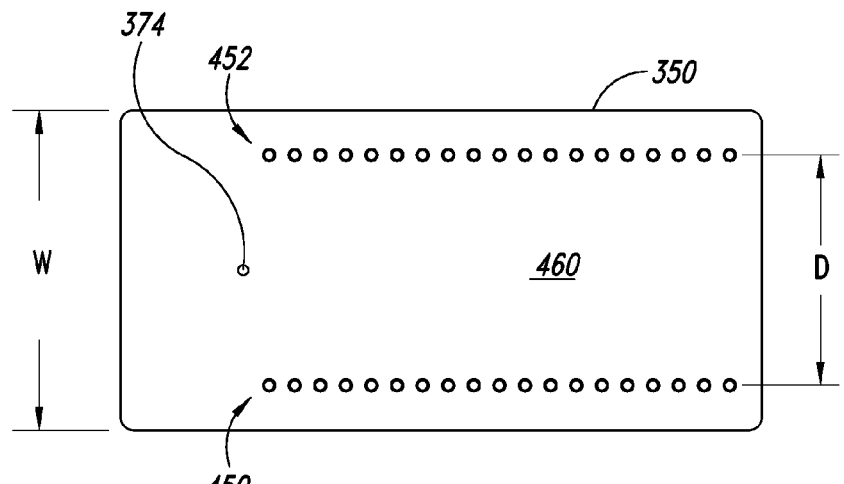
FIG. 24
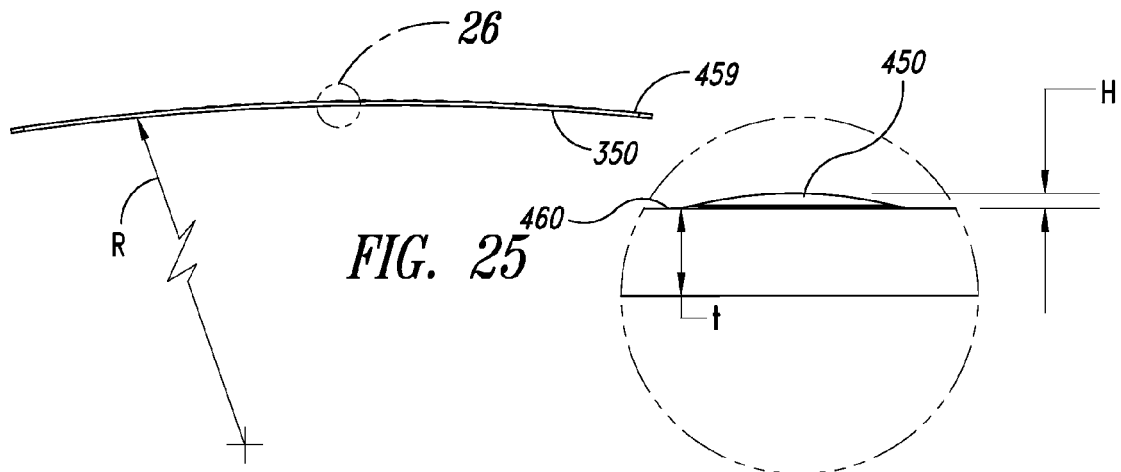
FIG. 25
FIG. 26

THIN FILM PROCESSING APPARATUSES FOR ADJUSTABLE VOLUME ACCOMMODATION

CROSS-REFERENCE TO RELATED APPLICATION

This application is a U.S. National Phase application of PCT/US2010/056752, filed Nov. 15, 2010, entitled "THIN FILM PROCESSING APPARATUSES FOR ADJUSTABLE VOLUME ACCOMMODATION," which claims the benefit under 35 U.S.C. §119(e) of U.S. Provisional Patent Application No. 61/261,267 filed Nov. 13, 2009. All applications listed above are incorporated herein by reference in their entireties.

BACKGROUND

1. Technical Field

The present invention relates generally to methods and apparatuses for processing samples using thin films. More specifically, the invention is related to methods and apparatuses for providing adjustable volume accommodation to process samples.

2. Description of the Related Art

A wide variety of techniques have been developed to prepare and analyze biological samples. Example techniques include microscopy, micro-array analyses (e.g., protein and nucleic acid micro-array analyses), and mass spectrometric methods. Samples are prepared for analysis by applying one or more liquids to the samples. If a sample is treated with multiple liquids, both the application and subsequent removal of each of the liquids can be important for producing samples suitable for analysis.

Microscope slides bearing biological samples, e.g., tissue sections or cells, are often treated with one or more dyes or reagents to add color and contrast to otherwise transparent or invisible cells or cell components. Samples can be prepared for analysis by manually immersing sample-bearing slides in containers of dyes or other reagents. This labor intensive process often results in inconsistent processing and carryover of liquids between containers. Carryover of liquids leads to contamination and degradation of the processing liquids. These types of manual processes often utilize excessive volumes of liquids resulting in relatively high processing costs, especially if the dyes or other reagents are expensive and are prone to degradation due to carryover.

"Dip and dunk" automated machines immerse samples in liquids similar to manual immersing techniques. These automated machines can process samples in batches by submerging racks carrying microscope slides in open baths. Unfortunately, relatively large amounts of reagents are in bath containers of the dip and dunk automated machines. Similar to manual processes, if the liquids are expensive reagents, processing costs may be relatively high, especially if significant amounts of reagents are wasted. Reagent bath containers may be frequently emptied because of contamination due to carryover. Open containers are also prone to evaporative losses that may significantly alter the concentration of the reagents resulting in inconsistent processing. It may be difficult to process samples without producing significant volumes of waste that may require special handling and disposal.

Immunohistochemical and in situ hybridization staining processes are often used to prepare specimens. The rate of immunohistochemical and in situ hybridization staining of sectioned fixed tissue on a microscope slide is limited by the speed at which molecules (e.g., conjugating biomolecules) can diffuse into the fixed tissue from an aqueous solution placed in direct contact with the tissue section. Tissue is often "fixed" immediately after excision by placing it in a 10% solution of formaldehyde, which preserves the tissue from autocatalytic destruction by cross-linking much of the protein via methylene bridges. This cross-linked tissue may present many additional barriers to diffusion, including the lipid bilayer membranes that enclose individual cells and organelles. Conjugate biomolecules (antibody or DNA probe molecules) can be relatively large, ranging in size from a few kilo Daltons to several hundred kiloDaltons, which constrains them to diffuse slowly into solid tissue with typical times for sufficient diffusion being in the range of several minutes to a few hours. Typical incubation conditions are thirty minutes at 37 degrees centigrade.

The diffusion rate is often driven by a concentration gradient so the diffusion rate can be increased by increasing the concentration of the conjugate in the reagent. Unfortunately, conjugates are often very expensive, so increasing their concentration is wasteful and often not economically viable. Additionally, the excessive amount of conjugate that is driven into the tissue, when high concentrations are used, is entrapped in the tissue, and is difficult to rinse out and causes high levels of non-specific background staining. In order to reduce the noise due to non-specific background staining and increase the signal of specific staining, low concentrations of conjugate with long incubation times are often used to allow the conjugate to bind only to the specific sites.

Conventional histology staining instruments often use relatively large volumes of reagent (100 µl) in a puddle of typically 300 µl of buffer. This produces a rather low concentration of the reagent in the puddle that resides over the tissue. Some conventional instruments mix the reagent by alternating tangential air jets onto an overlaying oil layer that rotates and counter-rotates when contacted by the alternating air jets, thereby imparting motion into the underlying aqueous puddle. This mixing is slow and not particularly vigorous and creates significant evaporation losses. Large volumes of rinse liquid are used to physically displace the large puddles of low concentration reagents which are covered with oil. This rinsing procedure produces large volumes of waste liquid which may be hazardous waste, and can physically disrupt the tissue by the vigorous washing action.

BRIEF SUMMARY

At least some embodiments are directed to a method of contacting a sample with a liquid by moving a curved surface wetted with a liquid in proximity to the biological sample. A distance separating the wetted curved surface and the biological sample is sufficient to form a liquid meniscus layer between the curved surface and the slide. The meniscus layer contacts at least a portion of the biological sample.

The meniscus layer can be a relatively thin film that is accommodated in the gap. The substrate is moved to different configurations to accommodate different volumes of fluid forming the meniscus layer. Capillary action for moving the meniscus layer can include, without limitation, movement of the layer due to the phenomenon of the liquid spontaneously creeping through the gap between the curved wetted surface and a slide due to adhesive forces, cohesive forces, and/or surface tension.

In some embodiments, a substrate is moved between a flat configuration, an arcuate configuration (e.g., a simple arc configuration, a complex arc configuration, compound arc configuration, etc.), or angled configuration (e.g., a V-shaped configuration, W-shaped configuration, or the like), as well as any other configuration for accumulating waste and/or treating, incubating, or otherwise treating a sample.

In some embodiments, a station for processing a slide carrying a specimen includes a first platen assembly, a second platen assembly, a drive mechanism configured to move the first platen assembly from a standby position to a processing position, and a slide positioning device. The slide positioning device comprises a slide retaining device. The slide positioning device is operable to position a slide held by the slide retaining device proximate to the first platen assembly in the processing position and operable to position the slide proximate to the second platen assembly when the first platen assembly is in the standby position. The slide positioning device is configured to move the slide along a curved portion of one of the first platen assembly and the second platen assembly to apply a liquid to a sample on the slide.

In other embodiments, a processing system comprises a roller unit, a slide slide retaining device, and an actuator. The roller unit includes a curved portion with a liquid application region. The actuator is coupled to the slide slide retaining device and is configured to move a slide held by the slide slide retaining device along the portion (such as a curved portion) to define a capillary gap. In certain embodiments, the actuator includes one or more driver mechanism, motors, gear systems, piston assemblies, or the like.

In yet other embodiments, a method delivers a slide to a slide slide retaining device. A first liquid is delivered to at least one of the slide and a first curved portion of a roller unit. The slide is moved along the first curved portion to apply the first liquid to a sample between the slide and the roller unit. The curved portion is used to apply different liquids to the sample. In certain embodiments, the curved portion is a disposable used to perform an entire protocol. The roller unit, disposable, and slide can be moved together to any number of different processing stations. In other embodiments, the first curved portion is removed from a holder of the roller unit. A second curved portion is placed on the holder of the roller unit. Additional liquids can be applied to the sample using the second curved portion. The slide is moved along the second curved portion of the roller unit to apply the second liquid to the sample. In certain embodiments, one or both of the curved portions can be in the form of a cover that overlays at least a portion of the roller unit. The cover can include a relatively thin sheet of material.

In some embodiments, an apparatus for applying a liquid to a sample comprises a slide slide retaining device and a deformable applicator movable between a flat configuration and a curved configuration. The deformable applicator in the flat configuration is adapted to extend across a slide held by the slide slide retaining device. The deformable applicator in the curved configuration is adapted to define a varying height capillary gap with the slide held by the slide slide retaining device.

The apparatus can further include a converting device configured to move the deformable applicator between the flat configuration and the curved configuration and a drive mechanism mechanically coupled to the deformable applicator. The drive mechanism includes an actuator for moving the deformable applicator in the curved configuration along the slide.

In yet other embodiments, a cover for processing a sample on a microscope slide includes a body, a first plurality of gapping elements, and a second plurality of gapping elements. The body has a non-planar first surface comprising a reagent application region and a second surface opposing the non-planar first surface. The non-planar first surface and the second surface define a thickness of the body. The reagent application region, in some embodiments, is substantially between the first plurality of gapping elements and the second plurality of gapping elements such that a sample on a microscope slide faces the reagent application region when the microscope slide extends across the first plurality of gapping elements and the second plurality of gapping elements. In certain embodiments, the microscope slide physically contacts and rolls over and along opposing gapping elements.

In some embodiments, a slide processing station includes a base unit and a cover receivable by the base unit. The cover includes an arcuate liquid application region and gapping elements. The gapping elements are positioned outside of the liquid application region and are spaced apart from one another along a length of the liquid application region. The gapping elements are dimensioned to space a slide from the liquid application region to define a gap for containing a liquid.

In other embodiments, an apparatus for processing specimens comprises a drive mechanism movable between a first configuration and a second configuration and a plurality of reagent application stations coupled to the drive mechanism. At least one of the reagent application stations includes a non-planar surface and a slide positioning device. The slide positioning device is configured to carry a slide and is movable between a reagent receiving configuration and a reagent applying configuration. The slide positioning device is moved from the reagent receiving configuration to the reagent applying configuration when the drive mechanism moves from the first configuration to the second configuration.

In some embodiments, a cover comprises one or more disposables or reusable membranes, films, coatings, tiles, or the like. In some embodiments, the cover is a thin membrane that is made of a single material. In other embodiments, the cover is a thin membrane made of multiple materials. For example, the membrane can have a multilayer construction. One of the layers of the membrane can be an adhesive layer for coupling to a platen or other suitable surface.

If the cover is a film or coating, the cover can be discarded after processing a single slide to prevent or limit carryover contamination. In some embodiments, the underlying support surface can include one or more gapping elements (for example, dimples, protrusions, or the like). When the cover overlies the surface, the gapping elements can form corresponding discontinuities along the cover. In some embodiments, a roll includes a dispensable material, such as a sheet, that is controllably dispensed to move the sheet across a microscope slide. The portion of the sheet on the slide forms a cover. Different sections of the sheet can be used to apply different processing fluids.

In other embodiments, a station for processing a slide carrying at least one sample includes a platen assembly and a slide retaining device. The slide retaining device is configured to move the slide along a curved portion of the platen assembly to apply a liquid to a sample on the slide when the liquid is between the platen assembly and the slide.

In some embodiments, a method of mixing fluids includes dispensing a first fluid onto a slide. After dispensing the first fluid, a second fluid is dispensed onto the slide. A substrate opposing the slide is used to mix the first and second fluids to produce a mixed fluid. A desired level of homogeneity of the mixture can be achieved due to the mixing action. In certain embodiments, the first fluid is mixed before dispensing the second fluid.

In some embodiments, a staining apparatus has a rolling mode so that a slide uses a disposable to apply one or more liquids to a specimen. The disposable can be used to apply the liquids, during incubation, and/or removal of the liquids.

A staining apparatus, in some embodiments, includes a swappable unit that uses two disposables to process a single slide. The swappable unit can apply liquids, perform incubation, and/or remove liquids to perform a desired protocol. In other embodiments, additional disposables can be utilized to perform complex staining. As used herein, the term "disposable" when applied to a system or component (or combination of components), such as a cover, a substrate, a processing liquid, or the like, is a broad term and generally means, without limitation, that the system or component in question is used a finite number of times and is then discarded. Some disposable components, such as a plastic tile, are used only once and are then discarded. In some embodiments, multiple components of a processing apparatus are disposable to further prevent or limit carryover contamination. In other embodiments, the components are non-disposable and can be used any number of times. For example, covers are non-disposable and may be subjected to different types of cleaning and/or sterilization processes without appreciably altering the characteristics of the cover.

In some embodiments, a station for processing a slide carrying a specimen includes a first platen assembly, a second platen assembly, and a drive mechanism configured to move the first platen assembly from a standby position to a processing position. A slide positioning device comprises a slide retaining device and is operable to position a slide held by the slide retaining device proximate to the first platen assembly in the processing position and operable to position the slide proximate to the second platen assembly when the first platen assembly is in the standby position. The slide positioning device is configured to move the slide along a curved portion of one of the first platen assembly and the second platen assembly to apply a liquid to a sample on the slide when the liquid is between the one of the first platen assembly and the second platen assembly and the slide.

The drive mechanism, in some embodiments, may alternatingly position the first platen assembly at the standby position and at the processing position. The second platen assembly has a substantially flat surface. The slide positioning device is movable between a first configuration to lay the slide across the substantially flat surface and a second configuration to keep the slide spaced apart from the substantially flat face. The first platen assembly includes a holder and a cover removably coupleable to the holder. The holder includes at least one thermal element configured to receive electrical energy and to generate heat using the electrical energy.

The station may further include a rail apparatus retaining the first platen assembly. The first platen assembly is slidable along the rail apparatus between the standby position and the processing position. The slide positioning device has a rolling mode to move the slide with respell to the curved portion to define a variable height gap between the slide and the curved portion and a non-rolling mode to lay the slide on the other one of the first platen assembly and the second platen assembly. In the rolling mode, the slide can be rotated longitudinally and/or laterally with respect to the curved portion.

A sample processing system, in some embodiments, includes a roller unit, a slide retaining device, and an actuator. The roller unit has a curved portion that includes a liquid application region. The actuator is coupled to the slide retaining device. The actuator is configured to move a slide held by the slide retaining device along the curved portion to define a capillary gap between the slide and the curved portion such that the capillary gap has a varying height.

The roller unit includes a first plurality of discrete gapping elements and a second plurality of discrete gapping elements spaced apart from the first plurality of discrete gapping elements. At least a portion of the liquid application region is between the first plurality of discrete gapping elements and the second plurality of discrete gapping elements. The first plurality of discrete gapping elements may include at least one dimple having a height of at least 0.001 inch.

The roller unit may include an arcuate cover and a holder with a mounting region for receiving the cover. The curved portion includes the arcuate cover. The arcuate cover can be compliant, semi-compliant, or rigid.

The sample processing system may further include a fluid dispenser having a port positioned to deliver liquid between an end of the slide held by the slide gripper device and the curved portion. The roller unit may include a waste port positioned to remove liquid from the capillary gap. The actuator may be coupled to the slide retaining device such that the slide retaining device moves the slide along the external curved portion so as to move a liquid in the capillary gap towards a waste port of the roller unit using capillary action.

A method may include delivering a slide to a slide retaining device. A first liquid is delivered to at least one of the slide and a curved portion of a roller unit. The slide held by the slide gripper device is moved along the curved portion of the roller unit to apply the first liquid to a sample between the slide and the roller unit. A second liquid is applied to at least one of the slide and the curved portion of the roller unit. The slide held is moved by the slide gripper device along the curved portion of the roller unit to apply the second liquid to the sample between the slide and the roller unit.

The method includes moving the first liquid towards a waste port of the roller unit by rolling the slide. The first liquid is removed from a gap between the slide and the curved portion using the waste port while the slide overlies the waste port. The slide held by the slide retaining device and moved along the curved portion. In some embodiment, the slide is rolled the slide along a first plurality of gapping elements and a second plurality of gapping elements spaced apart from the first plurality of gapping elements. The method may further include removing the first liquid from between the slide and the curved portion removing the curved portion from a holder of the roller unit. Another curved portion is placed on the holder of the roller unit.

In some embodiments, a station for processing a slide carrying a specimen includes a platen assembly having a curved portion and a slide retaining device. The slide retaining device is configured to move the slide along the curved portion of the platen assembly to apply a liquid to a sample on the slide when the liquid is between the platen assembly and the slide. In some embodiments, the station may further include a slide positioning device having the slide retaining device. The slide positioning device has a rolling mode to move the slide with respect to the curved portion to define a variable height gap between the slide and the curved portion and a non-rolling mode to lay the slide on the curved portion.

In yet other embodiments, an apparatus for applying a liquid to a sample may include a slide retaining device and a deformable applicator movable between a flat configuration and a curved configuration. The deformable applicator in the flat configuration is configured to extend across a slide held by the slide gripper device. The deformable applicator in the curved configuration is configured to define a variable height capillary gap with the slide held by the slide gripper device. A converting device is configured to move the deformable applicator between the flat configuration and the curved configuration; and a drive mechanism mechanically coupled to the deformable applicator. The drive mechanism includes an actuator operable to move the deformable applicator in the curved configuration along the slide held by the slide gripper device.

The deformable applicator may include a holder and a cover configured to mate with the holder. The cover includes a plurality of gapping elements positioned to face the slide held by the slide gripper device. The deformable applicator is movable between an open position and a closed position. The deformable applicator moves away from the slide gripper device as the deformable applicator moves from the closed position towards the open position.

In yet other embodiments, a cover for processing a sample on a microscope slide includes a body having a non-planar first surface comprising a reagent application region and a second surface opposing the non-planar first surface. The non-planar first surface and the second surface define a thickness of the body. In certain embodiments, the cover includes a first plurality of gapping elements and a second plurality of gapping elements. The reagent application region is substantially between the first plurality of gapping elements and the second plurality of gapping elements such that a sample on a microscope slide faces the reagent application region when the microscope slide extends across the first plurality of gapping elements and the second plurality of gapping elements.

The first plurality of gapping elements may extend along a first longitudinal side of the body and the second plurality of gapping elements may extend along a second longitudinal side of the body. The second longitudinal side opposes the first longitudinal side. The thickness of the body may be greater than a height of at least one of the first plurality of gapping elements. The first plurality of gapping elements may include linearly arranged dimples that are spaced apart from one another. The first plurality of gapping elements and the second plurality of gapping elements may be dimensioned to define a capillary gap between the microscope slide and the body when the microscope slide physically contacts at least one of the first plurality of gapping elements and at least one of the second plurality of gapping elements. The body may have a radius of curvature in a range of about 5 inches to about 40 inches.

In some embodiments, a slide processing station may include a base unit and a cover receivable by the base unit. The cover includes an arcuate liquid application region. A plurality of discrete gapping elements can be positioned outside of the liquid application region and spaced apart from one another along a length of the liquid application region. The plurality of discrete gapping elements can be dimensioned to space a slide from the liquid application region to define a gap for containing a liquid between the slide and the liquid application region.

The slide processing station may further include a fluid dispenser including an outlet port positioned to deliver liquid between the slide and the cover to at least partially fill the gap. The base unit may include a waste passage. The cover may include a waste port that mates with the waste passage to define a fluid path through the cover and the base unit. In one embodiment, the cover includes a first surface and an opposing second surface. The first surface includes the liquid application region and the waste port is a throughhole extending between the first surface and the second surface. In one embodiment, the base unit includes a slide retaining device and an actuator. The slide retaining device is configured to hold a slide. The actuator is movable between a first position and a second position to move a sample on the slide along a length of the liquid application region while the sample is located in the gap. The slide processing station may further include a pressurization device fluidically coupled to a waste port in the cover. The pressurization device is adapted to apply a vacuum to remove liquid from the gap via the waste port and may include at least one pump. The cover may include a polymer sheet. The base unit may include a vacuum chuck for holding the polymer sheet.

In still further embodiments, an apparatus for processing specimens includes a drive mechanism movable between a first configuration and a second configuration, a plurality of reagent application stations coupled to the drive mechanism, and a slide positioning device configured to carry a slide. One of more of the reagent application stations includes a non-planar surface. The slide positioning device is movable between a reagent receiving configuration and a reagent applying configuration when the drive mechanism moves from the first configuration to the second configuration.

At least one of the reagent application stations includes a dispensing unit having an outlet port positioned to dispense a reagent onto at least one of the non-planar surface and the slide held by the slide positioning device. The slide positioning device may be positioned to define a variable height capillary gap between the slide held by the slide positioning device and the non-planar surface. At least one of the reagent application stations includes a convertible device having a rolling mode and a non-rolling mode. The non-planar surface is movable to a substantially planar configuration when the convertible device is in the non-rolling mode.

At least some embodiments of mixing fluids may includes dispensing a first fluid onto a slide, dispensing a second fluid onto the slide after dispensing the first fluid, and mixing the first fluid and the second fluid using a substrate that opposes the slide to produce a mixed fluid. The first fluid and second fluid can be at different temperatures when delivered onto the slide.

In some embodiments, an automated slide processing station comprises a first platen assembly, a second platen assembly, and a drive mechanism. The first platen assembly has a curved portion. The drive mechanism is configured to move the first platen assembly from a standby position to a processing position. A liquid dispensing assembly is configured to dispense a liquid. The second platen assembly includes a slide positioning device. The slide positioning device includes a slide retaining device. The slide positioning device is operable to position a slide retained by the slide retaining device proximate to the first platen assembly. The first platen assembly and second platen assembly are configured to cause a longitudinal or transverse rolling movement of the curved portion of the first platen assembly relative to the second platen assembly retained slide to create a varying height gap between the slide and the curved portion sufficient to apply a liquid to a sample on the slide.

The first platen assembly, in some embodiments, includes a holder and a cover removably coupled to the holder. The cover has a relatively compliant specimen facing surface for contacting the liquid in the varying height gap. The holder is relatively rigid. For example, the holder can be more rigid than the cover. The cover can be made of a compliant plastic or elastomer, and the holder can be made of metal or a hard plastic. In other embodiments, the first platen assembly includes a specimen facing surface that comprises a semi-compliant material that is more compliant than the slide. For example, the material forming the specimen facing surface can be more compliant than glass.

In some embodiments, a method comprises delivering a slide carrying a sample to a slide positioning device of an automated slide processing station. A liquid is delivered to at least one of the slide and a curved portion of a roller unit of the automated slide processing station. The curved portion of the roller unit is moved (e.g., rolled) relative to the slide held by the slide positioning device to apply the liquid to the sample on the slide. In certain embodiments, the liquid is applied while it is located in a varying height gap defined by the slide and the curved portion.

BRIEF DESCRIPTION OF THE SEVERAL VIEWS OF THE DRAWINGS

Non-limiting and non-exhaustive embodiments are described with reference to the following drawings. The same reference numerals refer to like parts or acts throughout the various views, unless otherwise specified.

FIGS. 19-22 are top plan views of holders with different channel configurations.

FIG. 23 is an isometric view of a cover, in accordance with one embodiment.

FIG. 24 is a top plan view of the cover of FIG. 23.

FIG. 25 is a side elevational view of the cover of FIG. 23.

FIG. 26 is a detailed view of a gapping element.

DETAILED DESCRIPTION

Figure 1:
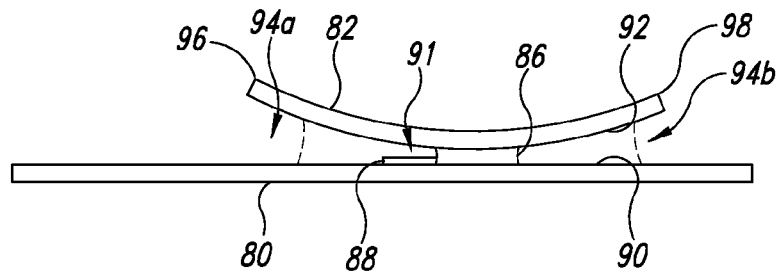
FIGS. 1-4 are side elevational views of a pair of substrates processing a sample, in accordance with one embodiment.

FIG. 1 shows a first substrate 80, a second substrate 82, and a substance 86 between the first and second substrates 80, 82. The first and second substrates 80, 82 can be moved with respect to one another to manage the substance 86, such as processing liquid. Managing the substance 86 may include agitating the substance 86, spreading the substance 86 along an upper surface 90 of the first substrate 80, moving the substance 86, or otherwise manipulating the substance 86 to process a biological sample 88 on the upper surface 90.

Protocols can be performed using optimized liquid volumes to minimize or avoid problems with excessive volume consumption, including high processing costs and waste management. In some embodiments, a gap 91 can have a varying height, e.g., a height that varies along the length and/or width of the gap, formed by the first and second substrates 80, 82 for enabling variable volume processing. In variable volume processing, optimized volumes of liquids can be used for processing to increase efficiency and reduce waste volumes and cost as compared to fixed volume processing (i.e., processing that only uses a constant volume of liquid for each liquid application). The reductions may be based on the reduction of the consumed liquid volumes, as well as the reduction of system costs by reducing or avoiding relatively high costs associated with higher liquid volume consumption, including manufacturing costs, packaging costs, transportation costs, customer workflow handling costs (e.g., handling cost for incoming inventory as well as outgoing waste management), and fluidic management overhead costs. Excessive liquid volumes may also lead to excessive waste volumes or malfunctions (e.g., clogging, leaking, or the like) of fluidic components and may require frequent recalibration of equipment. The substrates 80, 82 can be used to efficiently process the sample 88 while avoiding or limiting at least some of the problems associated with larger liquid volumes.

The gap 91 can accommodate a wide range of liquid volumes, even without moving the substrates 80, 82. In some embodiments, the gap 91 can accommodate liquid volumes greater than about 10 microliters. In some embodiments, the gap 91 can accommodate liquid volume in a range of about 10 microliters to about 200 microliters. The height profile of the gap 91 can be varied based on the liquid volume or properties to be utilized. To treat the sample 88 with a large volume of liquid, the size of the gap 91 can be increased to avoid over-filling. In some embodiments, over-filling occurs when the volume of dispensed liquid is greater than the volume of the gap 91 (e.g., the volume between the first and second substrates 80, 82). Over-filling can lead to unwanted conditions, including sagging of liquid and/or fluid draining, especially if the substrates 80, 82 are at an upright orientation. If smaller or lesser liquid volumes are to be dispensed, the size of the gap 91 can be decreased to avoid under-filling. Under-filling may lead to inadequate contact between the liquid 86 and the sample 88 and occlusions. FIG. 1 shows ends 94a, 94b (collectively "94") of the gap 91 that can be filled with the liquid 86 by reducing the gap height, by changing the gap height profile, and/or by adding liquid to the gap 91. Advantageously, a significant volume of liquid can be conveniently added without over-filling. By preventing over-filling and under-filling, different types of fluidic failure modes (e.g., reagent performance degradation), reagent waste, or the like can be avoided or limited.

Processing protocols may require different liquid volumes in order to meet various processing criteria (e.g., chemical requirements, uptake requirements, solubility limitations, viscosity or the like). If the sample 88 is a paraffin embedded specimen, a relatively small volume of de-waxing solution (e.g., 12 microliters of xylene) can be delivered into the gap 91. The substrate 82 is used to apply the liquid to the sample 88. For example, the substrate 82 can be rolled (e.g., rolled along an imaginary plane spaced apart from the upper surface 90, rolled along the upper surface 90, rolled sideways, rolled longitudinally, or the like) or otherwise manipulated (e.g., rotated, translated, or both) to apply the liquid 86. A specimen facing surface 92 of the substrate 82 can be used to manipulate the volume of reagent. After dewaxing, a relatively large volume of reagent can be delivered into the gap 91. For example, a volume of about 80 microliters to about 120 microliters of stain can be delivered into the gap 91. The stain is delivered to the sample 88 and then subsequently removed. The substrates 88, 82 can thus cooperate to hold different amounts of fluid for rinsing, staining, incubating, or the like.

The gap 91 of FIG. 1 can have a minimum holding capacity of about 5 microliters (shown in solid line in FIG. 1) and a maximum holding capacity of about at least 5 microliters, 50 microliters, 100 microliters, or 200 microliters (shown in dashed line in FIG. 1). Other minimum and maximum holding capacities are possible, if needed or desired. The minimum holding capacity is the smallest volume of liquid that can be contained in the gap 91 and effectively applied to the sample 88. The maximum holding capacity is the largest volume of liquid that can be contained in the gap 91 without over-filling. The varying height gap 91 can accommodate a wider range of liquid volumes than a uniform height gap because the narrowed region of the gap 91 can accommodate a small liquid volume, while the widened gap end 94 can accommodate a large liquid volume. The widened gap end 94 can also provide convenient access to deliver liquid to the gap 91.

The second substrate 82 can move the liquid 86 via capillary action. When the height of the gap 91 is sufficiently small, the gap 91 is a capillary gap that can be maintained regardless of the presence or absence of liquid. A low viscosity liquid, such as water, can be retained by capillary action in the gap 91. High viscosity substances can also be retained in the gap 91 if desired. One portion of the capillary gap 91 can be narrower and have greater capillarity than a different portion of the capillary gap 91. A thin film of the liquid 86 may tend to flow to the narrowed portion of the gap 91. The separation between the substrates 80, 82 at any given location on surfaces 90, 92 may vary over time.

FIG. 1 shows the entire substrate 82 spaced apart from the substrate 80. If the substrate 82 physically contacts the upper surface 90, the liquid 86 may tend to flow along the contact interface. Even though the entire substrate 82 is spaced apart from the substrate 80, the substrates 80, 82 can effectively enchamber the liquid 86.

In a one embodiment, gapping elements can be outwardly protruding dimples positioned on the substrate 82. Gapping elements can also include, without limitation, one or more positioners, rails, spacers, or other structural features capable of serving as spacers. In some embodiments, the substrate 82 includes one or more rails (e.g., straight rails, arcuate rails, or the like) configured to bear against the upper surface 90. In yet other embodiments, gapping elements may be separate components positionable between the substrates 80, 82, or at any other suitable location. Gapping elements may also be adjustable in their dimensions, position or orientation to adjust the gap between the substrates 80, 82.

Figure 2:
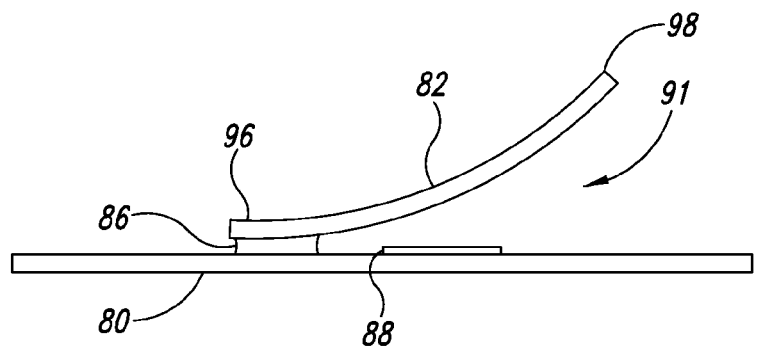
Figure 3:
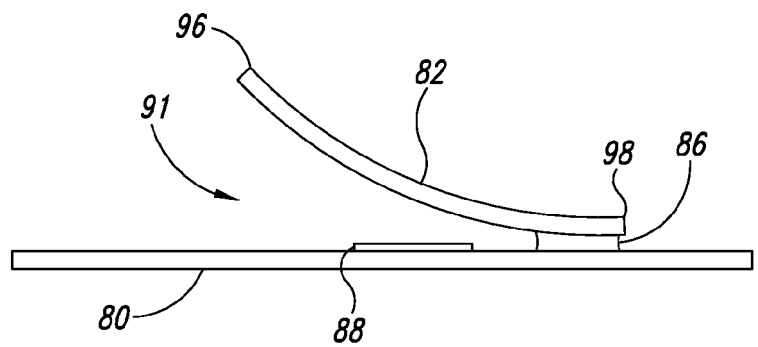

To move the liquid 86 across the upper surface 90, a first end 96 of the substrate 82 in FIG. 1 can be moved towards the substrate 80 until the liquid 86 is in the position shown in FIG. 2. The liquid 86 can also be moved to an opposing second end 98 of the substrate 82 by narrowing the portion of the gap 91 formed by the second end 98, as shown in FIG. 3. In this manner, the ends 96, 98 can be alternately lowered and raised to move the liquid 86 via, for example, capillary action or any type of motile force. Alternatively, the substrate 80 can be moved relative to the stationary substrate 82 to similarly move the liquid 86.

Figure 4:
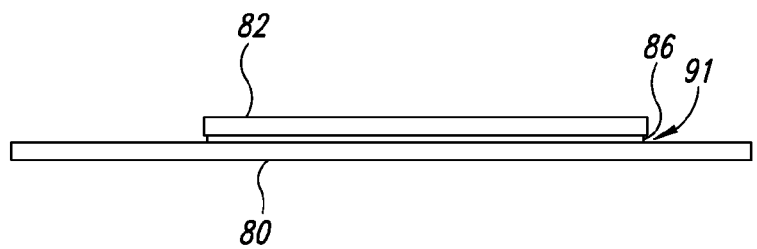

FIG. 4 shows the gap 91 having an approximately uniform height such that the liquid 86 fills a substantial volume of the gap 91. The volume of the gap 91 is the volume directly between the first and second substrates 80, 82. The range of holding capacities of the gap 91 of FIG. 4 is narrower than the range of holding capacities of the varying height gap 91 in FIG. 1. For example, the gap 91 of FIG. 4 can have a nominal gap height of about 0.008 cm, a width of about 2.5 cm, and a length of about 5 cm to effectively accommodate: 0.008 cm×2.5 cm×5 cm=0.1 cm$^3$=100 microliter of volume liquid. An excess or deficiency of about 1-10 microliters may result in over-filling or under-filling. The difference between the minimum holding capacity and the maximum holding capacity of the varying height gap 91 of FIG. 1 can be at least about 25 microliters, 50 microliters, 100 microliters, or 150 microliters, or ranges encompassing such liquid volumes.

The substrate 82 in the curved configuration (see FIG. 1) can expose a relatively large surface area of the liquid 86 to the surrounding environment. To reduce evaporative losses, the radius of curvature of the substrate 82 may be increased to reduce the exposed surface area of the liquid 86. The substrate 82 in FIG. 4 is especially well suited to minimize or substantially eliminate significant evaporative losses and/or sample losses. By controlling evaporative and sample losses, the substrates 80, 82 can be used to perform different types of incubating procedures, as well as other low evaporation procedures As used herein, the term "substrate" is a broad term and includes, but is not limited to, a cover, a slide, a coverslip, a strip of material, a plate, a membrane, a film (e.g., a coating), a tile, a carrier capable of carrying one or more samples, or the like. Substrates can be substantially rigid, semi-compliant, and/or compliant. In some embodiments, the substrate 80 is a microscope slide. A substrate can also be part of another component. For example, a platen or holder can have an outer surface that forms a substrate. The dimensions, properties (including mechanical properties, chemical properties, surface properties, and/or optical properties), and configurations of the substrates can be selected based on the processing protocol and subsequent analyses to be performed.

In some embodiments, a substrate can be a flat or substantially flat substrate. "Substantially flat substrate" refers, without limitation, to any object having at least one substantially flat surface, but more typically to any object having two substantially flat surfaces on opposite sides of the object, and even more typically to any object having opposed substantially flat surfaces, which opposed surfaces are generally equal in size but larger than any other surfaces on the object. A substantially flat substrate can comprise any suitable material, including plastics, rubber, ceramics, glass, silicon, semiconductor materials, metals, combinations thereof, or the like. Non-limiting examples of substantially flat substrates include flat covers, slides (both 1 inch×3 inch microscope slides and 25 mm×75 mm microscope slides), SELDI and MALDI chips, silicon wafers, or other generally planar objects with at least one substantially flat surface.

The substrate 82 may be semi-compliant, compliant, or rigid in order to assume or maintain a wide range of configurations. FIGS. 1-3 show the substrate 82 in a simple arc configuration. Simple arcs include arcs having generally uniform curvatures. The radius of curvature of the simple arcs can be about 0.5 inch, 1 inch, 5 inches, 20 inches, 25 inches, 30 inches, 35 inches, 40 inches, 45 inches, or ranges encompassing such radii of curvature. Other radii are also possible. In some embodiments, the radius of curvature is in a range of about 5 inches to about 40 inches. Such a substrate may be well suited to apply a liquid using a rolling and/or rocking motion while effectively managing evaporative losses, if any, and controlling movement of the fluid. In other embodiments, the substrate 82 can assume a complex arc configuration or a compound arc configuration. If the substrate 82 is in a complex arc configuration, at least a portion of the substrate 82 may have a varying curvature. If the substrate 82 is in a compound arc configuration, a portion of the substrate 82 can be a simple arc and another portion of the substrate 82 can be a complex arc.

Figure 5:
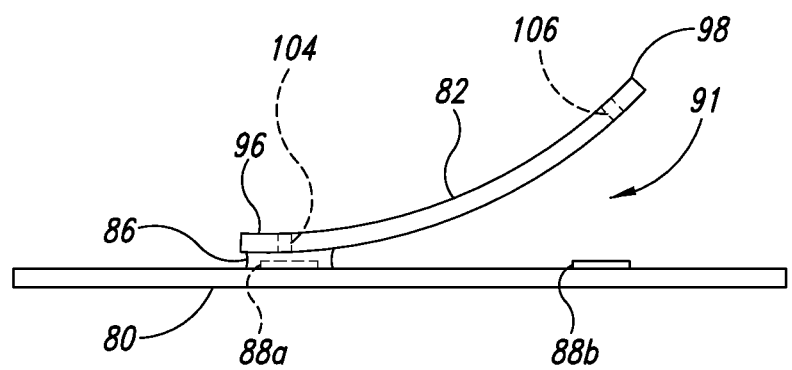
FIGS. 5 and 6 are side elevational views of a pair of substrates processing two samples, in accordance with one embodiment.
Figure 6:
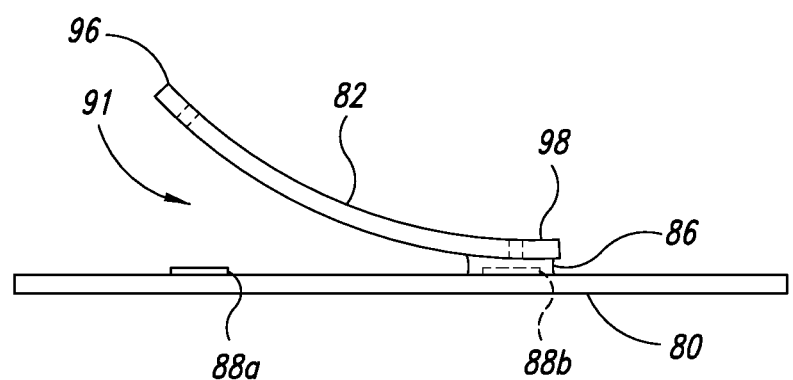

Multiple related specimens can be treated on upper surface 90 using a single substrate. The specimens can be concurrently or sequentially treated with the same fluid. FIG. 5 shows the liquid 86 treating a sample 88*a* (illustrated in dashed line). The liquid 86 is then moved to another sample 88*b*. FIG. 6 shows the liquid 86 treating the sample 88*b* (illustrated in dashed line). In this manner, the liquid 86 can be moved along the substrate 80 to any number of related specimens.

In some protocols, both related specimens 88*a*, 88*b* can be rinsed with an appropriate solution, such as a non-volatile transfer fluid or other fluid, suitable for avoiding drying out. After stabilizing the specimens 88*a*, 88*b*, the substrate 82 can form a narrowed section of the gap 91 proximate the sample 88*a*. A reagent (e.g., a stain) can be delivered to the gap 91. The substrate 82 can be moved to translate a layer of the liquid 86 between the specimens 88*a*, 88*b*. The liquid 86 used to process the sample 88*a* can be removed via a waste port 104 (illustrated in dashed line). A waste port 106 (illustrated in dashed line) can be used to remove liquid used to process the sample 88*b*. In this manner, the substrate 82 can be used to individually treat the specimens 88*a*, 88*b* at opposing ends of the substrate 80, as well any other specimens at any other suitable locations along the substrate 80.

Figure 7:
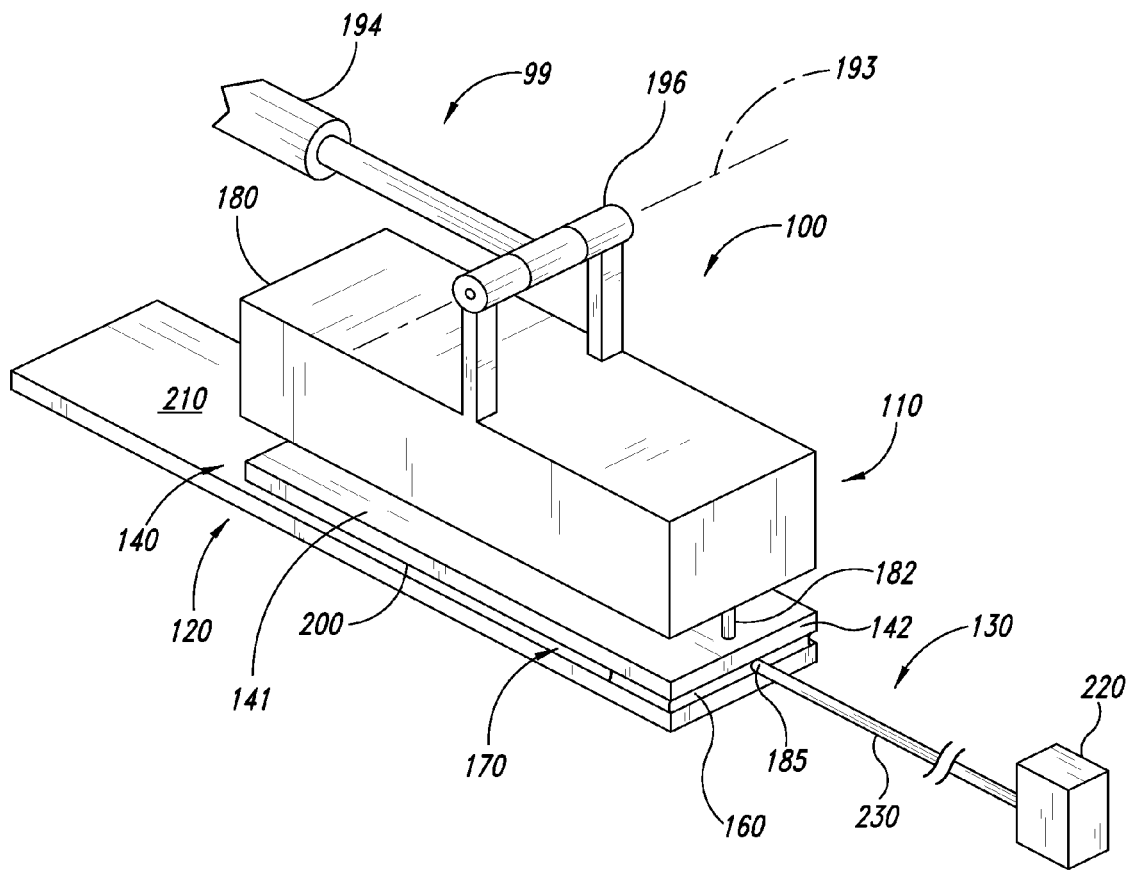
FIG. 7 is an isometric view of a slide processing apparatus capable of applying fluids to a sample carried on a slide, in accordance with one embodiment.

FIG. 7 shows a slide processing apparatus 100 including a positioning mechanism 99, a base unit 110, and a waste remover 130. The base unit 110 carries an opposable substrate 140 used to apply a processing liquid to one or more specimens carried by a microscope slide 120. The liquid can equilibrate and remain in a static condition for a desired length of time, even for long periods of time. The substrate 140 can be used to agitate the processing liquid, spread the processing liquid, control evaporation, or otherwise manage the processing liquid. The illustrated base unit 110 engages a back face 141 of the substrate 140. A front face 200 (see FIG. 8) is a specimen facing surface. A thin film 160 of processing fluid can treat a biological sample 187.

The positioning mechanism 99 includes an actuator 194 and a pivot mechanism 196. The pivot mechanism 196 defines an axis of rotation 193 about which the substrate 140 rotates. To roll the substrate 140 from the position shown in FIG. 8 to the position shown in FIG. 9, the actuator 194 can extend and the pivot mechanism 196 can rotate.

The processing liquid 160 can be efficiently applied to the sample 187 to minimize or limit the cost of processing liquid(s) and to minimize or limit the amount of waste liquid produced. The substrate 140 can be manipulated (e.g., translated, rotated, vibrated, or combinations thereof) to move the liquid 160. To agitate the liquid 160, the substrate 140 can be rolled along slide 120. For example, the substrate 140 in a curved configuration can rotate due to physical contact with the slide 120. In other embodiments, the substrate 140 can slide along the slide 120.

Figure 8:
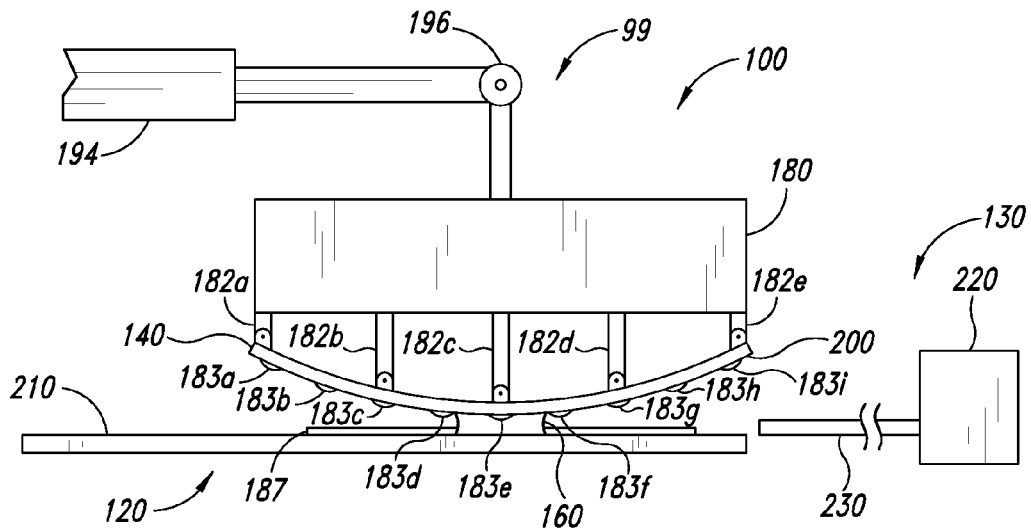
FIGS. 8-13 are side elevational views of the slide processing apparatus of FIG. 7 processing a specimen.
Figure 9:
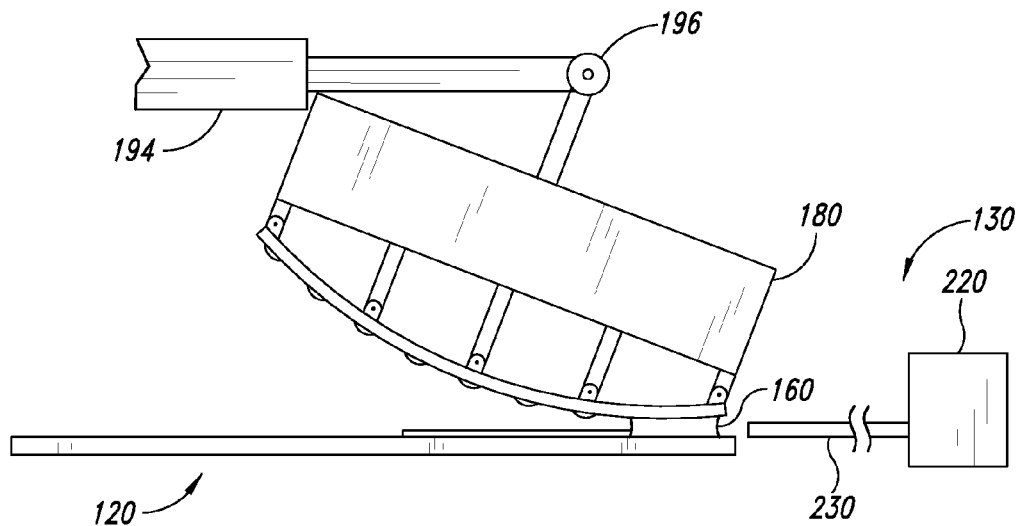

The liquid 160 can be moved along the slide 120 due to different forces, such as gravity, capillary forces, and/or a pressure change (e.g., a reduced pressure such as a vacuum) in a gap 170. The substrate 140 in FIG. 8 is well suited to move the liquid 160 across the sample 187 by, for example, rolling back and forth across the sample 187. The substrate 140 can assume a generally flat configuration to form a thin film across the sample 187 to, for example, incubate the sample 187.

The slide processing apparatus 100 can perform different tissue preparation processes and mounting processes. Tissue preparation processes can include, without limitation, deparaffinizing a specimen, conditioning a specimen (e.g., cell conditioning), staining a specimen, performing antigen retrieval, performing immunohistochemistry (IHC) labeling or other reactions, and/or performing in situ hybridization (ISH) labeling or other reactions, as well as other processes for preparing specimens for fluorescent, microscopy, microanalyses, mass spectrometric methods, or other analytical methods. If the specimen is a sample embedded in paraffin, the sample can be deparaffinized using appropriate deparaffinizing fluid(s). After the waste remover 130 removes the deparaffinizing fluid(s), any number of reagents can be successively applied to the specimen. The slide 120 can then be cover slipped to produce a wet mount slide, permanently mount slide, or the like.

Cell conditioning can make cross-linked antigenic sites more accessible by large biomolecules such as antibodies and nucleic acid probes. The slide processing apparatus 100 can perform cell conditioning protocols. Applying heat to the sample is one way to cell-condition, therefore heat can be supplied to the sample 187. Heat can be applied by direct application (conduction), indirect conduction (thought the microscope slide), convection (heated air directed onto the sample), or radiantly (infrared or microwave). The processing apparatus 100 can have any number of thermal elements for heating. Cell conditioning is typically performed by incubating the tissue sample from 75-100 degrees Celsius in an aqueous solution and holding it for some period until adequate antigenicity is attained, typically 30-90 minutes.

Samples can be processed with a wide range of substances, such as stains, probes, other reagents, rinses, and/or conditioners. The substances can be fluids (e.g., gases, liquids, or gas/liquid mixtures), or the like. The fluids can be solvents (e.g., polar solvents, non-polar solvents, etc.), solutions (e.g., aqueous solutions or other types of solutions), or the like. Reagents include, without limitation, stains, wetting agents, antibodies (e.g., monoclonal antibodies, polyclonal antibodies, etc.), antigen recovering fluids (e.g., aqueous- or non-aqueous based antigen retrieval solutions, antigen recovering buffers, etc.), or the like. Stains include, without limitation, dyes, hematoxylin stains, eosin stains, conjugates of antibodies or nucleic acids with detectable labels such as haptens, enzymes or fluorescent moieties, or other types of substances for imparting color and/or for enhancing contrast. In some embodiments, processing liquids in the form of reagents are applied to the samples. To reduce the volumes of liquids consumed during processing, concentrated liquids can be utilized. For example, concentrated reagents can be uniformly applied over samples with large surface areas to reduce processing costs and waste. A thin reagent film can be kept in contact with the sample to ensure enhanced and help ensure uniform reagent uptake by a sample. Excessive volumes of reagents can be conveniently removed in a controlled manner.

The slide 120 is a generally flat transparent substrate capable of carrying a specimen for examination using equipment, such as optical equipment, e.g., a microscope or other optical device. For example, the slide 120 may be a generally rectangular piece of transparent material having a front face 210 for supporting specimens. In some embodiments, the slide 120 has a length of about 3 inches (75 mm) and a width of about 1 inch (25 mm) and, in certain embodiments, may include a label, such as a bar code. In some embodiments, the slide 120 has a length of about 75 mm, a width of about 25 mm, and a thickness of about 1 mm. The slide 120 can be in the form of a standard microscope slide made of glass or other transparent material. The slide 120 can include a machine-readable code (such as a one- or multi-dimensional bar code or infoglyph, an RFID tag, a Bragg-diffraction grating, a magnetic stripe or a nanobarcode) with coded instructions that specify the type, sequence, and timing of the liquid(s) delivered for treatment of a particular specimen.

With reference to FIG. 8, an actuation assembly 180 of the base unit 110 includes actuators 182*a-e* (collectively "182") that may be selectively extended and retracted to move the substrate 140. The actuation assembly 180 can include, without limitation, one or more drives (e.g., linear drives, reciprocating drives, or the like), motors (e.g., stepper motors, drive motors, or the like), solenoids, piston assemblies, gear trains, combinations thereof, or other electronically, mechanically, hydraulically, or pneumatically driven components capable of moving the substrate 140. The actuation assembly 180 can be in the form of a platen assembly with the actuators 182 and a substrate 140. In such embodiments, the actuators 182 can include couplers for releasably holding the substrate 140. The couplers can be in the form of suction devices, mechanical couplers, or other types of couplers for allowing relative movement between the substrate 140 and the actuators 182. The illustrated couplers are in the form of a pin and bracket arrangement. In other embodiments, the actuators 182 are permanently connected to the substrate 140.

The substrate 140 overlays most of or substantially the entire sample 187. If the slide 120 is a standard microscope slide, the substrate 140 can have a length in a range of about 0.5 inch (13 mm) to about 3 inches (76 mm), a width in a range of about 0.5 inch (13 mm) to about 1 inch (25.5 mm), and a thickness in a range of about 0.02 inch (0.5 mm) to about 0.08 inch (2 mm). In some embodiments, the substrate 140 is a standard coverslip with a length of about 50 mm, a width of about 24 mm, and a thickness of about 0.2 mm. Other dimensions are also possible, if needed or desired. The substrate 140 can have a generally polygonal shape (e.g., square or rectangular), elliptical shape, or circular shape. The shape of the substrate 140 can be selected based on the shape and dimensions of the slide 120, as well as the shape and dimensions of the sample 187 and/or a holder. One or more thermal elements for heating/cooling can be incorporated into the substrate 140. Such embodiments are well suited to perform IHC processing, ISH processing, or the like. For example, thermal elements can be embedded in or coupled to the substrate 140 and connected to a power source of the actuator assembly 180. Heating/cooling can also be achieved via a processing chamber. For example, the slide processing apparatus 100 can be positioned within a temperature controlled processing chamber. The processing chamber can include heating/cooling elements, fluidics, vacuum lines, pressurization lines, valve mechanisms, combinations thereof, or the like. Of course, the slide processing apparatus 100 can be incorporated into conventional instruments, diagnostic equipment, or the like.

A plurality of gapping elements 183*a-i* (collectively "183") is positioned along the lower surface 200 of the substrate 140. The gapping elements 183 can keep the surface 200 spaced apart from the slide 120 to maintain a capillary gap. The heights of the gapping elements 183 can be equal to or greater than a thickness of the sample 187. If the substrate 140 is pressed against the slide 120, the gapping elements 183 can surround the sample 187 and maintain a gap suitable for maintaining a thin film. In certain embodiments, the gapping elements 183 can serve to limit compression of the sample 187. The gapping elements 183 may have heights that are approximately equal to or slightly less than a thickness of the sample 187 such that the sample 187 can be compressed without being damaged.

The substrate 140 can be made, in whole or in part, of one or more polymers, plastics, composites, glass, combinations thereof, or other suitable materials that may be generally rigid, semi-rigid, and/or compliant. For example, the substrate 140 can be a rigid glass plate. If the substrate 140 is flexible, the substrate 140 can be made of one or more polymers, such as polyester, polyethylene terephthalate, polypropylene, rubber, polyvinylidene fluoride, polytetrafluoroethylene, or combinations thereof. The composition of the substrate 140 can be selected based on desired characteristics, including, without limitation, surface energy, flexibility, wettability, chemical compatibility, adhesion characteristics, or the like. In some embodiments, the slide 120 and substrate 140 can be made of a hydrophobic material to ensure sufficient containment of the liquid 160.

The waste remover 130 includes a pressurization device 220 and a receiving line 230 extending from the pressurization device 220. The pressurization device 220 can draw the liquid 160 into the receiving line 230. The pressurization device 220 may include, without limitation, one or more pumps, vacuum devices, or other types of devices capable of pressurizing fluids or drawing a vacuum, or both. The pressurization device 220 can also include one or more waste reservoirs and/or can be connected to a separate waste reservoir. Waste can be delivered to the waste reservoir(s) for storage until subsequent disposal. In some embodiments, a disposal system is incorporated into the pressurization device 220. In other embodiments, waste received by the waste remover 130 is routed to an auxiliary disposal system. Waste can be conveniently disposed of without exposing operators or technicians, as well as other slide processing equipment, to waste.

The receiving line 230 can include, without limitation, one or more conduits, pipes, or other components through which fluid can flow. In some embodiments, the line 230 is a single lumen conduit. If the waste remover 130 delivers fluids onto the slide 120, the line 230 can be a multi-lumen conduit. Liquids can be delivered through one lumen to the slide 120 and waste can be withdrawn from the slide 120 through another lumen. An inlet 185 of the line 230 can include one or more openings, or other types of features, through which liquids can flow.

The processing apparatus 100 can have different modes of operation. In some embodiments, the apparatus 100 has a static mode and a dynamic mode. In the dynamic mode, the substrate 140 can be moved to agitate the liquid 160. For example, a rolling motion can provide generally even liquid coverage along the sample 187. The substrate 140 can be rolled back and forth across the sample 187 any number of times. If the liquid 160 has a relatively low viscosity, the substrate 140 can be moved at a relatively high speed. If the liquid 160 has a relatively high viscosity, the substrate 140 may be moved at a relatively low speed. The speed of the substrate 140 can be increased or decreased to increase or decrease agitation of the liquid 160. Agitation may effect fluid uptake rates, settling of constituents in the liquid 160, mixing of constituents, combinations thereof, or the like. The processing apparatus 100 can also be used to perform on-slide mixing to mix sequentially or concurrently dispensed fluids. For example, a first aliquot of the fluid 160 can be dispensed onto the slide 120. An aliquot of another fluid can be dispensed onto the substrate 140 and mixed using the fluid 160. Any number of fluids can be dispensed to produce a wide range of mixtures. In some modes of operation, the substrate 140 can be used to agitate the fluid 160. After agitating the fluid 160, another fluid can be dispensed between the slide 120 and the substrate 140. The substrate 140 then agitates both fluids to produce a mixture. Alternatively reagents may be mixed off the slide and dispensed onto the slide in a pre-mixed state.

In the static mode, the substrate 140 can be used to minimize, limit, or substantially prevent movement of the liquid 160. The substrate 140 can be held stationary with respect to the slide 120 and can assume a generally flat configuration, or a configuration with a relatively large radius of curvature, to avoid excessive evaporative losses. The apparatus 100 can be in a static mode to perform incubation or other processes may require a significant length of time.

Advantageously, a wide range of different volumes of liquid 160 can be used to provide dynamic processing and static processing, including high fluid volumes greater than about 100 μl, and low fluid volumes, such as fluid volumes less than about 100 μl. Other fluid volumes are also possible, if needed or desired.

Figure 10:
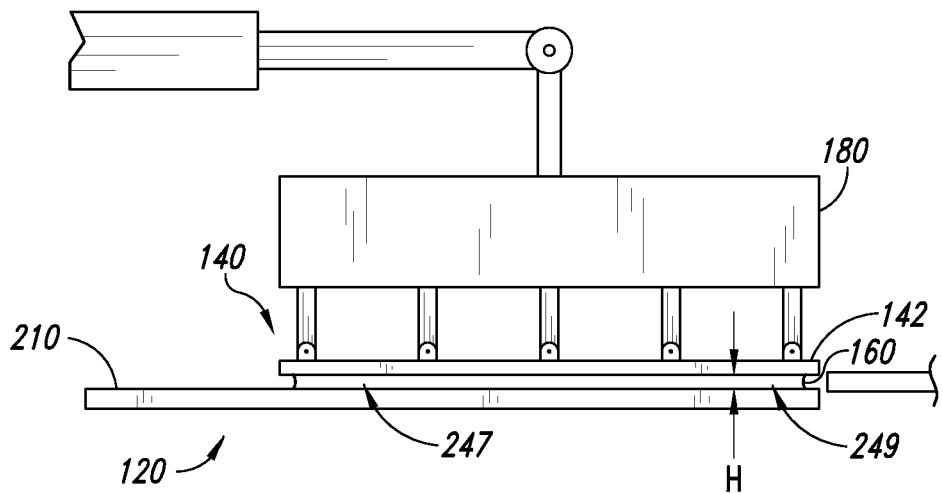

Referring to FIG. 10, the substrate 140 is in the flat configuration, can be used for static processing. Static processing can include, without limitation, incubating, thermal processing, or other types of processes involving a minimal amount of liquid movement.

A protocol may include using the substrate 140 to form thick layers, thin films, meniscus layers, or the like. To form thick liquid layers, the substrate 140 can be separated from the slide 120 and sample 187, as shown in FIG. 8. Such embodiments are well suited to treat the sample 187 using a high viscosity substance, such as a gel. If the gel inadvertently drains away, the gapping elements 183 can protect the sample 187 from unwanted compression and associated damage. To form a thin film, the gapping elements 183 can be pressed against the slide 120. If the substrate 140 is in a curved configuration, a meniscus layer can be formed.

Figure 11:
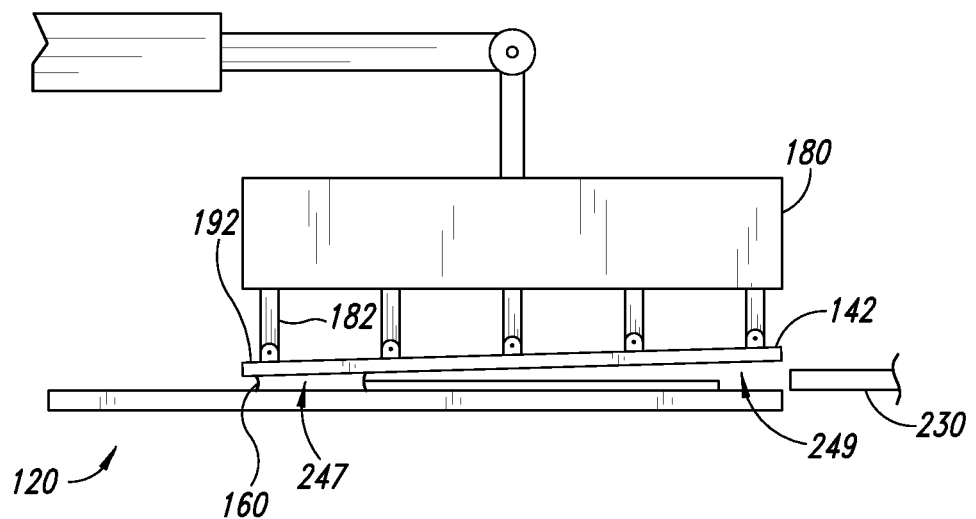
Figure 12:
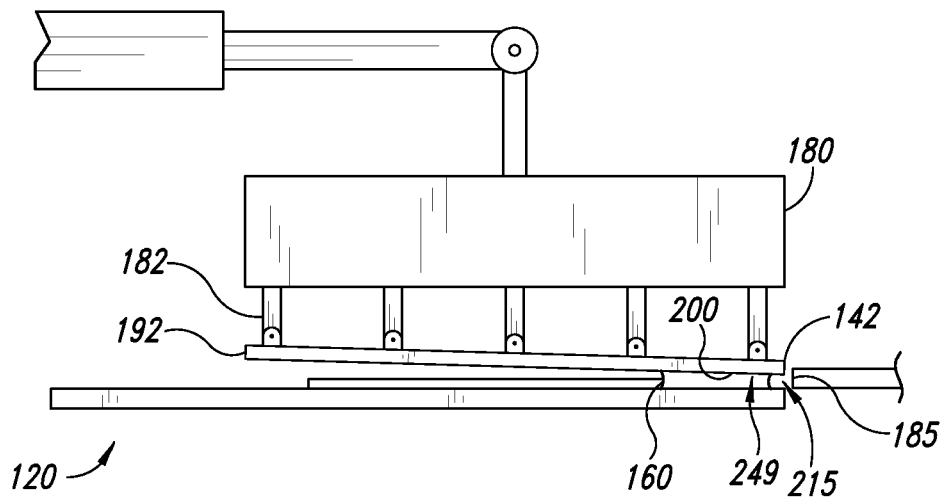
Figure 13:
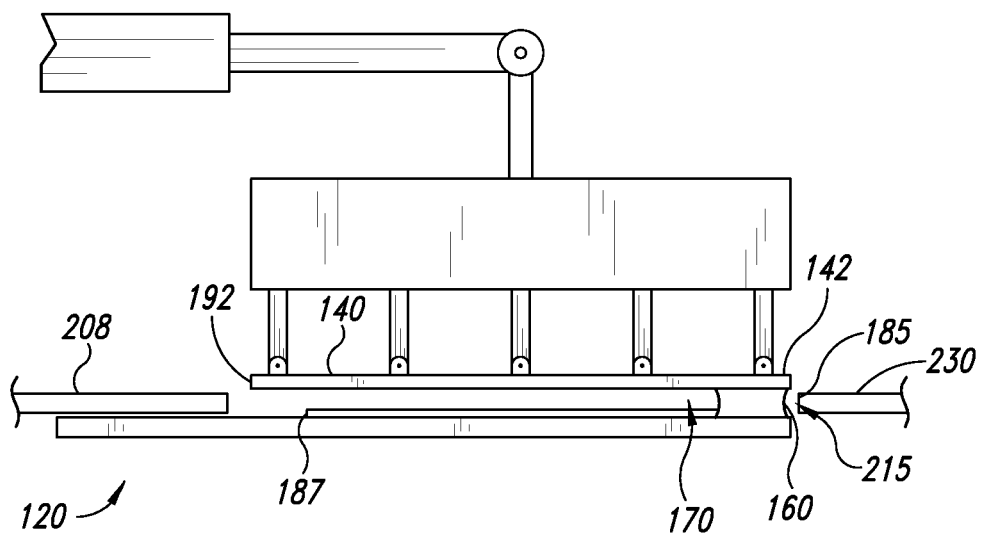

FIGS. 10-13 show one method of processing a sample. The liquid 160 can be moved towards a region 247 of the gap 170 via capillary action as an opposing region 249 of the gap 170 widens. FIG. 11 shows a bolus of liquid 160 at the region 247 of the substrate 140. The bolus of liquid 160 can be reapplied to the sample 187 by widening the region 247 and narrowing the region 249. As the region 249 narrows, the liquid 160 accumulates at the end 142. FIG. 12 shows the liquid 160 accumulated at the narrowed region 249. The waste remover 130 can then aspirate the bolus of liquid 160.

To further accumulate the liquid 160 and/or to reduce capillary forces, the end 142 of the substrate 140 can be moved away from the slide 120. As the angled lower surface 200 in FIG. 12 is rotated away from the slide 120, the liquid 160 is urged closer to an opening 215 of the inlet 185. The substrate 140 can be moved to a generally parallel orientation with respect to the slide 120 to move the liquid 160 as close as possible to the waste remover 130. The waste remover 130 can then draw the liquid 160 out of the gap 170.

The method of FIGS. 10-13 can be employed to accumulate liquid at a wide range of locations, including at the corners, sides, and/or ends of the substrate 140 and/or slide 120. The position of the waste remover 130 can be selected based on the desired location of waste accumulation.

Figure 14:
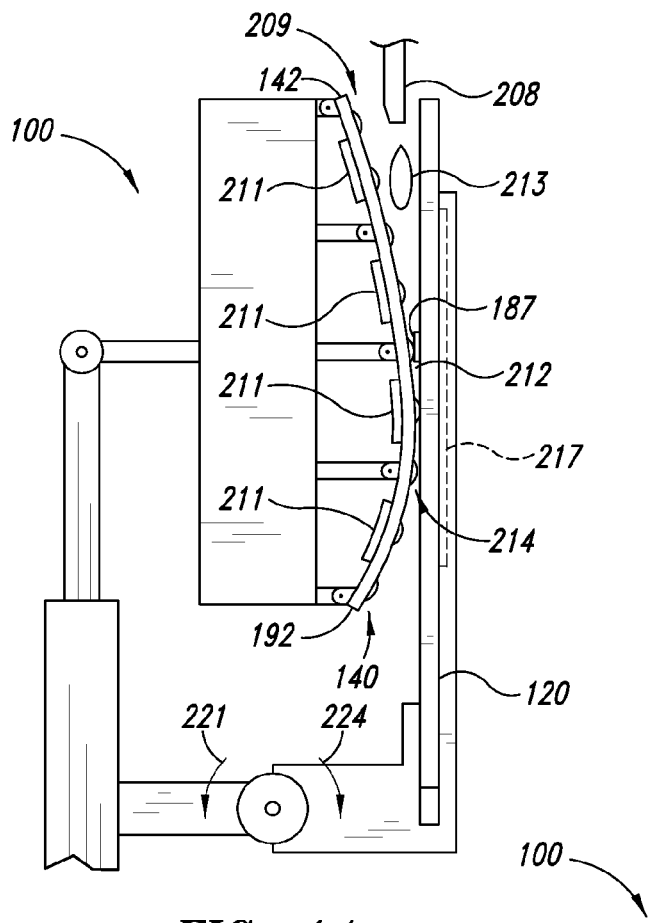
FIG. 14 is a side elevational view of a slide processing apparatus ready to treat a specimen carried on a microscope slide in a generally vertical orientation, in accordance with one embodiment.
Figure 15:
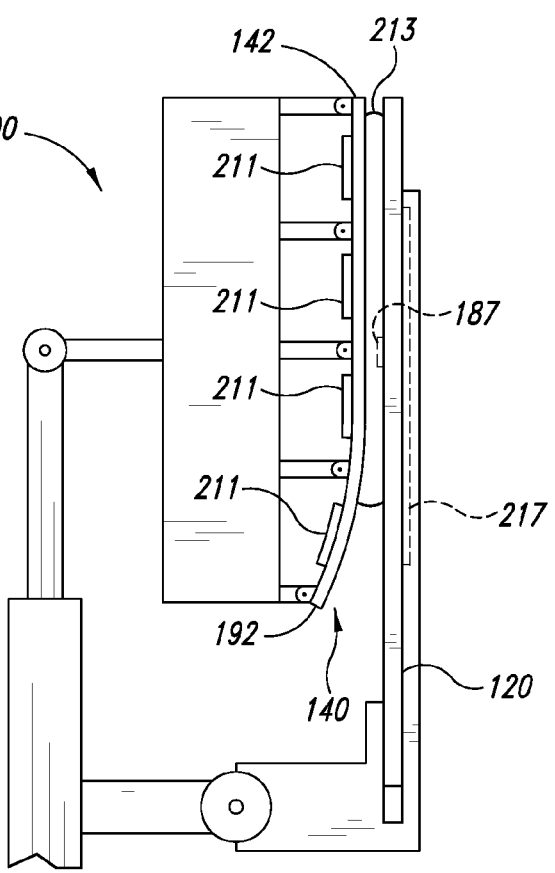
FIG. 15 is a side elevational view of the slide processing apparatus of FIG. 14 applying fluid to the specimen.

The processing apparatus 100 can process slides in different orientations, including a generally vertical orientation, horizontal orientation, inclined orientation, or the like. FIGS. 14 and 15 show the slide 120 in a generally vertical orientation to promote movement of a flowable substance 213 along the slide 120. The end 142 of the substrate 140 of FIG. 14 extends away from the slide 120 to form an enlarged gap 209. A dispenser assembly 208 can output the substance 213 through the relatively large gap 209 such that the substance 213 begins to collect at a narrowed region 212 of a capillary gap 214. The dispenser assembly 208 can be a pipette that dispenses the substance 213 comprising pre-mixed reagent. The volume of the dispensed substance 213 can be about 75 microliters to about 500 microliters. The substrate 140 can be rolled back and forth to move the substance 213 that fills the narrowed region 212, while gravity helps urge the substance 213 downwardly.

FIG. 15 shows the gap 214 filled with the substance 213. The lower end 192 of the substrate 140 can be moved towards the slide 120 to further spread the substance 213. The slide 120 and substrate 140 can be rotated together counterclockwise (indicated by an arrow 220 in FIG. 14) or clockwise (indicated by an arrow 224). To perform an incubation process, the slide 120 may be moved to a generally horizontal orientation, and the substrate 140 can assume a substantially flat configuration. To treat the sample 187 with another fluid, the slide 120 can be moved to an inclined or vertical orientation. The orientation of the slide 120 can be selected based on the processing to be performed, such as immunohistochemical processes (e.g., deparaffinization, antigen retrieval, and detection (cell conditioning)). For deparaffinization using the aqueous process described in U.S. Pat. No. 6,544,798B1 (aqueous deparaffinization using heat), incorporated herein by reference, heat can be supplied to heat either the substance 213 (e.g., an aqueous solution), which bathes the biological sample 187 above the melting point of paraffin, or a heater built into the substrate 140 could directly heat the sample 187. The heat can be sufficient to heat the sample 187 above the melting point of paraffin to release the paraffin into the immiscible aqueous phase where it is then removed. One or more heaters 211 may be activated to heat the substrate 140. Additionally or alternatively, a heater 217 can contact and heat the backside of the slide 120. The slide 120 can be at the inclined orientation to promote removal of the paraffin and/or any solvents, such as xylene or limonene. In some protocols, the volume of captivated fluid is kept in a range of about 15 microliters to about 25 microliters. In certain protocols, the volume of fluid is about 15 microliters. Any number of times during processing, a volume of reagent, reagent buffer, or water can be pipetted onto the slide 120 to restore fluid volume.

The processing apparatus 100 can perform on-slide-mixing. A first reagent can be dispensed. The substrate 140 is rolled to take up reagent between the slide 120 and the substrate 140. The substrate 140 is then positioned to allow access for pipette dispensing while maintaining fluid captivation. Another reagent is dispensed. The substrate 140 is then rolled longitudinally, laterally, or both to mix the reagents upon consecutive roll cycles. Incubation can be performed, if needed or desired.

Figure 16:
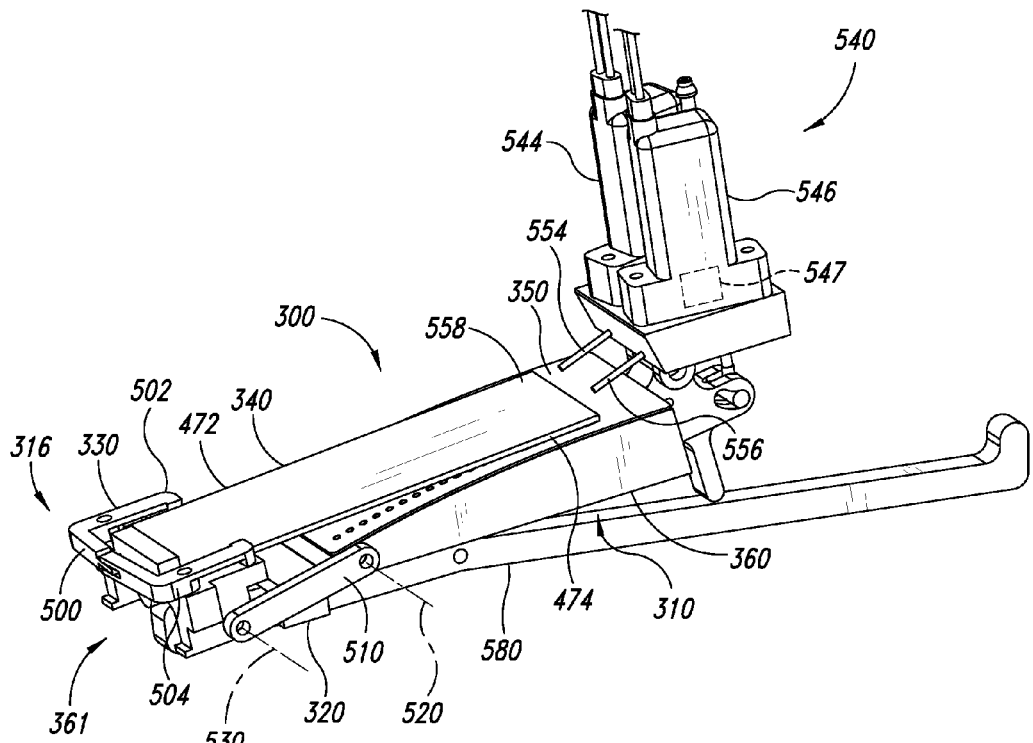
FIG. 16 is an isometric view of a slide processing station ready to treat a specimen carried on a microscope slide.
Figure 17:
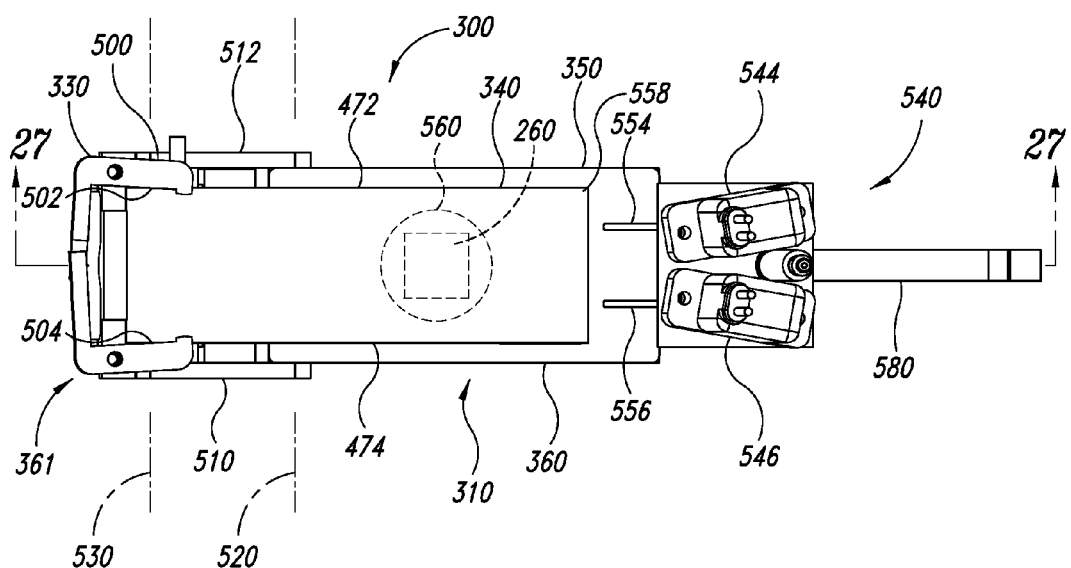
FIG. 17 is a top plan view of the slide processing station of FIG. 16.

FIGS. 16 and 17 show a slide processing station 300 including a roller unit 310 and a slide positioning device 316. The slide positioning device 316 includes a slide retaining device 330 holding a microscope slide 340 and an actuator 320 for activating the slide retaining device 330 (a gripper device is shown but other slide retaining embodiments will be apparent to those skilled in the art, such as by friction fit of at least a portion of the slide within a cavity or clamps or clips, for example). The slide 340 extends from the slide retaining device 330 in a cantilevered fashion and rests on the roller unit 310. The actuator 320 is mechanically coupled to the roller unit 310 and carries a slide retaining device 330. The slide 340 and a substrate 350 (illustrated in the form of a cover) can treat a specimen (illustrated in dashed line 260 in FIG. 17) on a bottom surface of the slide 340. The slide 340 can move along the cover 350 in a rolling motion to agitate liquid.

Figure 18:
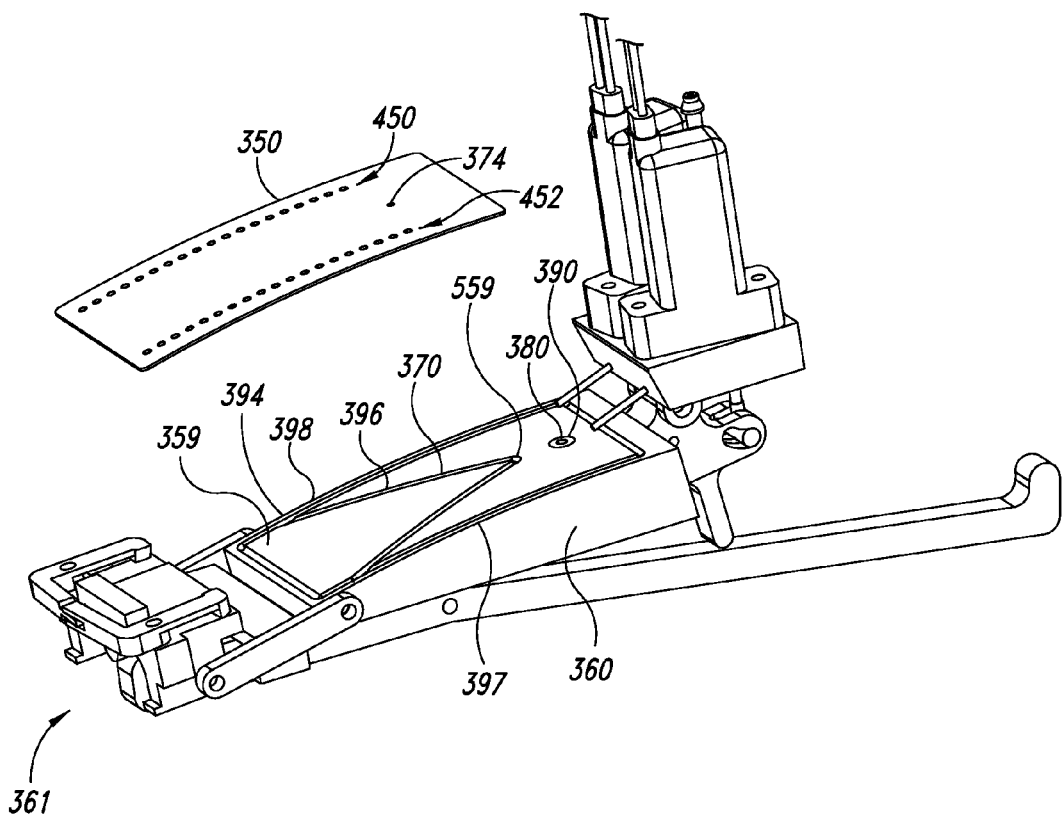
FIG. 18 is an isometric view of the slide processing station of FIG. 16 with a cover shown removed from a holder.

A platen assembly 361 of FIG. 18 includes the cover 350 and a base 360. The base 360 includes a network of channels 370 through which a vacuum can be applied to hold the cover 350 against a face 359 of the base 360. When the cover 350 overlays the base 360, a waste port 374 of the cover 350 is aligned with an entrance 380 of a waste passage of the base 360.

The network of channels 370 includes an outer channel 394 extending along the periphery of the base 360. An interior channel 396 extends between opposing sections 397, 398 of the outer channel 394. The outer channel 394 can hold the outer periphery of the cover 350 against the face 359, and the interior channel 396 can hold a central region of the cover 350 against the face 359. Other channel configurations are also possible.

The pattern, number, dimensions (e.g., width, depth, or the like) and configurations (e.g., U-shaped, V-shaped, or the like) of the channels can be selected based on the desired interaction between the cover 350 and the base 360. FIG. 19 shows an outer channel 400 and a transverse inner channel 402 extending between longitudinal sides 404, 406 of the channel 400. The inner channel 402 is generally midway between a waste port 409 and a bottom section 407 of the outer channel 400. A throughhole 408 can connect the outer channel 400 to a fluid line such that a vacuum can be applied via the throughhole 408. FIG. 20 shows a single continuous outer channel 412. FIG. 21 shows a network of channels including an outer channel 416 and a channel 420 that connects a flow inhibitor 418 to the outer channel 416. A vacuum applied via a throughhole 422 can both hold a cover against a face 423 and can aspirate the flow inhibitor 418. FIG. 22 shows a base 442 with a network of channels 429 including an outer channel 430 and an inner channel 432. The inner channel 432 extends longitudinally along a main body 440 of the base 442. An end 446 of the inner channel 432 is spaced apart from a flow inhibitor 448 so as to prevent fluid collected in the flow inhibitor 448 from entering the network of channels 429. The inner channel 432 is especially well suited to hold a central region of a cover securely against the main body 440.

Additionally or alternatively, the bases can include one or more clamps, adhesive layers, mechanical fasteners, or the like capable of selectively holding and releasing the cover 350. In some embodiments, the base 360 of FIGS. 16-18 is an electrostatic chuck. In yet other embodiments, the base 360 may include one or more receivers (e.g., holes, slots, or the like). The cover 350 can have protrusions or other features that are received by those receivers.

Referring to FIGS. 23-25, the cover 350 includes a first row of gapping elements 450 and a second row of gapping elements 452. A region 453 is between the two rows of elements 450, 452. The edges 454, 456 can be dimensioned with respect to the slide to provide the desired liquid application region 453 (e.g., the entire upper surface of the cover 350, most of the upper surface of the cover 350, the region between the elements 450, 452, or the like). In certain embodiments, substantially the entire upper surface of the cover 350 contacts the fluid being applied to the specimen. As such, most of the space between the cover 350 and the slide can be filled with the liquid. In some embodiments, the specimen can be positioned between the rows of elements 450, 452. A dispensed liquid can flow past the elements 450, 452 towards the edges 454, 456 of the cover 350.

In some embodiments, the gapping elements 450, 452 can help process a specimen with a desired amount of fluid (e.g., a minimal amount of fluid). The gapping elements 450, 452 can also be spaced apart from one another to prevent, limit, or substantially prevent wicking between adjacent elements. If a liquid reaches one of the gapping elements 450, 452, the liquid can reside at the contact interface between that gapping element and the slide 340 without flowing to an adjacent gapping element. The gapping elements 450, 452 are spaced apart from edges 454, 456 of the cover 350 to keep the liquid proximate to the liquid application region 453. Additionally, the liquid is kept far enough away from the edges 454, 456 to prevent wicking out from underneath the slide even if another object contacts the edges 454, 456.

The rows of gapping elements 450, 452 extend longitudinally along a length of the cover 350. Opposing gapping elements of each row 450, 452 are generally laterally aligned such that the slide 340 (see FIG. 16) can contact laterally aligned elements 450, 452. As the slide 340 is moved along the cover 350, the slide 340 is successively brought into contact with laterally aligned gapping elements 450, 452. Each of the rows 450, 452 can be generally similar to one another. Accordingly, the description of one of the rows 450, 452 applies equally to the other, unless indicated otherwise.

The row 450 can include about 5 gapping elements to about 60 gapping elements with an average distance between adjacent gapping elements in a range of about 0.05 inch (1.27 mm) to about 0.6 inch (15.24 mm). In some embodiments, including the illustrated embodiment of FIGS. 23 and 24, the row 450 includes 19 gapping elements that protrude outwardly from a surface 460, illustrated as a specimen facing surface. In other embodiments, the row 450 includes about 10 gapping elements to about 40 gapping elements. As viewed from above (see FIG. 24), the row 450 has a generally linear configuration. In other embodiments, the row 450 has a zig-zag configuration, serpentine configuration, or any other configuration or pattern.

The gapping elements 450 can be evenly or unevenly spaced from one another and can form an approximately straight row or can be staggered. The distance between adjacent gapping elements 450 can be greater than the heights of the gapping elements and/or less than a thickness t (see FIG. 26) of a body 459 of the cover 350. Other spacings are also possible, if needed or desired. A width W of the cover 350 can be in a range of about 0.6 inch (15.24 mm) to about 1.5 inch (38 mm). Other widths are also possible. In some embodiments, the width W is equal to or greater than a width of the slide 340. If fluid flows outwardly past the slide 340, the fluid can thus remain on the cover 350.

Referring to FIG. 24, a distance D between the rows 450, 452 can be selected based on the dimensions of the specimen and the dimensions of the slide 340. In some embodiments, the distance D is in a range of about 0.25 inch (6.35 mm) to about 1 inch (25 mm). If the slide 340 is a standard microscope slide, the distance D can be less than about 0.5 inch (12.7 mm).

FIG. 26 shows one of the gapping elements 450. The height H of the gapping element 450 can be selected based on the thickness of the specimen to be processed. The gapping element 450 can have a height H equal to or less than about 0.015 inch (0.38 mm) if the specimen is a tissue section with a thickness that is less than about 0.015 inch (0.38 mm). In some embodiments, the height H is in a range of about 0.001 inch (0.025 mm) to about 0.005 inch (0.127 mm). In certain embodiments, the height H is about 0.003 inch (0.076 mm) to process thin tissue sections with a thickness less than about 30 microns, 20 microns, or 10 microns. A ratio of the height H of the gapping elements 450 to the radius of curvature R of the main body 459 can greater than about 0.0001. For example, the ratio of the height H to the radius of curvature R can be in a range of about 0.0001 to about 0.0075.

The pattern, number, dimensions, and configurations of the gapping elements can be selected based on the desired interaction between the specimen and the liquid. If the cover 350 includes a field of gapping elements, the gapping elements can be distributed evenly or unevenly across the cover 350 to form different patterns that may include, without limitation, one or more rows, arrays, geometric shapes, or the like.

The gapping element 450 can be a partially spherical dimple, partially elliptical dimple, or the like. The illustrated element 450 is a substantially partially spherical dimple especially well suited for slidably contacting the slide 340 without damaging (e.g., marring or scratching) the slide 340. If the specimen is sufficiently large or moves towards one side of the microscope slide 340, the specimen can slide over the spherical dimple 450 without damaging or dislodging the specimen with respect to the slide 340. In other embodiments, the gapping element 450 can be in the form of a polyhedron protrusion, a conical protrusion, a frustoconical protrusion, or another combination of polygonal and arcuate shapes.

The main body 459 of FIG. 25 is in the shape of a simple arc with a radius of curvature R in a range of about 2 inches (5 cm) to about 30 inches (76 cm). In some embodiments, the radius of curvature R is about 15 inches (38 cm) or about 20 inches (74 cm). Such embodiments are well suited to mix reagents on the slide. The radius of curvature R can be selected based on the number of specimens to be processed, amount of fluid agitation, properties of the processing liquids, the height of gapping elements 450, 452, and the like. In other embodiments, the cover 350 is in the shape of a complex arc (e.g., an elliptical arc), compound arc, or the like. In yet other embodiments, the cover 350 can be substantially planar.

The cover 350 can be made, in whole or in part, of polymers, plastics, elastomers, composites, ceramics, glass, or metals, as well as any other material that is chemical compatible with the processing fluids and specimen. Exemplary plastics include, without limitation, polyethylene (e.g., high density polyethylene, linear low density polyethylene, blends, or the like), polyvinylidene fluoride (PVDF), polytetrafluoroethylene (PTFE), perfluoroalkoxy (PFA), or combinations thereof. If the cover 350 is disposable, the cover 350 can be made, in whole or in part, of a relatively inexpensive material. If the cover 350 is rigid, it can be made, in whole or in part, of polycarbonate, urethane, polyester, a metal coated plate, or the like. The cover 350 can have one or more pins, pegs, protrusions, receivers, or other features used to hold the cover 350.

The cover 350 can be formed by injection molding processes, compression molding processes, extrusion process, machining processes, or combinations thereof. For example, an injection molding process can be used to fabricate the main body 459 and gapping elements 450, 452. The waste port 374 can then be machined in the main body 440. In other embodiments, the cover 350 can be a mono-layer membrane, multi-membrane, film, or coating. An underlying component can have one or more gapping elements to which the cover 350 can conform to form corresponding gapping elements (e.g., bulges, protrusions, or the like). For example, gapping elements can be positioned on the face 359 of the base 360 of FIG. 18. When the cover 350 overlays the base 360, the cover 350 can conform to the gapping elements. As such, the cover 350 can be permissive to gapping elements.

If the cover 350 is in the form of a film, the film can include an adhesive layer. The adhesive layer can comprise, without limitation, one or more pressure sensitive adhesives, adhesive gels, binding agents, or the like. In some embodiments, the film is a sheet that is dispensed from a roll. Each slide can be processed with a different section of the sheet to prevent carryover contamination. In other embodiments, individual sheets with an adhesive layer are applied to platen assemblies. In some non-adhering embodiments, a sheet is held against the platen assembly via a vacuum. In other embodiments, a sheet is securely held against the platen assembly by both an adhesive layer and by applying a vacuum.

The cover 350 can also be in the form of a coating. A coating can be applied via a roller, a sprayer, a brush, or any other suitable applicator depending on whether the coating comprises a curable material, a thermoplastic material, thermosetting material, combinations thereof, or the like. In some embodiments, a liquid is applied to a surface (e.g., a surface of a platen assembly) and subsequently cured. An upper surface of the coating can define an application region. If the platen assembly includes gapping elements, the coating can be formed over the gapping elements.

Referring again to FIG. 16, the slide retaining device 330 in the form of a gripper device includes a spring clip 500 that grips the slide 340. The spring clip 500 is movable between an open or receiving position for receiving the slide 340 and a gripping position for gripping the slide 340. When the slide 340 is inserted between arms 502, 504 of the clip 500, the arms 502, 504 can securely grip the edges 472, 474. After processing, the slide 340 can be pulled out of the clip 500 without damaging the slide 340 and/or without disturbing a coverslip if the slide 340 has been coverslipped. Additionally or alternatively, the slide retaining device 330 can have one or more clamps, slots, or other components or features for selectively holding the slide 340.

The actuator 320 of FIGS. 16 and 17 includes elongate members 510, 512 rotatably coupled to the roller unit 310 and the slide retaining device 330. The elongate members 510, 512 can be links or other types of connectors. To move the slide 340 along the cover 350, an accumulator arm 580 is rotated to push upwardly on the slide retaining device 330 causing the elongate members 510, 512 to rotate about an axis of rotation 520 to keep the slide 340 substantially tangent to the cover 350.

The processing station 300 can also include a dispenser assembly 540 for outputting processing fluids. The dispenser assembly 540 includes a pair of units 544, 546, each capable of dispensing a fluid. Outlet ports 554, 556 of the units 544, 546, respectively, can be aimed at a gap between an end 558 of the slide 340 and the cover 350. The illustrated outlet ports 554, 556 are in the form of conduits through which substances can flow.

The units 544, 546 can include, without limitation, one or more fluid sources, pumps, filters, valves, or combinations thereof, as well as other fluidic components. In some embodiments, the units 544, 546 receive fluid from remote fluid sources and can dispense those fluids. In other embodiments, the units 544, 546 can contain fluid sources, such as fluid reservoirs. The fluid sources can be conveniently refilled or replaced when emptied.

The units 544, 546 can control the temperature of the fluids. The illustrated unit 546 of FIG. 16 includes a thermal element 547 (illustrated in phantom line) capable of heating or cooling a fluid. The thermal element 547 can include one or more heaters (e.g., resistive heaters) and/or cooling devices (e.g., Peltier devices). Additionally or alternatively, the units 544, 546 can include one or more mixing devices capable of mixing reagents. In some protocols, two or more reagents are delivered independently to the unit 544. The unit 544 can mix the two or more reagents before dispensing. In other protocols, premixed reagents are delivered to the units 544, 546.

The dispenser assembly 540 can also be in the form of one or more fluid dispensers, pipettes capable of carrying reagents (e.g., pre-mixed reagents, water, buffer, etc.), or the like. If the dispenser assembly 540 includes pipettes, the pipettes can be moved to sequentially deliver substances. A volume of a fluid (e.g., 75 microliters of a substance, 100 microliters of a substance, 500 microliters of a substance) is pipette onto the cover 350. The slide 340 is rolled manipulate the liquid. The thermal elements 680a, 680b may be activated to heat the slide 340. One or more times during processing, a volume of reagent, reagent buffer, water, or other substance is dispensed to, for example, restore fluid volume, adjust reagent concentration, or the like.

Figure 27:
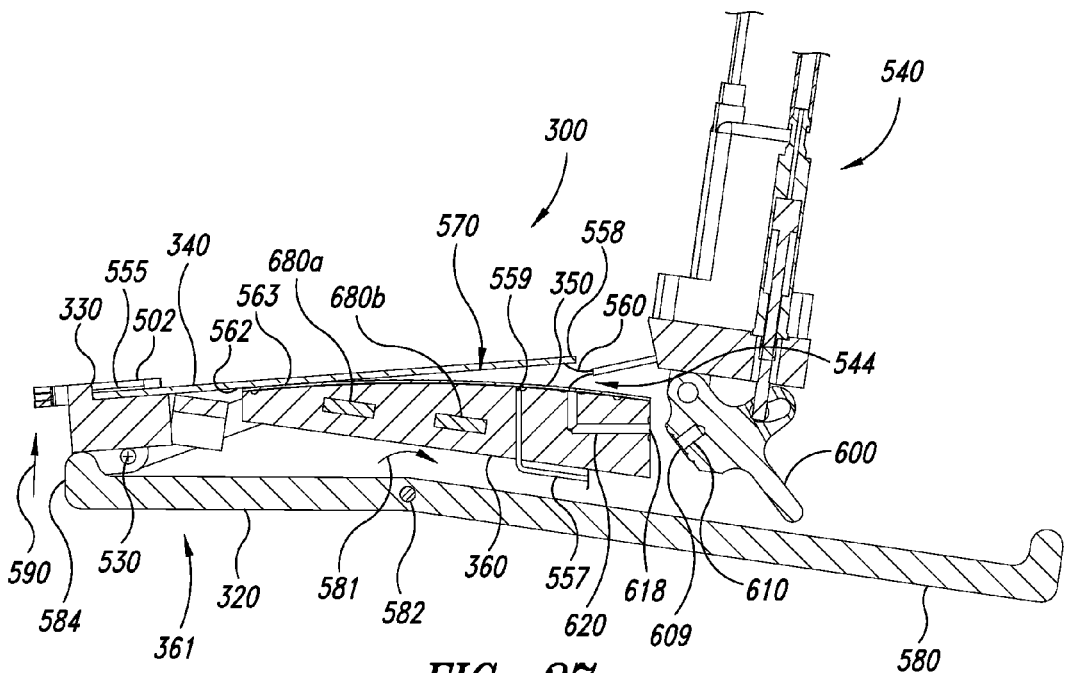
FIG. 27 is a cross-sectional view of the slide processing station taken along a line 27-27 of FIG. 17.
Figure 28:
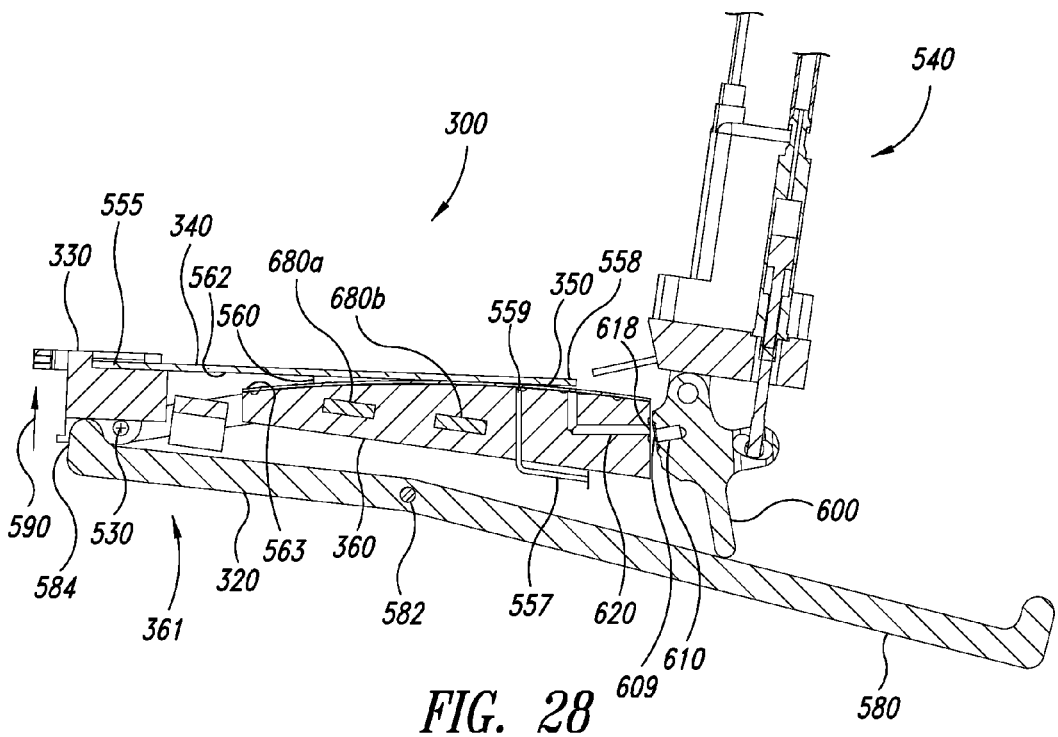
FIG. 28 is a cross-sectional view of the slide processing station moving a slide to agitate processing liquid.
Figure 29:
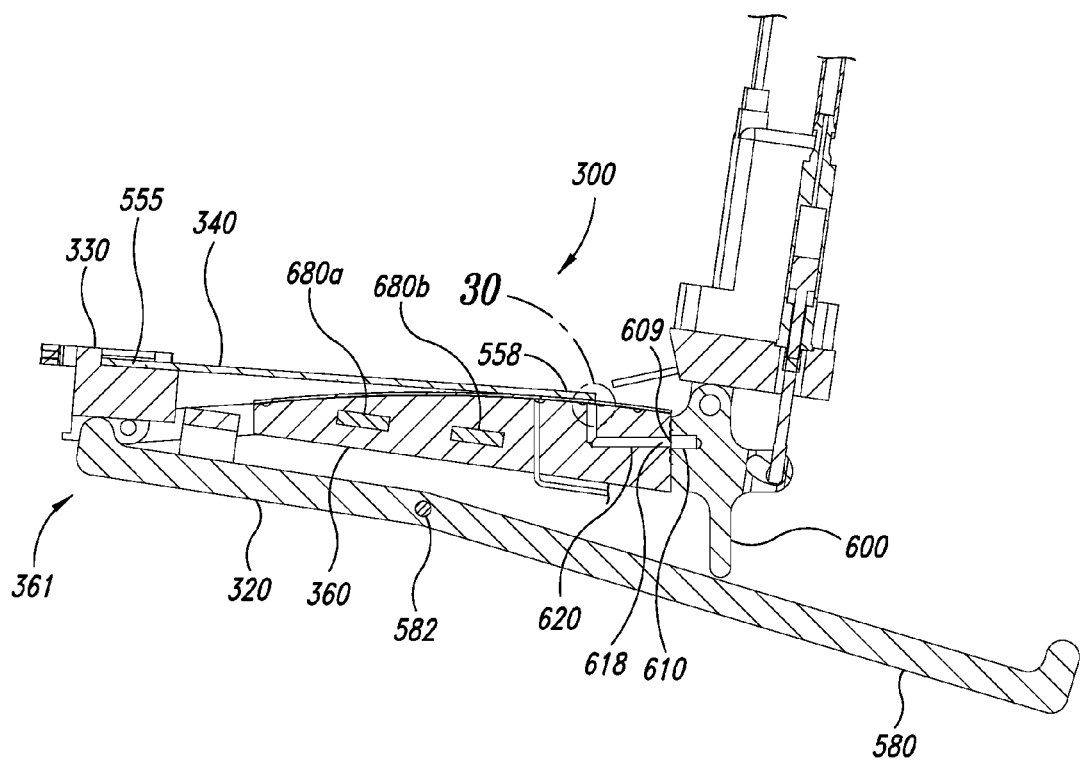
FIG. 29 is a cross-sectional view of the slide processing station with the slide positioned for waste removal.

FIGS. 27-29 show one method of processing a specimen. Generally, the slide 340 is loaded into the processing station 300. A substance is delivered between the slide 340 and the cover 350. The slide 340 is moved along the cover 350 to apply the substance to the specimen. After processing, the cover 350 is conveniently removed from the base 360 and replaced with another cover to continue processing the same specimen or to process another specimen.

To load the processing station 300, an end 555 (e.g., a label end) of the slide 340 can be slid into the slide retaining device 330. In some embodiments, the end 555 is manually inserted into the slide retaining device 330. In other embodiments, a robotic handler loads the slide 340. The slide retaining device 330 aligns the slide 340 with the processing station 300. Once loaded, the slide 340 can rest on an end portion 563 of the cover 350. The end 558 of the slide 340 extends upwardly away from the cover 350 to define an opening 544.

Referring to FIG. 27, the fluid dispenser 540 can deliver fluid 560 into the opening 544. The fluid 560 can travel along a varying height gap 570. A sufficient volume of fluid 560 can be dispensed to contact the specimen without moving the slide 340. Alternatively, the slide 340 can be moved to bring the fluid 560 into contact with the specimen.

FIGS. 17 and 28 show the fluid 560 (illustrated in dashed line in FIG. 17) applied to the specimen 260. If the fluid 560 reaches the gapping elements 450, 452, the fluid 560 may accumulate at the gapping elements 450, 452, thereby keeping the fluid 560 under the slide 340.

After the gap 570 of FIG. 27 is filled with a desired volume of fluid 560, the arm actuator 580 is rotated (indicated by an arrow 581) about a pin 582. As an end 584 of the arm actuator 580 moves upwardly (indicated by an arrow 590), the actuator 320 and slide retaining device 330 cooperate to move the slide 340 along the cover 350. The slide retaining device 330 can freely rotate about the axis of rotation 530 to keep the slide 340 proximate to or in contact with the cover 350. The slide 340 can float on the fluid 560.

The cover 350 can be securely held against the base 360 using a vacuum drawn via a port 559 and a vacuum line 557. This ensures that the cover 350 remains stationary as the slide 340 is manipulated.

In some dynamic modes of operation, the slide 340 is moved repeatedly back and forth to agitate (e.g., mix) the fluid 560. Most of the fluid 560 is rolled back and forth while residual fluid may be left on the surface of the tissue sample. The slide 340 can move some of the fluid 560 and mix it with the layer that is left on the surface of the sample. As such, the fluid 560 is continuously, vigorously mixed. The surface chemistry of the cover 350 and/or the slide 340 in contact with the biological sample may be selected based on hydrophobic/hydrophilic properties which affect the amount of liquid left on the surfaces of the cover 350 and/or slide 340. The cover 350 can be hydrophilic, hydrophobic, or both. In hydrophilic embodiments, the cover 350 can be made mostly of a hydrophilic material to allow convenient spreading of the applied fluid. In hydrophobic embodiments, the hydrophobic cover 350 and a hydrophobic slide can be used to limit spreading of the applied fluid. In other embodiments, the cover 350 may include one or more hydrophilic regions and one or more hydrophobic regions. For example, the cover 350 can include a hydrophilic central region and a hydrophobic outer region surrounding the central region. This allows a fluid to be spread easily along the central region while the surrounding outer region provides enhanced fluid management. The optimal surface characteristics of the cover 350 can be selected based on the desired spreading, containment of the liquid, and/or properties of the slide 340. When using an aqueous solution, a hydrophobic slide surface and a less hydrophobic cover 350 can cooperate to keep the solution within the space demarcated by the slide 340 and the cover 350. The aqueous solution will be repelled by the hydrophobic slide 340 and spread along the cover 350. Conversely, a hydrophilic slide 340 will spread the solution more over the slide surface 562, resulting in more "puddles" on the slide 340. The optimal surface characteristics of the cover 350 and/or slide 340 can be selected based on the desired containment/spreading of the liquid.

For on-the-cover mixing, a first reagent can be dispensed onto the cover 350. The slide 340 is rolled to take up the reagent. The slide 340 can be moved to an over-roll position to provide access between the cover 350 and slide 340 while maintaining fluid captivation. A second reagent is dispensed on the cover 350. The slide 340 is rolled to mix the reagents on consecutive roll cycles.

To remove the fluid 560, a waste manifold member 600 from a standby position shown in FIG. 27 to a waste removal position shown in FIG. 29. As the waste manifold member 600 reaches the waste removal position, an entrance 609 of a passage 610 of the manifold member 600 is mated with an outlet 618. The waste manifold member 600 moves the arm actuator 580, which in turn moves the slide 340 to a waste removal position, as shown in FIG. 29. The end 558 of the slide 340 of FIGS. 29 and 30 overlays the waste port 374, such that the fluid 560 can be removed via the waste port 374. Gravity, a vacuum, wicking materials, or the like can be used to draw the fluid into and through the waste port 374. In some embodiments, the fluid 560 can flow through the waste port 374 to a reservoir, absorbent member, or the like. The reservoir can be a waste container, disposal system, or the like. The absorbent member can be made, at least in part, of a highly absorbent material, including sponge material, wicking material, or the like.

If the fluid 560 passes through the waste port 374 primarily due to gravity, an absorbent member (e.g., a pad or a sheet) can be positioned below the waste port 374. In some embodiments, the absorbent member is adhered directly to the bottom surface of the cover 350. Of course, the absorbent member can be at any other suitable location, if needed or desired.

Figure 30:
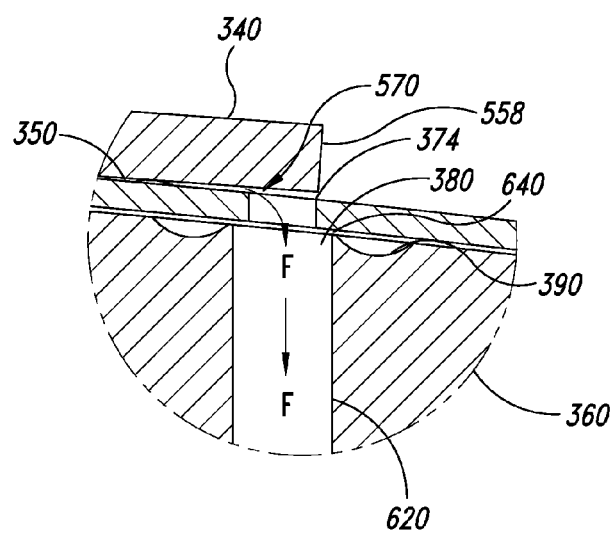
FIG. 30 is a detailed cross-sectional view of a portion of the slide processing station of FIG. 29.

If a vacuum is applied via the passage 610, the fluid 560 can flow along the capillary gap 570 towards and ultimately through the waste port 374. FIG. 30 shows the fluid F flowing downwardly through the waste port 374 and through the entrance 380 of the base 360. The fluid F proceeds along a passage 620 towards the outlet 618. In this manner, the fluid F flows along a fluid path through the cover 350 and the base 360.

In some embodiments, substantially no residual liquid 560 remains in the gap 570 after the vacuum has been applied for a sufficient length of time. Appropriate surface finishes (e.g., surface smoothness) and surface energy (e.g., the energy determined by the surface chemistry of the cover 350) can be selected to enhance the tendency of the fluid 560 to flow smoothly and completely from the gap 570. A higher level of smoothness and a lower surface energy will favor migration along the gap 570, whereas more surface imperfections and higher surface energy will tend to retain the liquid 560 in the gap 570.

A flow inhibitor 390 of FIG. 30 can minimize, limit, or substantially prevent the flow of fluid away from the entrance 380 along the interface of the cover 350 and the base 360. The flow inhibitor 390 can be an annular U-shaped channel surrounding the entrance 380. If fluid migrates along an interface 640, the fluid will flow into and collect in the flow inhibitor 390. The flow inhibitor 390 can thus serve as a reservoir and may be emptied periodically. Any number of flow inhibitors, sealing members, relief features, or the like can be used to minimize, limit, or substantially prevent fluid flow underneath the cover 350 due to wicking and/or capillary action.

In some embodiments, including the illustrated embodiment of FIG. 27, the base 360 includes thermal elements 680a, 680b (collectively "680") adapted to convert electrical energy to thermal energy. The thermal elements 680 can support different protocols that require thermal cycling, even rapid thermal cycling for ISH, IHC, or the like. When the thermal elements 680 generate heat, heat is transferred through the cover 350 to the specimen. The amount of electrical energy delivered to the thermal elements 680 can be increased or decreased to increase or decrease the temperature of the specimens and processing liquid.

The thermal elements 680 can be resistive heating elements. Different types of resistive heating elements (e.g., plate resistive heaters, coil resistive heaters, strip heaters, or the like) can be selected based on the desired operating parameters. Other types of thermal elements, such as cooling elements, heating/cooling elements, or the like, can be utilized. As used herein, the term "cooling element" is a broad term that includes, without limitation, one or more elements capable of actively absorbing heat so as to effectively cool at least a portion of the sample, processing fluid, and/or slide 340. For example, a cooling element can be a cooling tube or channel through which a chilled fluid flows.

In some embodiments, the elements 680 are heating/cooling elements, such as Peltier devices. Peltier devices may be solid state components which become hot on one side and cool on an opposing side, depending on a direction of current passed there through. By simply selecting the direction of current, the Peltier device can be employed to heat the slide 340 for a desired length of time. By switching the direction of the current, the elements 680 cool the slide 340. In other embodiments, the heating/cooling elements 680 are channels through which a working fluid flows. Heated fluid can be passed through the channels for a heating period, and a chilled fluid can be passed through the channels for a cooling period. The position, number, and type of heating/cooling elements 680 can be selected based on the desired temperature profile of the base 360.

Additionally or alternatively, the cover 350 can include thermal elements, such as heating elements for producing heat during a heating period and cooling elements for absorbing heat during a cooling period. For example, the cover 350 can have one or more embedded thermal elements. When the cover 350 is mated with the base 360, the electrical connection can be established such that the base 360 provides electrical energy to the thermal elements.

Thermal devices can also be used to transfer heat through the slide 340. Such thermal devices can be placed on the backside of the slide 340 to transfer heat through the slide 340 to the specimen. In some embodiments, both the cover 350 and a thermal device on the backside of the slide 340 cooperate to control the temperature of the specimen. In some modes of operation, the thermal device overlying the slide 340 can transfer heat through the slide 340 to a specimen. To cool the specimen, thermal devices (e.g., cooling channels) in the cover 350 can absorb heat. In this manner, the specimen can be heated or cooled.

Figure 31:
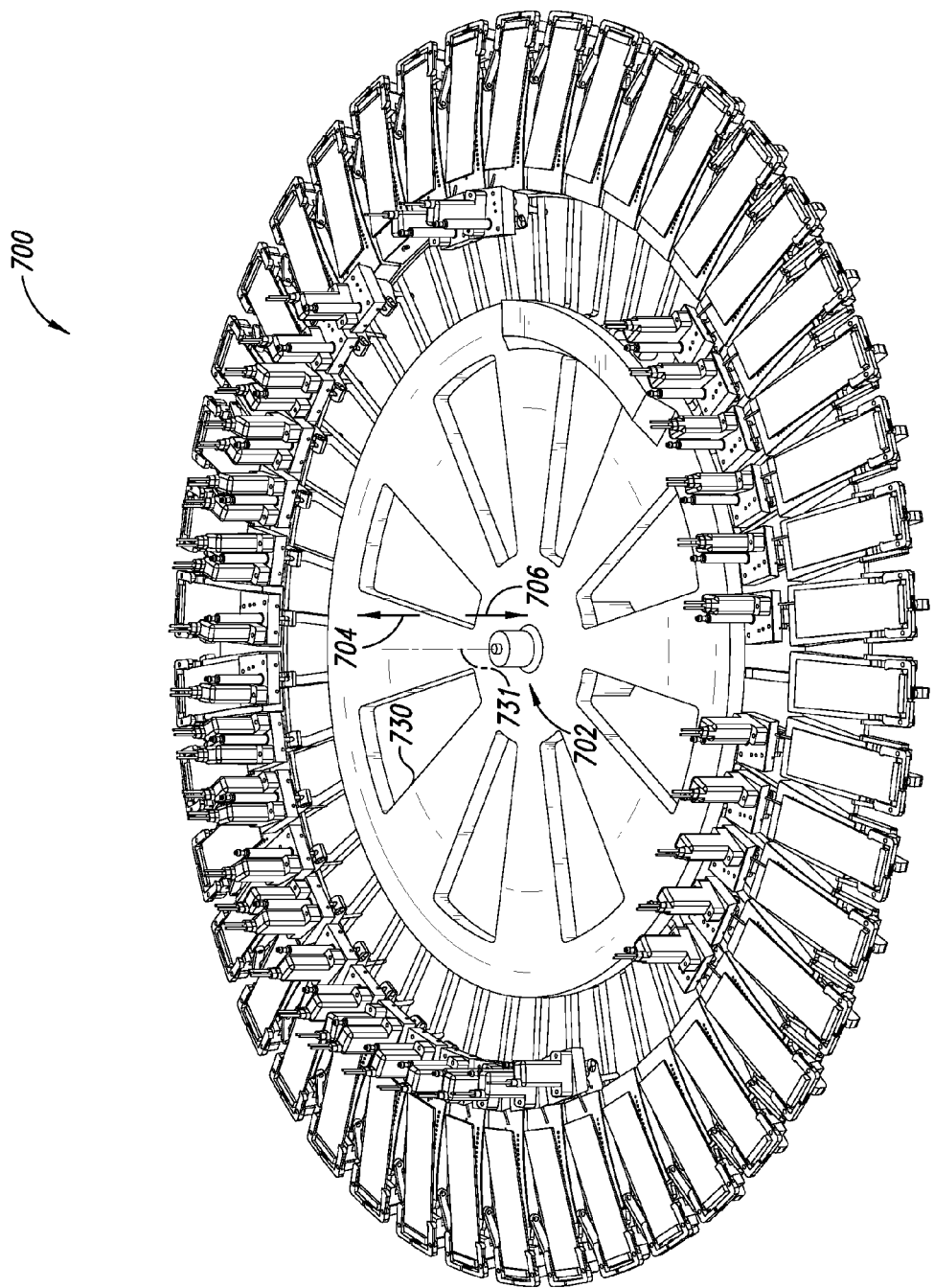
FIG. 31 is an isometric view of a staining system including a circular array of slide processing stations.

FIG. 31 shows a staining system 700 with an array of slide processing stations. The staining system 700 is shown with slides loaded into each of the processing stations. Some of the slide processing stations include fluid dispensers for automatically processing specimens. An operator, or an external fluid delivery system, can deliver fluids onto the slides at the processing stations without fluid dispensers. The external fluid delivery system can be a robotic pipette system. In other embodiments, all of the processing stations can include fluid dispensers such that each processing station can perform an individual protocol. Readers can be incorporated into the processing stations and can acquire information from the slide to determine an appropriate protocol.

Each of the processing stations can be mechanically connected to a drive mechanism 702. The drive mechanism 702 can be moved vertically (indicated by arrows 704, 706) to move the slides. By way of example, an end 720 of the arm actuator 580 of FIG. 27 can be coupled to a circular plate 730 of the drive mechanism 702. The circular plate 730 is moved downward (indicated by the arrow 706 in FIG. 31) to move the slides radially inward and is moved upward (indicated by the arrow 704 in FIG. 31) to move the slides radially outward. The fluid dispensers remain stationary as the slides are moved. To simultaneously process specimens, the fluid dispensers can dispense fluid to the respective processing stations when the plate 730 is in a raised position. After dispensing, the plate 730 can be repeatedly moved up and down to oscillate each of the microscope slides to agitate the fluids. The plate 730 can be rotated about an axis of rotation 731 to move the slides to the stationary fluid dispensers to perform an entire protocol without removing the slides. The applied liquids can be removed from each slide at a desired time. This allows individualized slide processing at each station.

The drive mechanism 702 can also include, without limitation, one or more motors, gear trains, linear slides, actuators, piston assemblies, combinations thereof, or the like. The components of the drive mechanism 702 can be selected based on the arrangement of the processing stations.

To provide independent parallel processing, each processing station can be connected to an independently operable drive mechanism. Different protocols can be performed at different stations.

In some embodiments, the staining system 700 is a conveyer based stainer. Slides can be loaded manually or by using a separate loader. The slides can be loaded at a particular location, for example, every 15 to 20 seconds. The circular array of slide holders (including slides, grippers, clips, disposables, curved platens, etc.) can be periodically advanced to an adjacent fluid dispenser. Other components of the staining station 700 can remain stationary (e.g., fluid dispensers, waste ports, etc.). For hematoxylin and eosin staining (H&E staining), the slides are moved around the wheel so that the specimens receive different liquids in the proper order and timing. Multiple liquids can be spread out to accommodate different protocols. At the last station, the slides can be coverslipped and then removed from the wheel. Fluid dispensers can be added or removed from the illustrated staining system 700 to perform different types of protocols. The staining system 700 thus provides flexibility for processing to perform primary staining, special staining, IHC, IHS, H&E staining, or the like.

Figure 32:
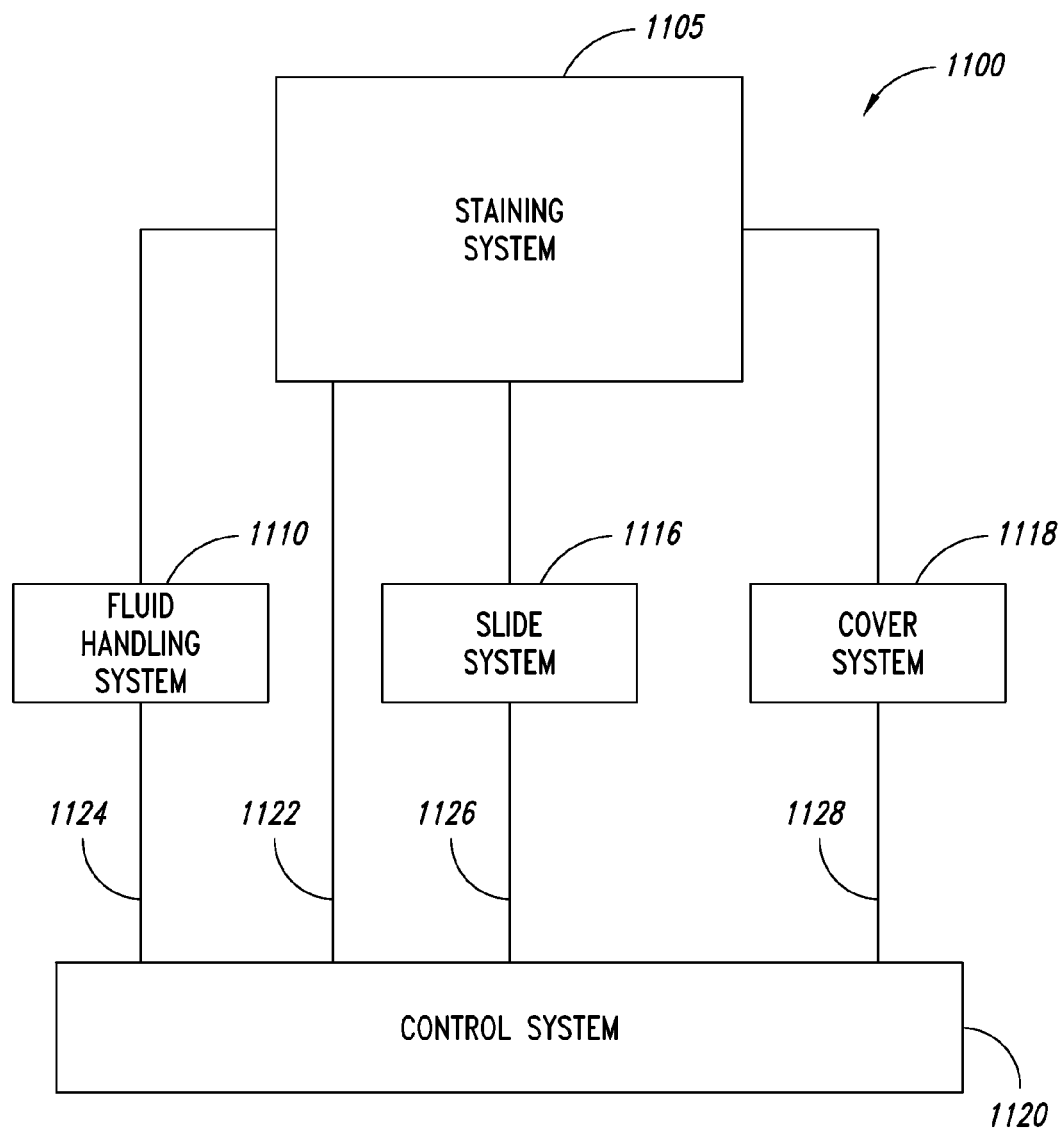
FIG. 32 shows an automated processing system, in accordance with one embodiment.

FIG. 32 shows an automated processing system 1100 that includes a staining system 1105, a fluid handling system 1110, a slide system 1116, and a cover system 1118. The staining system 1105 can process slides from the slide system 1116 using fluid from the fluid handling system 1110 and covers from the cover system 1118. The slides can be processed without human intervention to avoid problems associated with manually handling slides and reagents.

In some embodiments, the staining system 1105 includes a movable carousel with slide processing stations, such as the staining system 700 shown in FIG. 31. Valve mechanisms, temperature control systems, sensors, or other systems (e.g., coverslippers) can be incorporated into the staining system 1105. The slides can be coverslipped at processing stations by flipping slides such that a coverslipper can place a coverslip over specimens. The coverslipped slide can be removed from the staining system.

The fluid handling system 1110 can include, without limitation, one or more containers for holding substances. The containers can be connected to the staining system 1105 by one or more fluid lines. Solvents (e.g., polar solvents, non-polar solvents, etc.), solutions (e.g., aqueous solutions or other types of solutions), mounting media, reagents, or the like can be delivered through the lines. Substances from the containers can be used to perform different protocols, such as staining protocols (e.g., primary staining, special staining, IHC, ISH, or the like), antigen retrieval protocols, or the like. The fluid handling system 1110 can also include one or more pumps, filters, fixed nozzles (e.g., fixed nozzle fluid dispensers), pipette systems, or other types of fluid dispensers. Fixed nozzle fluid dispensers are especially well suited to delivery H&E fluids, bulk advanced stain fluids, or the like. Pipette systems are especially well suited to output non-bulk advanced stain fluids.

The slide system 1116 can provide slides carrying samples ready for processing. The slide system 1116 can include, without limitation, heaters or slide dryers (e.g., conductive dryers, convection dryers, ovens, etc.), as well as other types of components or devices used to prepare samples. The slide system 1116 can also include any number of racks, trays, cartridges, or other structures suitable for holding a desired number of slides. One or more slide transporters can move slides between components of the slide system 1116 and can load and unload the staining system 1105.

The cover system 1118 can include, without limitation, one or more racks, trays, cartridges, receptacles, or any other structures suitable for holding a desired number of covers or other types of substrates. One or more transporters can carry covers between components of the cover system 1118. The covers can be disposable covers or multi-use covers. To prevent carryover and other contamination, the covers can be single-use.

The processing system 1100 further includes a control system 1120 that communicates with various components. The control system 1120 is communicatively coupled to the staining system 1105 by a wired connection 1122 and is communicatively coupled to the fluid handling system 1110, slide system 1116, and cover system 1118 by wire connections 1124, 1126, 1128, respectively. Communication can also be accomplished through wireless connections (including wireless network connections) and/or optical connections.

The control system 1120 can generally include, without limitation, one or more computers, central processing units, processing devices, microprocessors, digital signal processors, central processing units, processing devices, microprocessors, digital signal processors (DSP), application-specific integrated circuits (ASIC), readers, and the like. To store information, the control system 1120 includes, without limitation, one or more storage elements, such as volatile memory, non-volatile memory, read-only memory (ROM), random access memory (RAM), or the like. The stored information can include optimization programs, tissue preparation programs, calibration programs, indexing programs, or other executable programs. The control system 1120 can execute optimization programs to optimize performance (e.g., reduce excess reagent consumption, reduce coverslipping time, increase productivity, improve processing consistency, or the like). The processing may be optimized by determining, for example, an optimum schedule to increase processing speeds, to increase throughput (e.g., a number of slides processed in a length of time), or the like. Such optimum schedule can be a schedule of preparing and delivering slides to the staining system 1105. In some embodiments, the control system 1120 determines loading sequences to reduce processing wait times. The control system 1120 can also be programmed such that loading of the pipettes, nozzles, or fluid dispensers for the next specimen can start during processing of the currently loaded specimen. This saves time because fluids can be dispensed onto the next specimen as soon as the current specimen is removed from the station.

The processing system 1100 can include any number of the transporters. Transporters can include, without limitation, one or more robotic handlers or arms, X-Y-Z transport systems, conveyors, combinations thereof, or other automated mechanisms capable carrying items between locations. Transporters can have end effectors to carry items. End effectors may include, without limitation, grippers, suction devices, holders, clamps, or the like. The end effectors can have temperature sensors, vacuum sensors, surface sensors, position sensors, or the like. In some embodiments, vacuum sensors of an end effector are capable of detecting the presence of an item, or other characteristics of the covers, slides, specimens, or the like. End effectors can load both slides and covers into the staining system 1105. After processing, the end effectors can retrieve the slides and covers.

Figure 33:
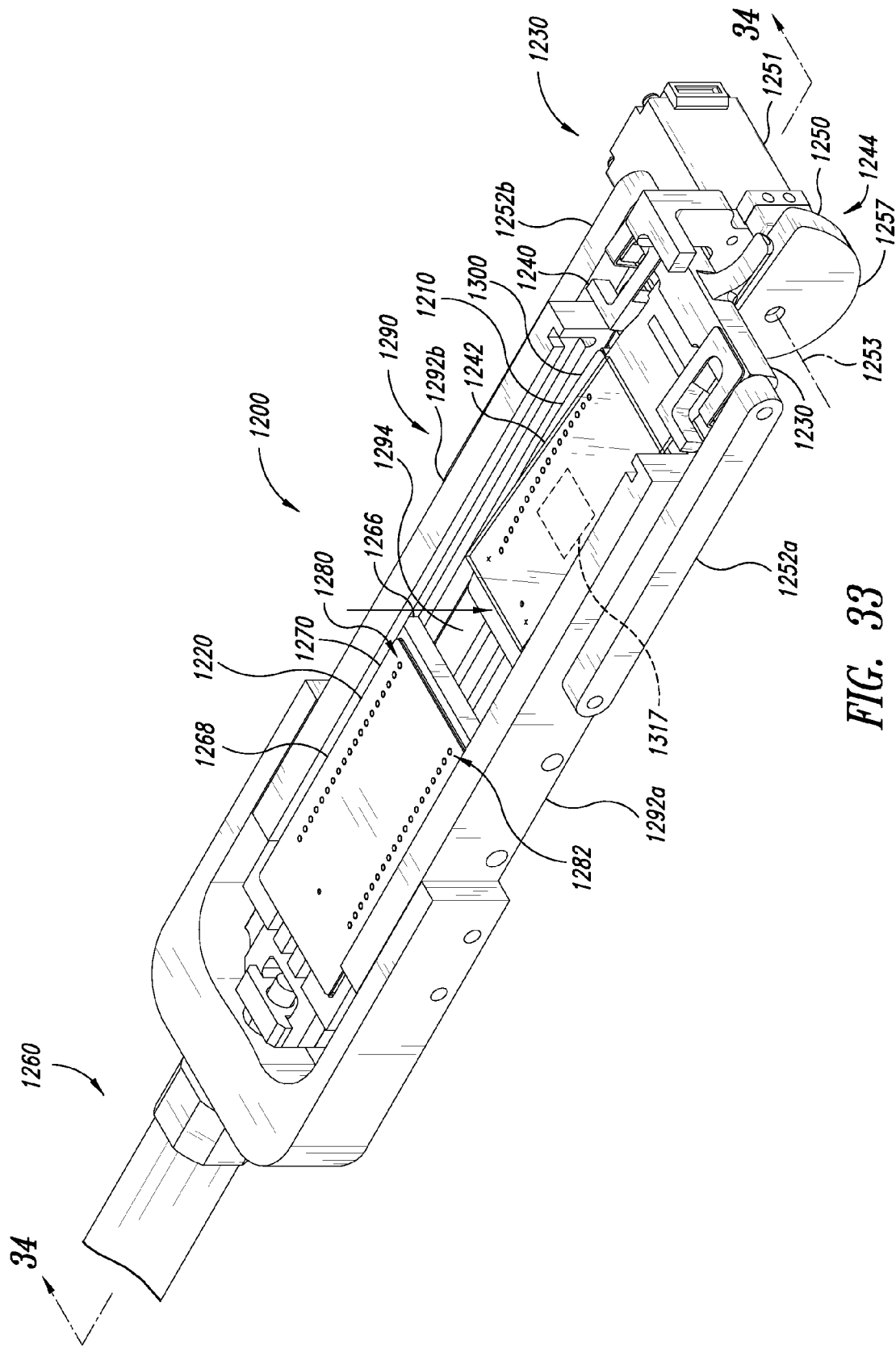
FIG. 33 is an isometric view of a slide processing station having a pair of platen assemblies, in accordance with one embodiment.
Figure 38:
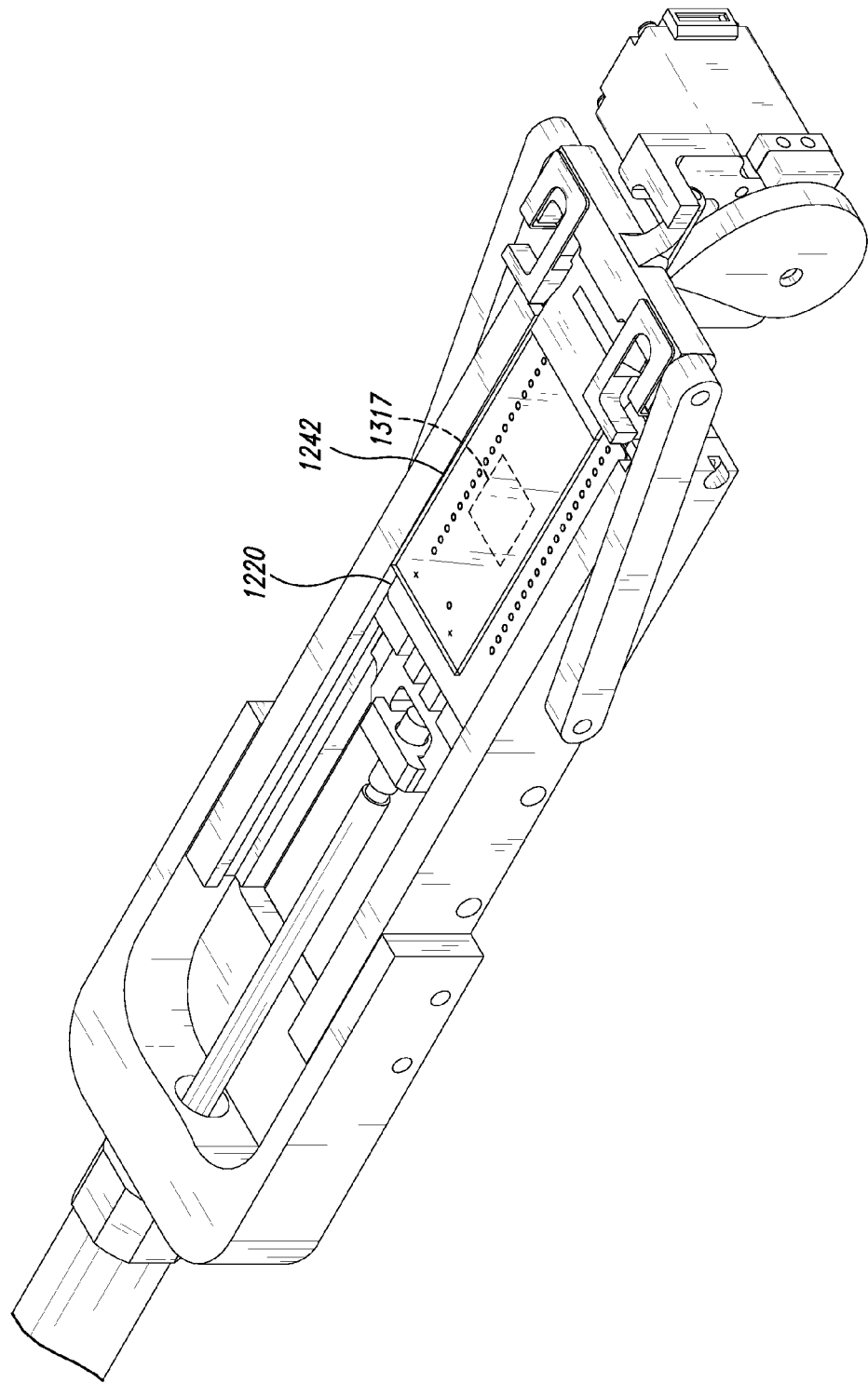
FIG. 38 is an isometric view of an upper platen assembly positioned between the slide in a raised position and the lower platen assembly.

FIG. 33 shows a processing station 1200 for processing a specimen using multiple platen assemblies. The processing station 1200 includes a stationary lower platen assembly 1210 and a movable upper platen assembly 1220. A slide positioning device 1230 includes a slide retaining device 1240 and a roller mechanism 1244. A sample 1317 (illustrated in dashed line) can be alternatingly processed by the platen assemblies 1210, 1220. In the illustrated configuration, the lower platen assembly 1210 is ready to treat the specimen 1317. The slide positioning device 1230 can raise a slide 1242 carrying the specimen 1317. When the slide 1242 is raised, a drive mechanism 1260 can translate the upper platen assembly 1220 along a rail apparatus 1290 from a standby position (shown in FIG. 33) to a processing position (see FIG. 38) directly above the lower platen assembly 1210. The slide 1242 is then lowered onto the upper platen assembly 1220.

The rail apparatus 1290 includes a pair of rails 1292*a*, 1292*b* (collectively "1292") and a support 1294 extending between the rails 1292*a*, 1292*b*. The rail 1292*a* retains one side of a cover holder 1266, and the other rail 1292*b* retains the other side of the cover holder 1266. The cover holder 1266 can slide along slots in the respective rails 1292 between the standby position and the processing position. The sizes, configurations (e.g., straight configuration, curved configuration, or the like), and features (e.g., slots, tracks, stops, or the like) of the rails 1292 can be selected based on the desired motion of the upper platen assembly 1220.

Figure 34:
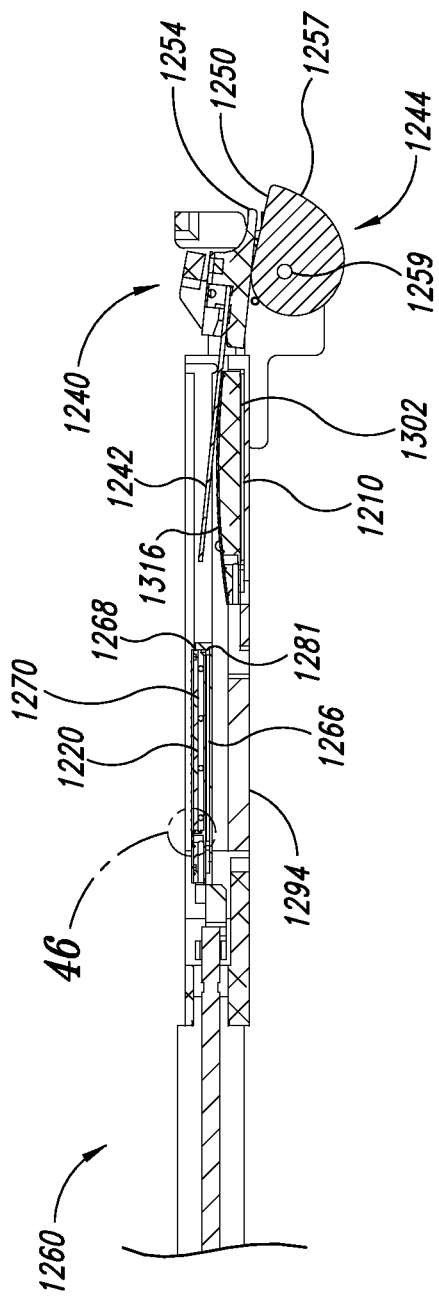
FIG. 34 is a cross-sectional view of the slide processing station of FIG. 33 taken along a line 34-34.

Referring to FIGS. 33 and 34, the upper platen assembly 1220 includes the cover holder 1266 and a cover 1268. The cover 1268 includes a substantially flat surface 1270 and two rows of gapping elements 1280, 1282. The cover holder 1266 includes thermal elements 1281 that can provide heating and cooling capabilities. In some embodiments, the thermal elements 1281 can be cooling devices including channels through which chilled liquid flows. Feedback from sensors (e.g., thermistors) can be used to control the thermal elements 1281. In certain embodiments, the holder 1266 includes a plate with embedded thermal elements 1281. The plate can be made of metal or other thermally conductive material to provide rapid heat transfer to the cover 1268. Additionally or alternatively, temperature sensors can be positioned between the cover holder 1266 and the cover 1268. In yet other embodiments, one or more sensors are incorporated into the cover 1268.

With continued reference to FIGS. 33 and 34, the lower platen assembly 1210 includes a cover holder 1300 fixedly coupled to the rails 1292. The support 1294 has a recessed region 1302 which receives the holder 1300. One or more fasteners (e.g., screws, nut and bolt assemblies, or the like), clamps, adhesives, or other types of couplers can couple the holder 1300 to the support 1294.

The roller mechanism 1244 includes a cam device 1250 and connectors 1252*a*, 1252*b*. The cam device 1250 includes a motor 1251 and a roller 1257 eccentrically mounted on a rotatable output shaft 1259 of the motor 1251, as shown in FIG. 34. The motor 1251 can rotate the roller 1257 about an axis of rotation 1253 to push a follower 1254 of the slide retaining device 1240. The motor 1251 can include, without limitation, a stepper motor, a drive motor, or other type of electrical motor.

Figure 35:
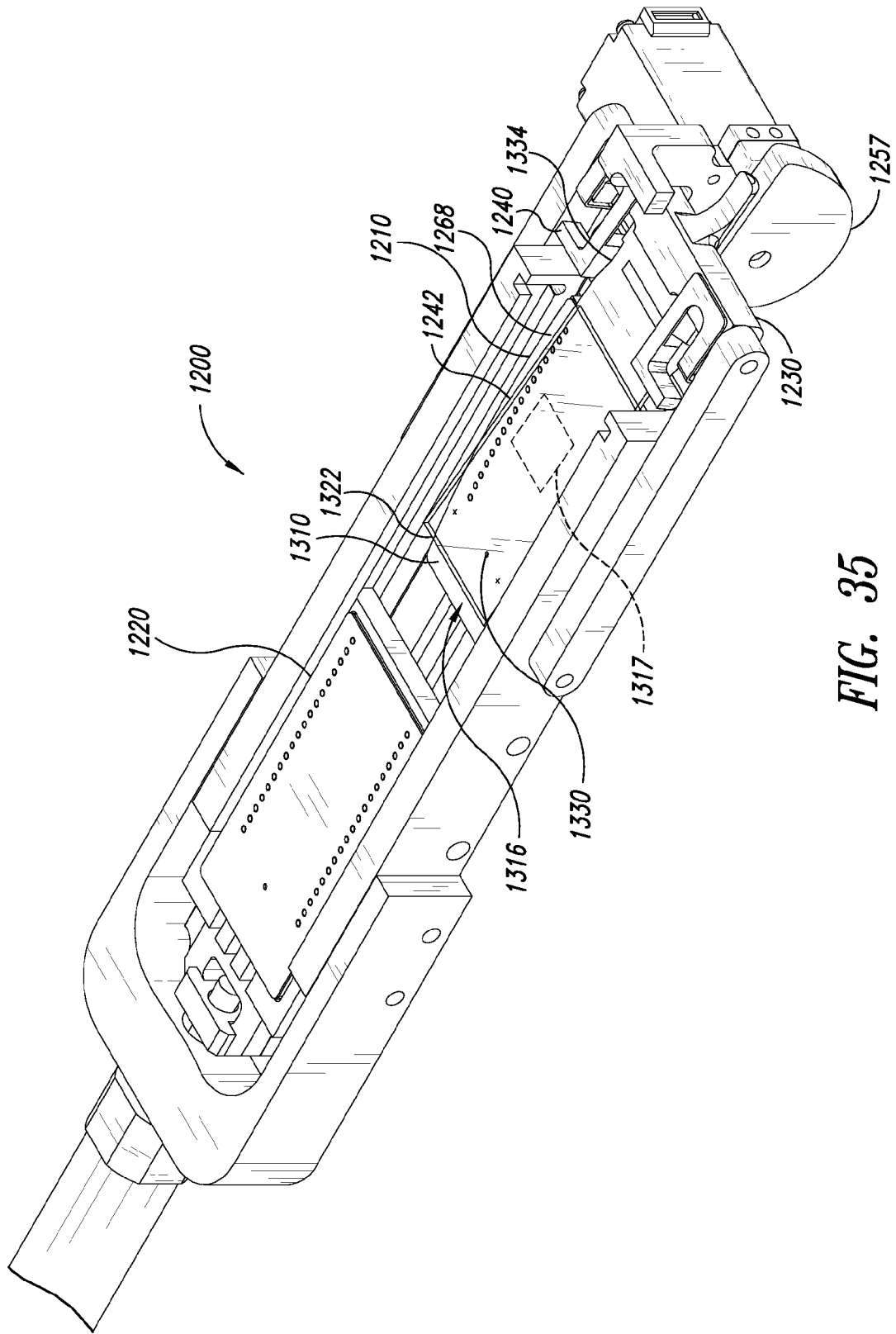
FIG. 35 is an isometric view of the slide processing station holding a microscope slide at an inclined orientation to form a gap between an end of the slide and a lower platen assembly.

FIGS. 35-44 show one method of processing the specimen 1317. The slide 1242 of FIG. 35 is generally aligned with an arcuate upper surface 1310 of the cover 1268 such that the slide 1242 is centered over a fluid application region 1316. Fluid can be delivered (e.g., manually delivered or via a fluid dispenser) onto the fluid application region 1316. To facilitate fluid delivery, the processing station 1200 can be in an inclined or upright orientation. A varying height gap between the slide 1242 and cover 1268 can accommodate the fluid without over-filling or under-filling. In some protocols, a fluid volume in a range of about 10 µl to about 100 µl can be dispensed and trapped under the slide 1242.

In a dynamic mode of operation, the slide 1242 is moved along the arcuate upper surface 1310. As the slide 1242 is moved back and forth, the fluid can be applied to the specimen 1317. In a static mode of operation, the slide 1242 can remain generally stationary with respect to the cover 1268.

Figure 36:
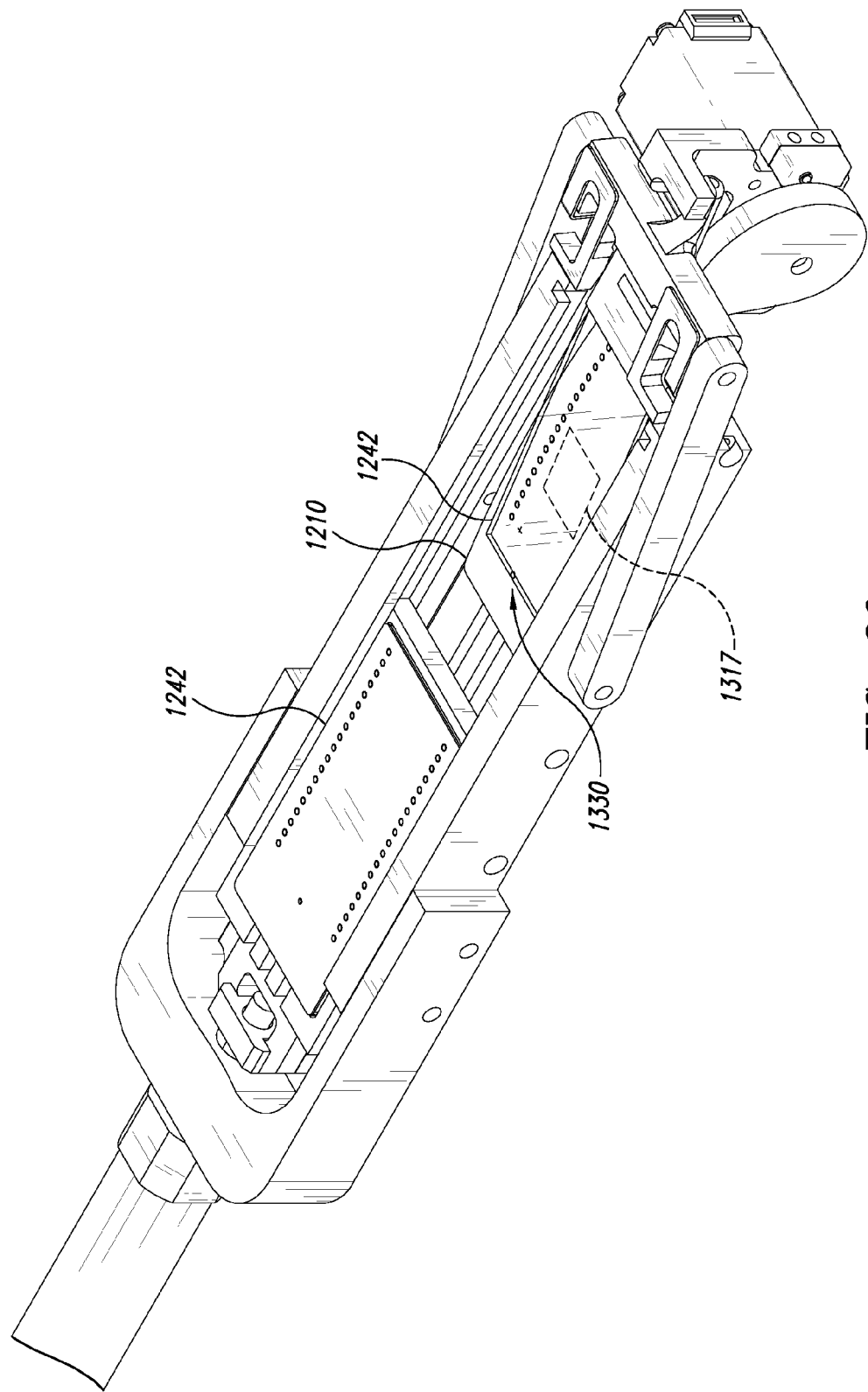
FIG. 36 is an isometric view of the slide positioned to urge waste towards a waste port of the lower platen assembly.

After the fluid is applied to the specimen 1317, the slide positioning device 1230 lifts an end on the slide 1242 to move the waste (e.g., unused liquid) towards a waste port 1330. In the illustrated embodiment, the roller 1257 can be rotated to move a slide end 1334 upwardly. As the slide 1242 tilts, the fluid is moved towards the waste port 1330. FIG. 36 shows the slide 1242 in an angled orientation to urge the waste towards the waste port 1330.

Figure 37:
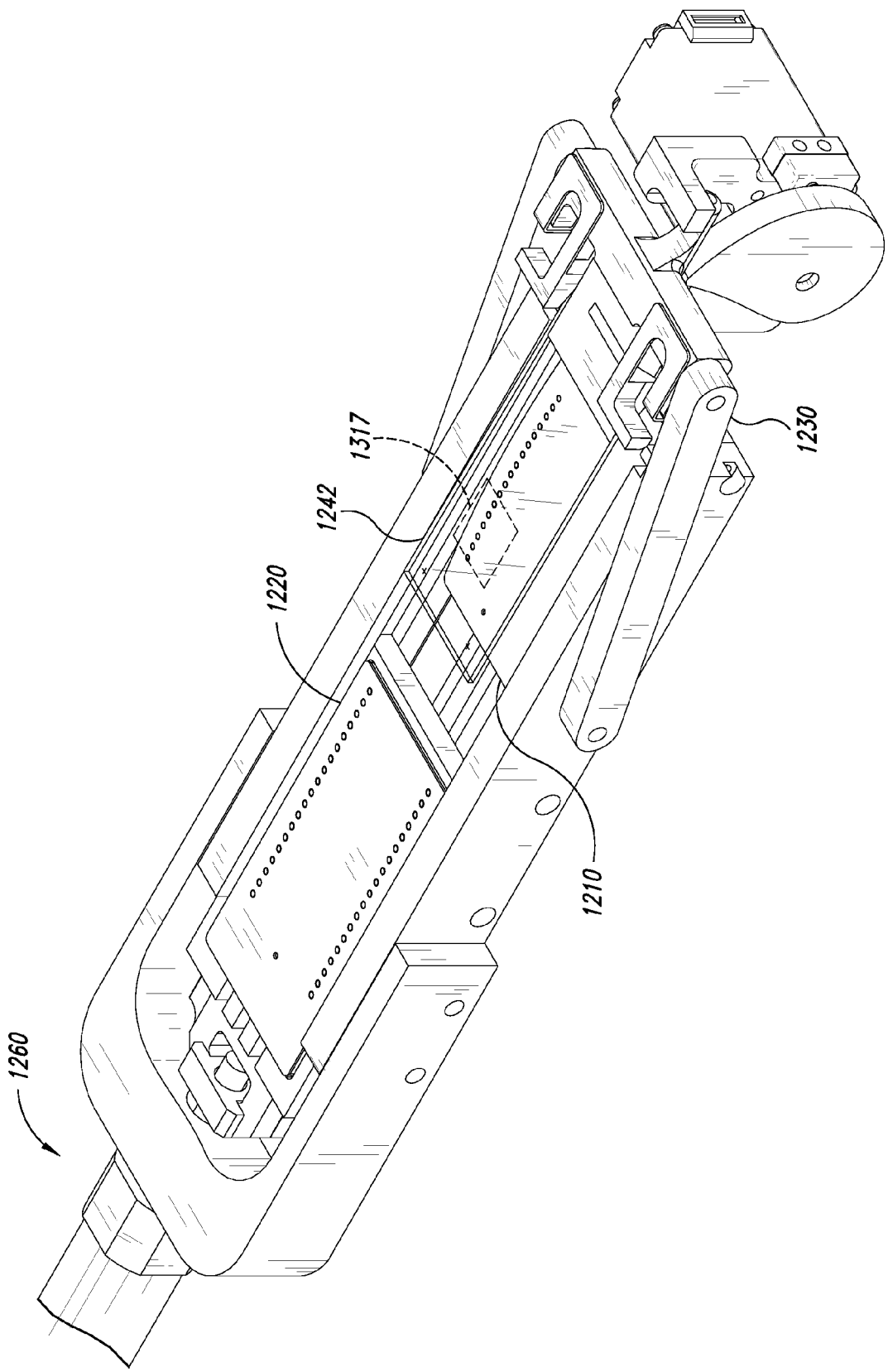
FIG. 37 is an isometric view of the slide held above the lower platen assembly.
Figure 39:
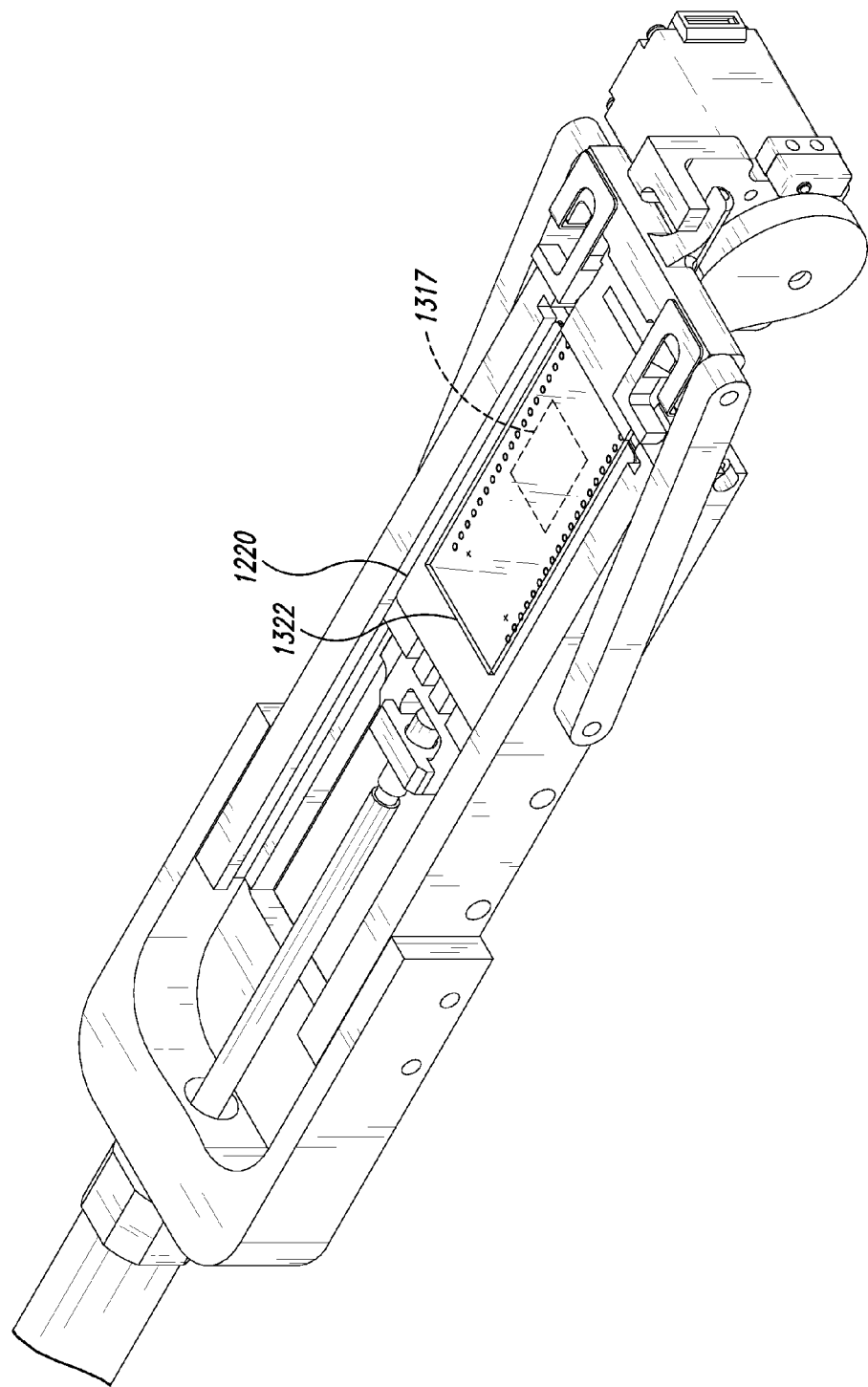
FIG. 39 is an isometric view of the slide laying flat on the upper platen assembly.

After removing used fluid, the slide positioning device 1230 can lift the slide 1242 of FIG. 36 away from the lower platen assembly 1210. FIG. 37 shows the generally horizontal slide 1242 in a raised position. The drive mechanism 1260 pushes the upper platen assembly 1220 underneath the raised slide 1242. After the upper platen assembly 1220 reaches the processing position of FIG. 38, the slide 1242 can be lowered onto the upper platen assembly 1220. FIG. 39 shows the slide 1242 resting on the upper platen assembly 1220.

Figure 40:
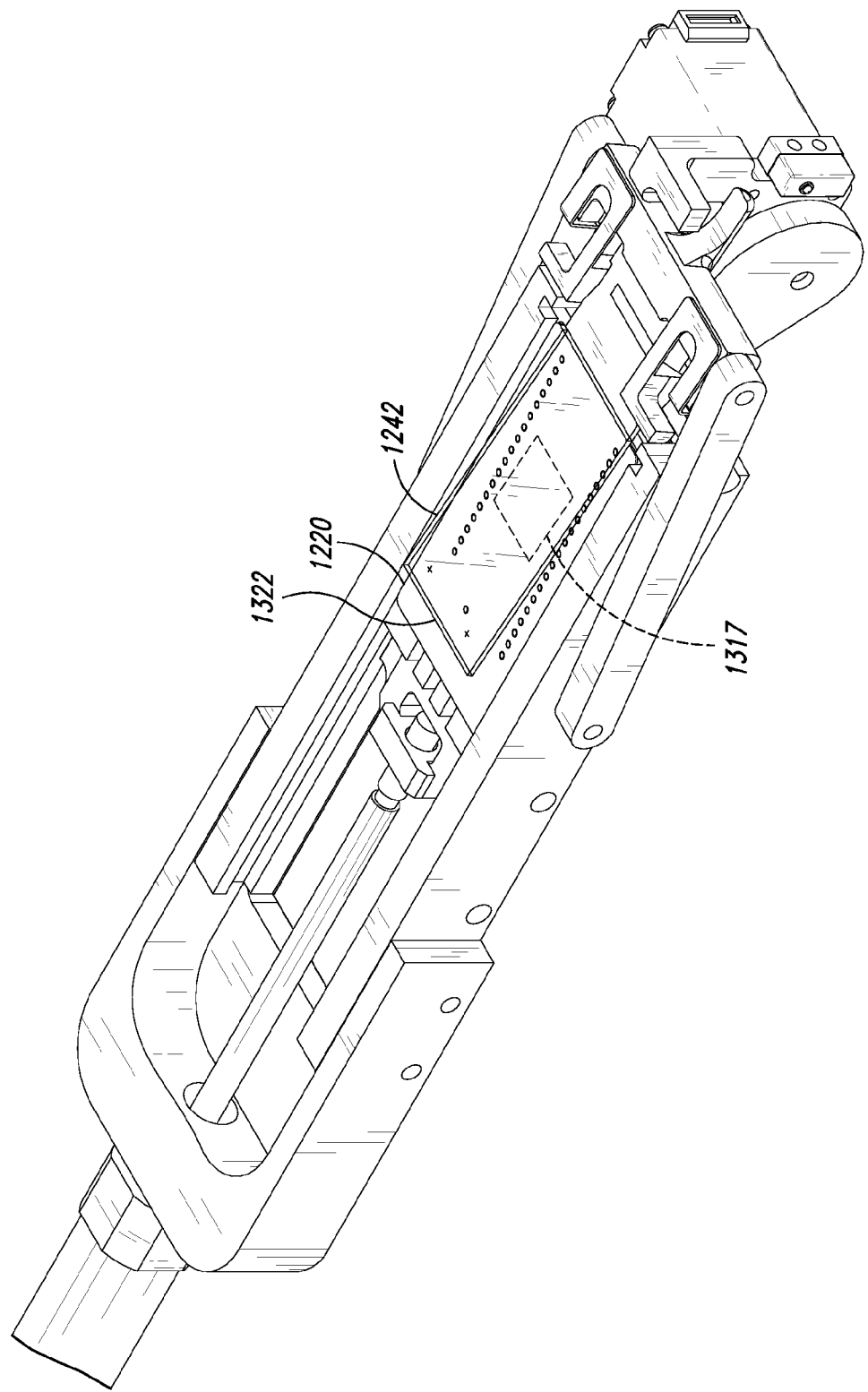
FIG. 40 is an isometric view of the slide positioned to allow delivery of fluid between the slide and the upper platen assembly.
Figure 41:
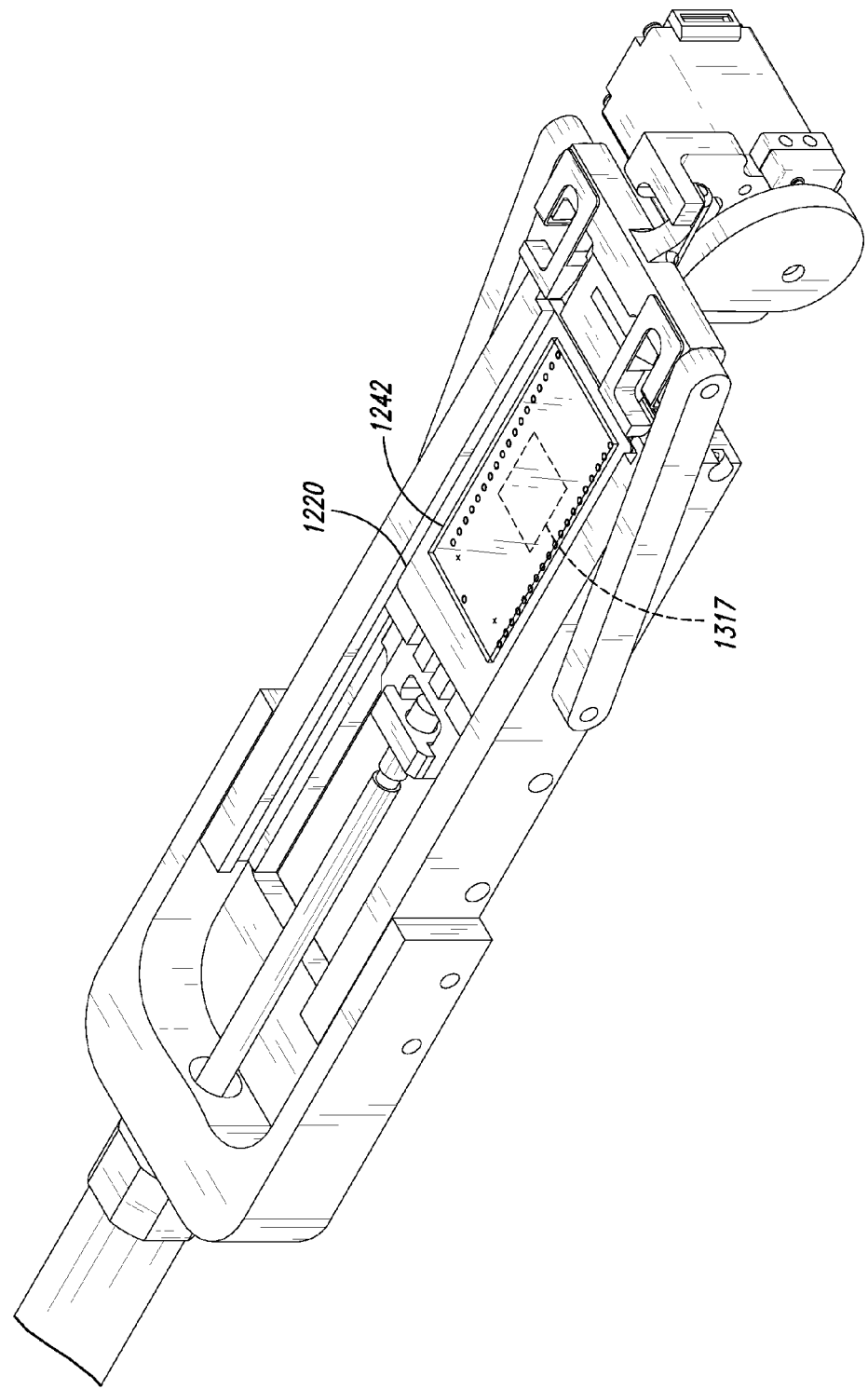
FIG. 41 is an isometric view of the slide resting on the upper platen assembly.
Figure 42:
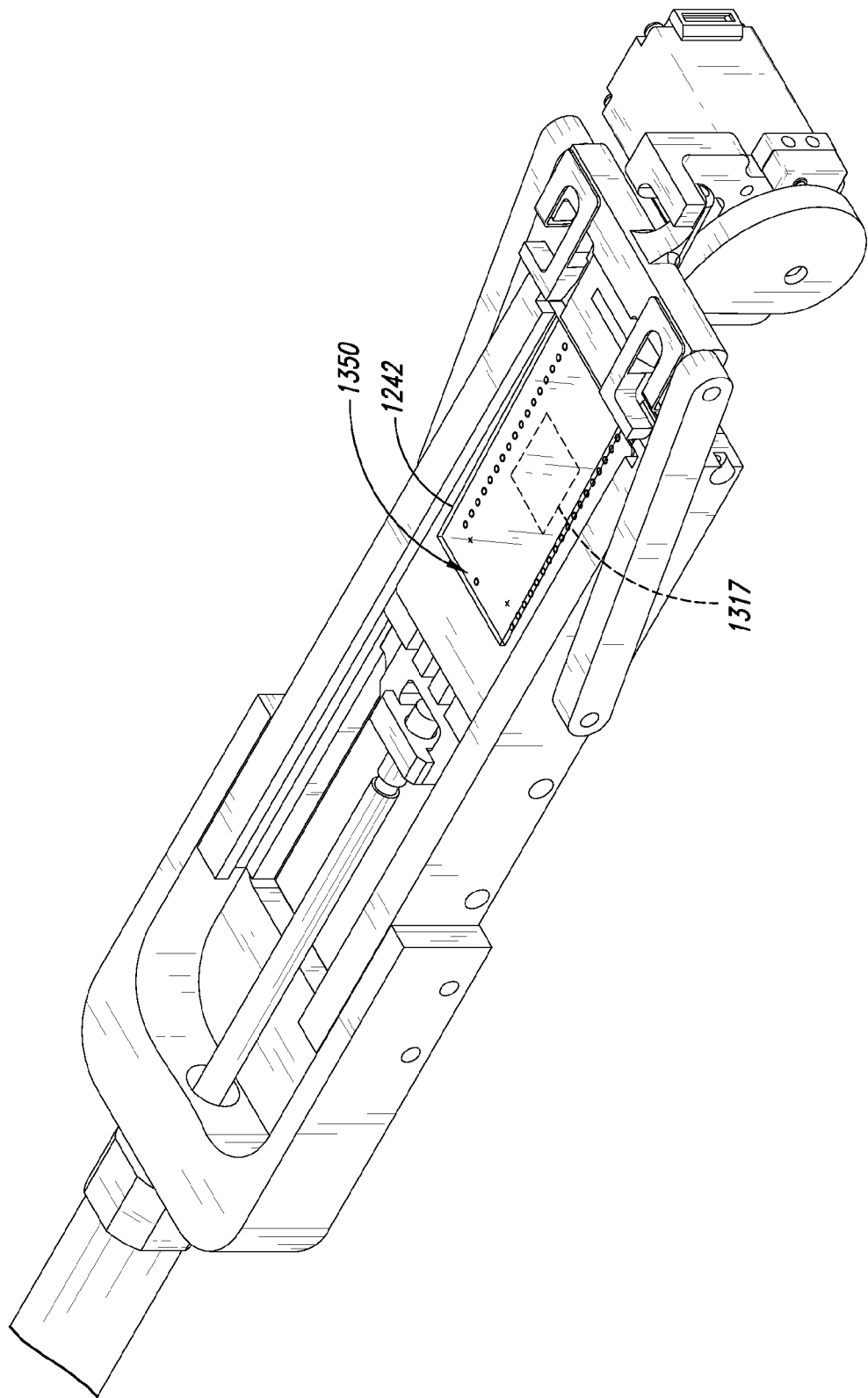
FIG. 42 is an isometric view of the slide positioned to urge waste towards a waste port.

An end 1322 of the slide 1242 can be lifted away from the upper platen assembly 1220 to deliver a substance onto the upper platen assembly 1220. FIG. 40 shows the end 1322 angled away from the upper platen assembly 1220. After fluid is introduced underneath the end 1322, the end 1322 can be lowered to spread the fluid underneath the slide 1242 via capillary action. To form a thin film, the slide 1242 can lay generally flat on the upper platen assembly 1220, as shown in FIG. 41. After a desired length of time, the slide 1242 can be tilted (see FIG. 42) to move the waste towards the waste port 1350. After the waste is aspirated, the slide 1242 can be lifted away from the upper platen assembly 1220.

Figure 43:
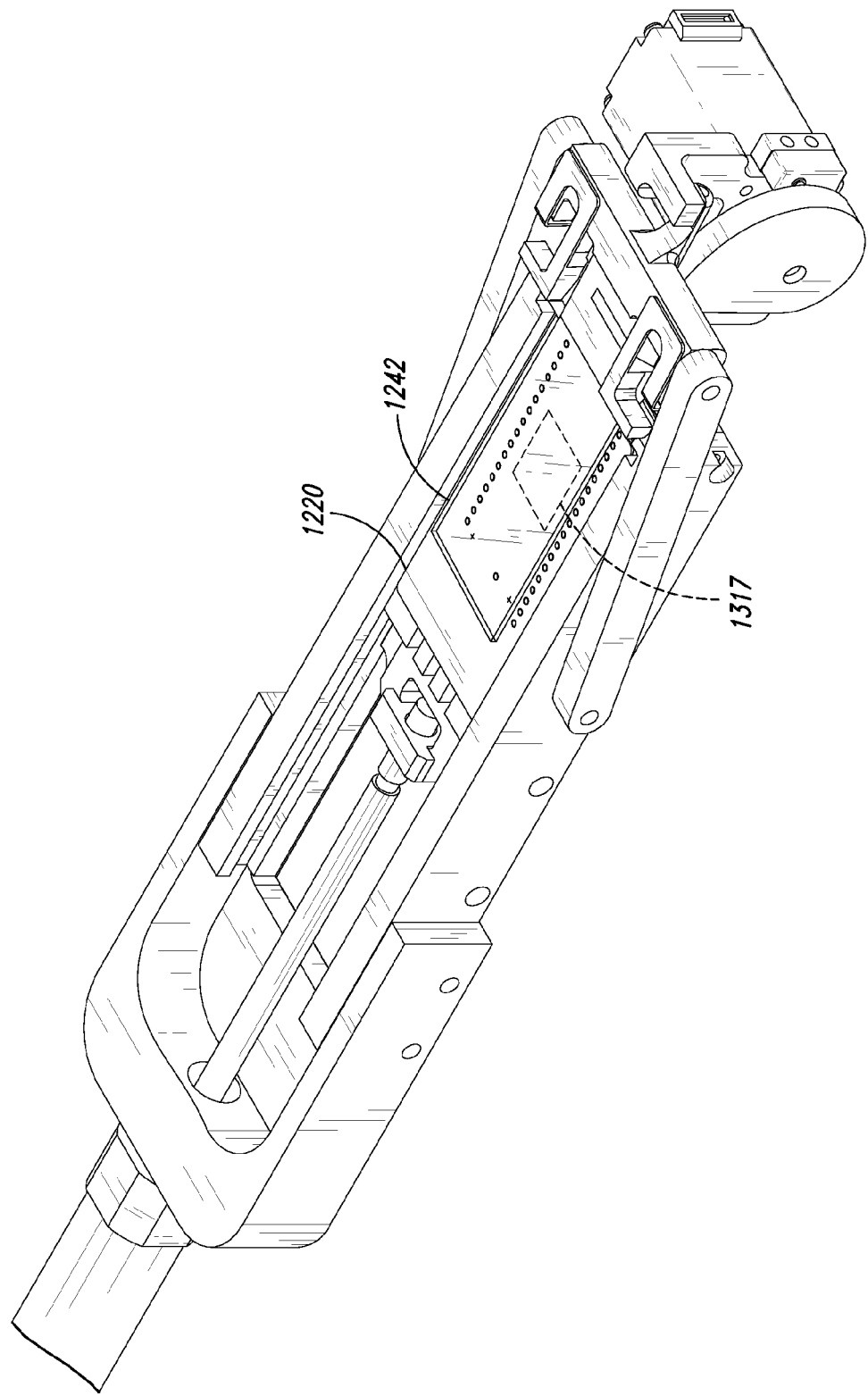
FIG. 43 is an isometric view of the slide held above the upper platen assembly.
Figure 44:
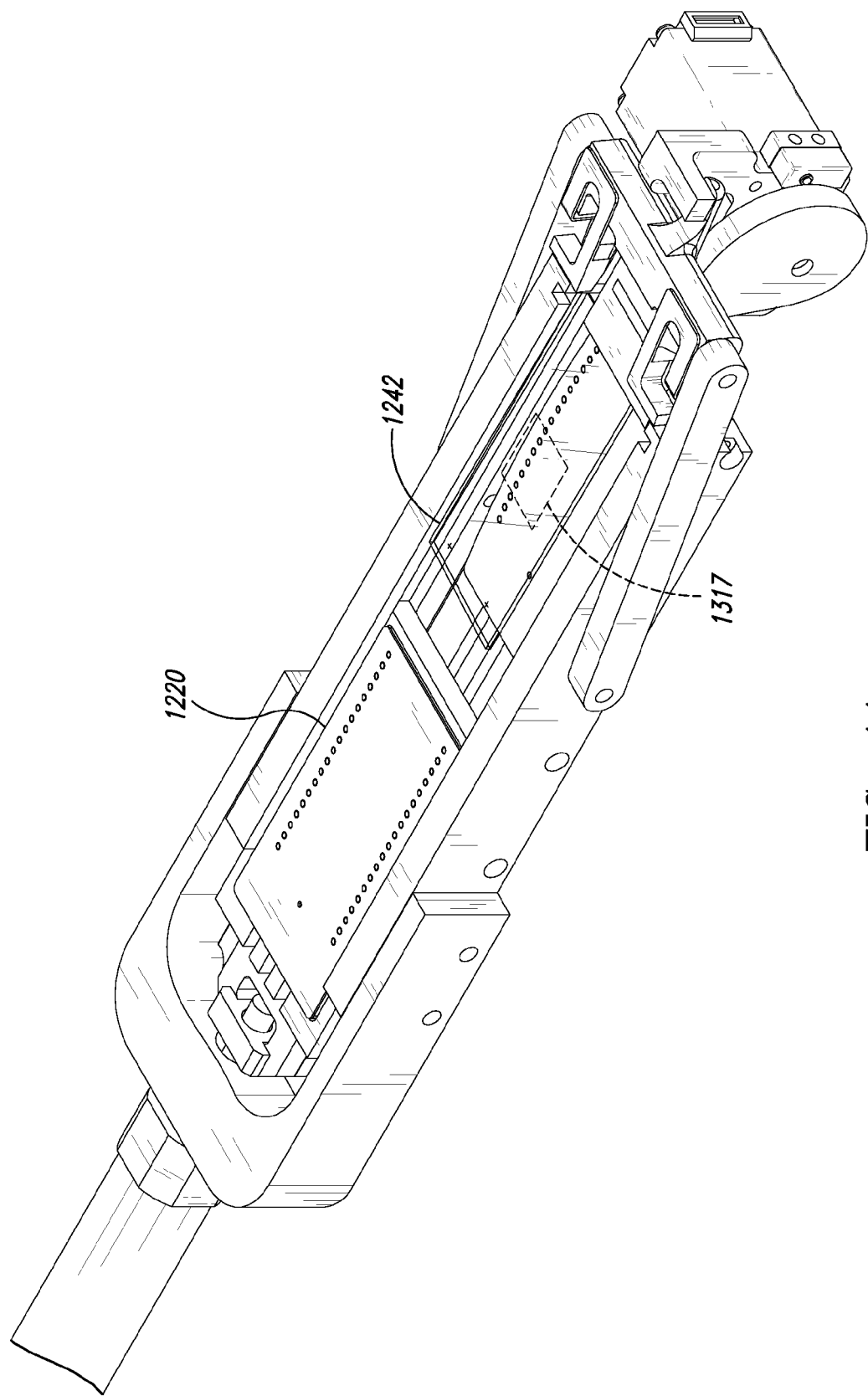
FIG. 44 is an isometric view of the upper platen assembly moved away from the slide.

FIG. 43 shows the slide 1242 positioned above the upper platen assembly 1220. The upper platen assembly 1220 can be moved back to the standby position, as shown in FIG. 44. The specimen 1317 can be processed again on the lower platen assembly 1210, if needed or desired.

The illustrated slide processing system 1200 has two platen assemblies. However, other embodiments can have any number of movable platen assemblies and stationary platen assemblies. For example, a slide processing station can have a plurality of movable platen assemblies such that each movable platen assembly can apply a different substance to prevent carryover. These platen assemblies can have flat configurations, non-planar configurations, or the like.

Figure 45:
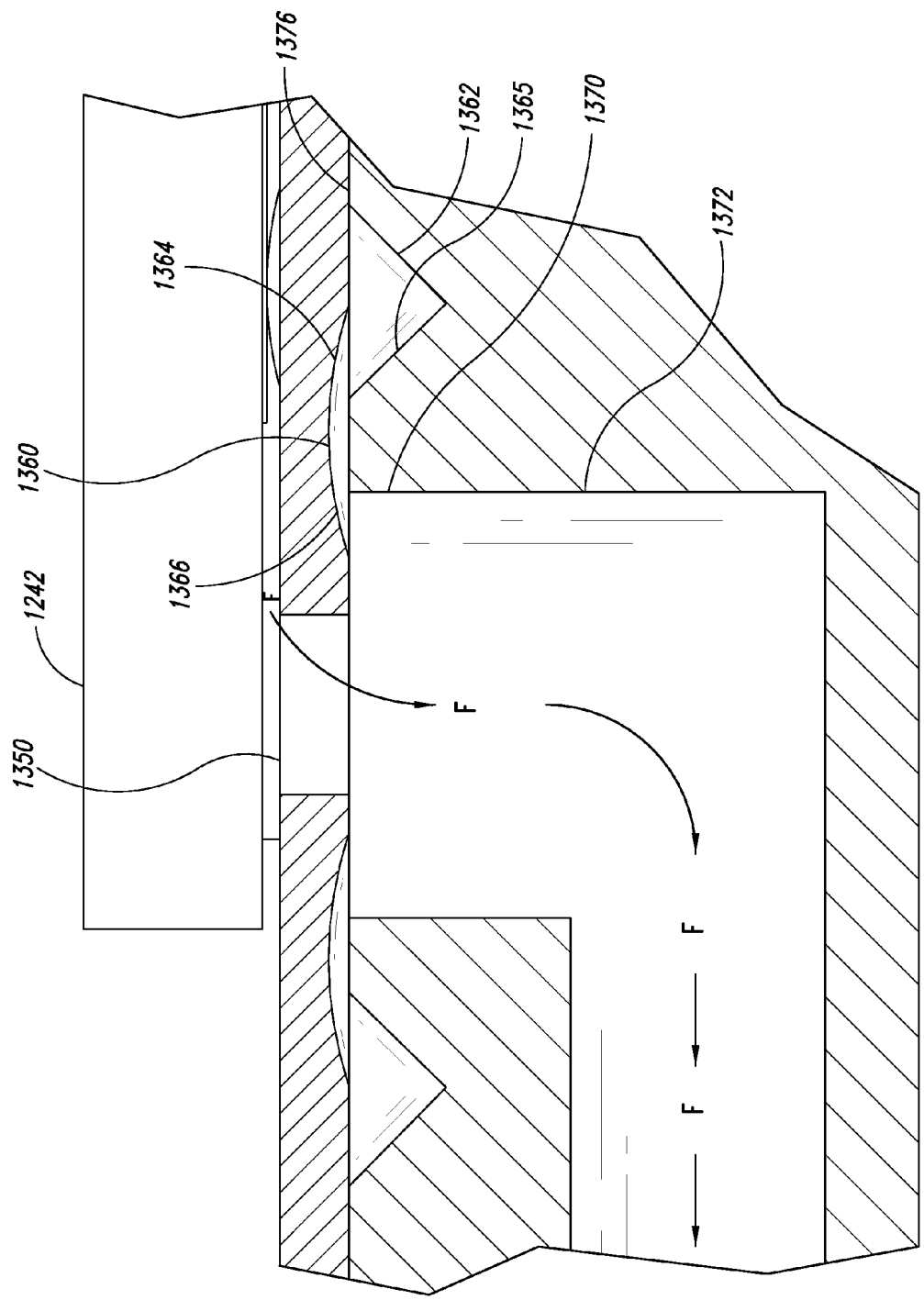
FIG. 45 is a detailed cross-sectional view of a portion of the slide processing station of FIG. 34.

FIG. 45 is a detailed view of flow inhibitors 1360, 1362. The partially overlapping flow inhibitors 1360, 1362 can minimize, limit, or substantially eliminate wicking and/or capillary action because a contact interface 1376 is positioned well away from the waste port 1350. The flow inhibitor 1360 is an annular U-shaped channel surrounding the waste port 1350. An outer portion 1364 of the flow inhibitor 1360 extends across an inner portion 1365 of the flow inhibitor 1362 (illustrated as a V-shaped channel). An inner portion 1366 of the flow inhibitor 1360 extends across at least a portion of an entrance 1370 of a waste passage 1372. The waste port 1350 can be generally concentric with the entrance 1370 to help guide waste (represented by fluid F) through the waste passage 1372. Even if the waste port 1350 becomes slightly misaligned with the entrance 1370, the waste still flow through the waste port 1350 into the entrance 1370.

Figure 46:
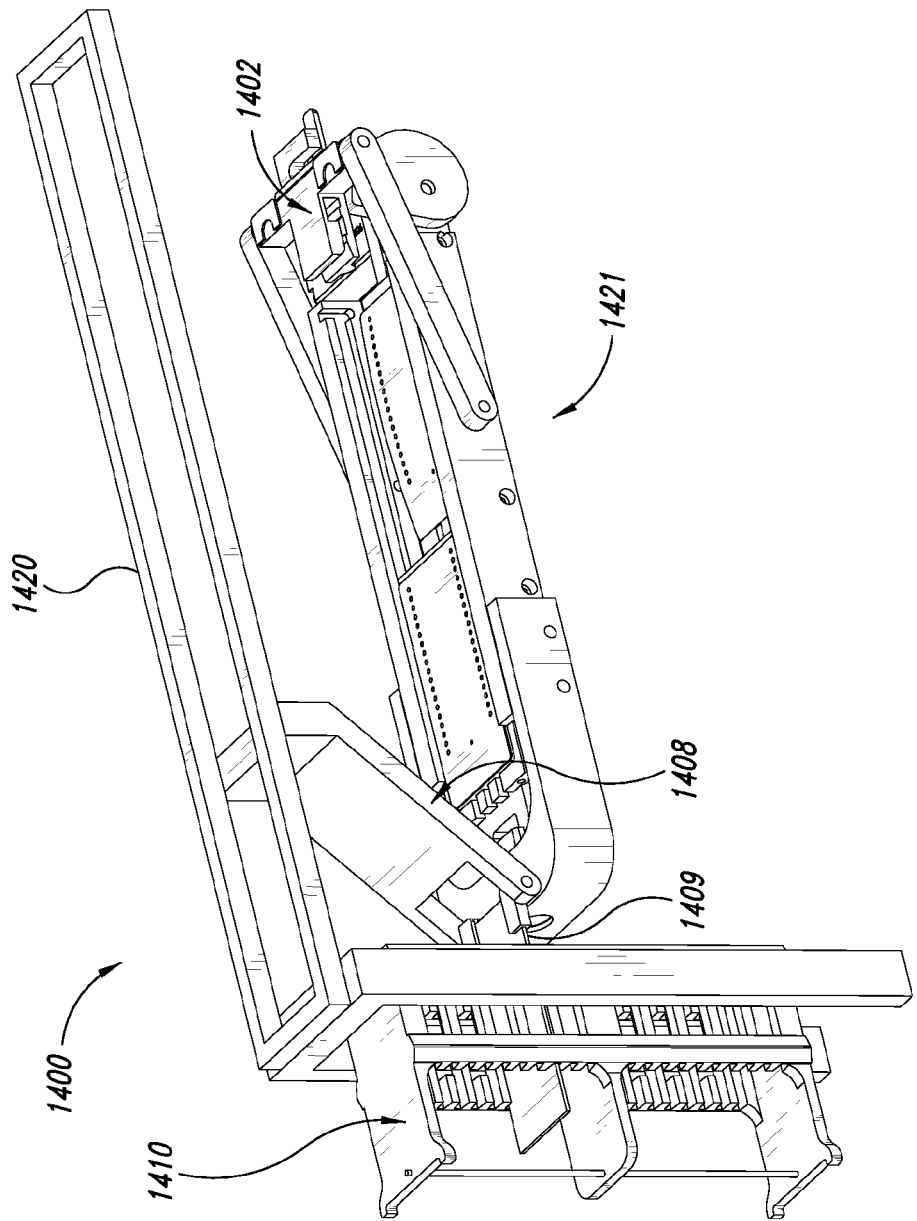
FIG. 46 is an isometric view of a conveyor for transporting microscope slides between a slide rack and a slide processing station.
Figure 47:
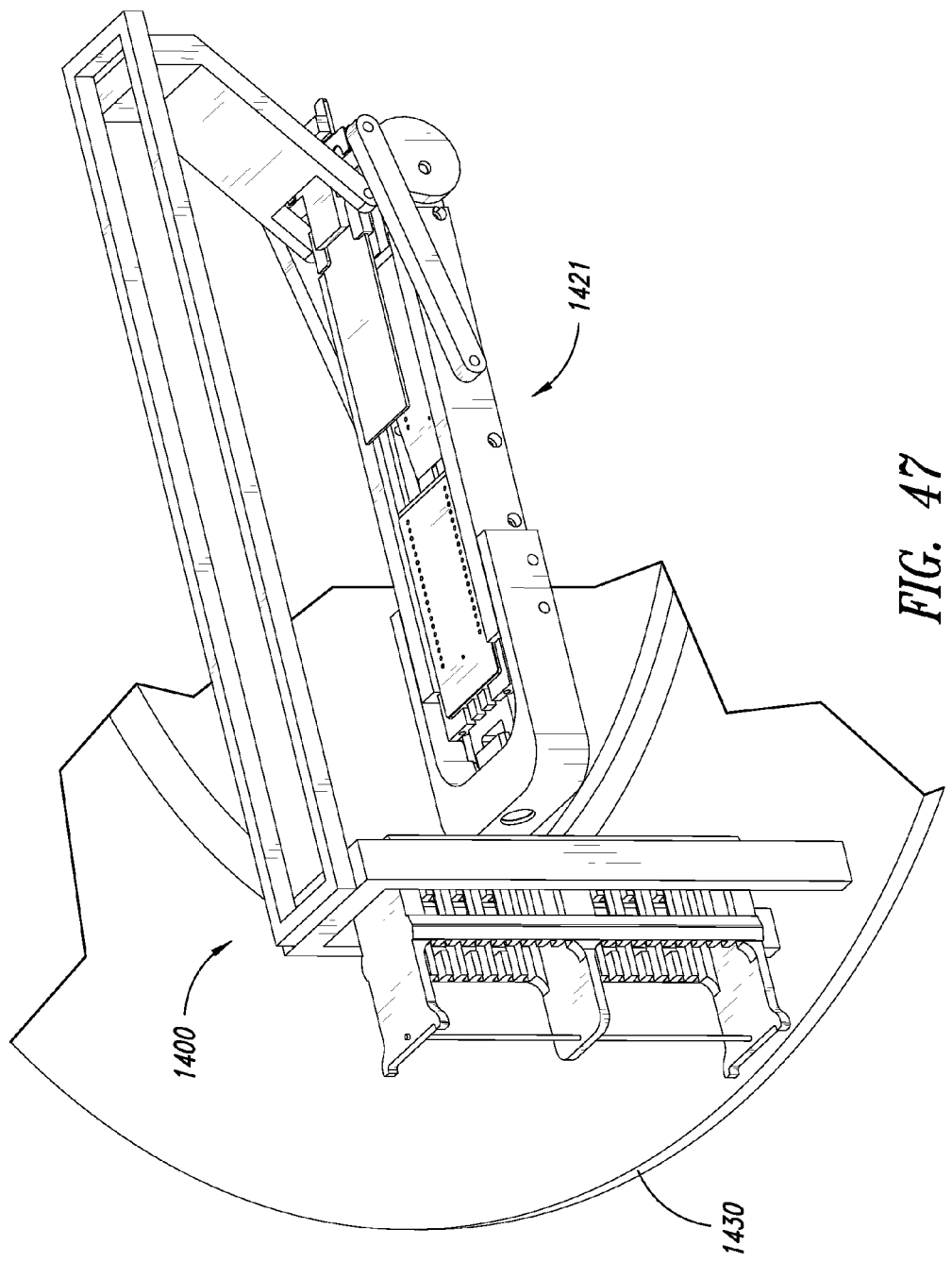
FIG. 47 is an isometric view of the conveyer of FIG. 46 loading a microscope slide into the slide processing station.

Referring to FIG. 46, a loading apparatus 1400 is configured to load and unload a slide retaining device 1402 of a processing station 1421. The loading apparatus 1400 includes a gripper 1408 that takes a slide 1409 from a rack 1410 with vertically spaced shelves. The gripper 1408 moves along a rail 1420 to insert the slide 1409 into the slide retaining device 1402, as shown in FIG. 47. To unload the processing station 1421, the gripper 1408 can be slid over the end of the slide 1409. The gripper 1208 pulls the slide 1409 away from the slide retaining device 1402. In this manner, the loading apparatus 1400 can both load and unload microscope slides.

A positioning wheel 1430 of FIGS. 46 and 47 can rotate to position the loading apparatus 1400 next to processing stations. In other embodiments, each processing station can have a dedicated loading apparatus to avoid wait times.

Figure 48:
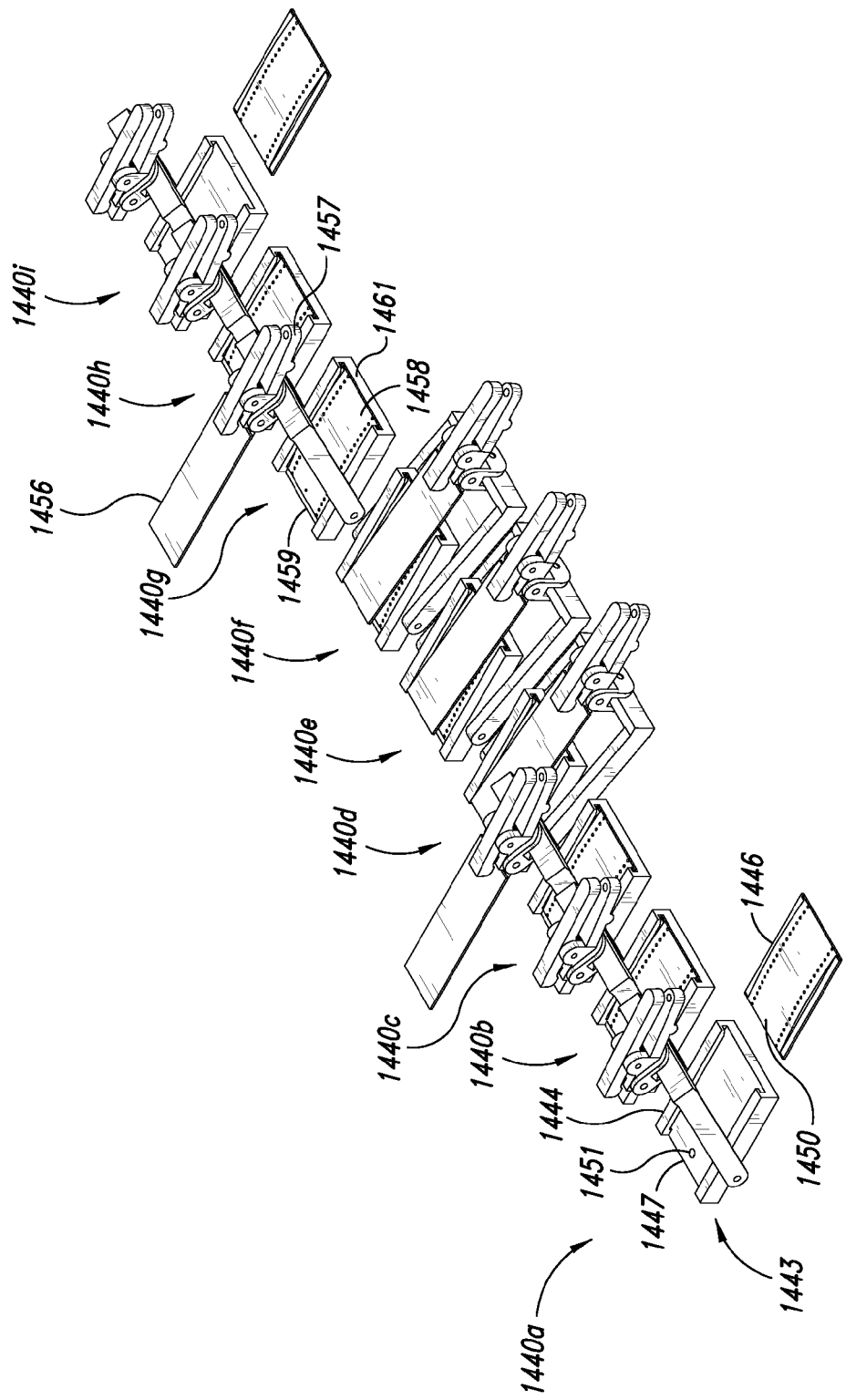
FIG. 48 is an isometric view of slide processing stations, in accordance with one embodiment.

FIG. 48 shows slide processing stations 1440a-i (collectively "1440"). The description of one of the processing stations 1440 can apply equally to the others, unless indicated otherwise.

The processing station 1440a includes a platen assembly 1443 including a cover holder 1444 and a cover 1446 shown spaced apart from the holder 1444. The cover 1446 is in the form of a generally rigid tile that can be placed in a channel 1447 of the holder 1444. A waste port 1450 can be aligned with a waste entrance 1451 in the holder 1444. The tile 1446 can be installed (e.g., manually or automatically) for dynamic processing and uninstalled for static processing.

The processing station 1440g of FIG. 48 is ready to dynamically process a microscope slide 1456. A slide positioning device 1457 holding the slide 1456 in a cantilevered fashion can use an arcuate upper surface 1458 of a tile 1459 to apply a liquid to a specimen carried on a lower face of the slide 1456. To perform static processing, the tile 1459 can be removed, and the positioning device 1457 can lower the slide 1456 onto a generally flat upper surface of a cover holder 1461.

The tiles of FIG. 48 can be replaced to change the curvature of the surface used to apply the liquid, to adjust the sizes and configurations of gapping elements, or the like. Based on a given protocol to be performed, the user can select and load an appropriate tile for processing.

Figure 49:
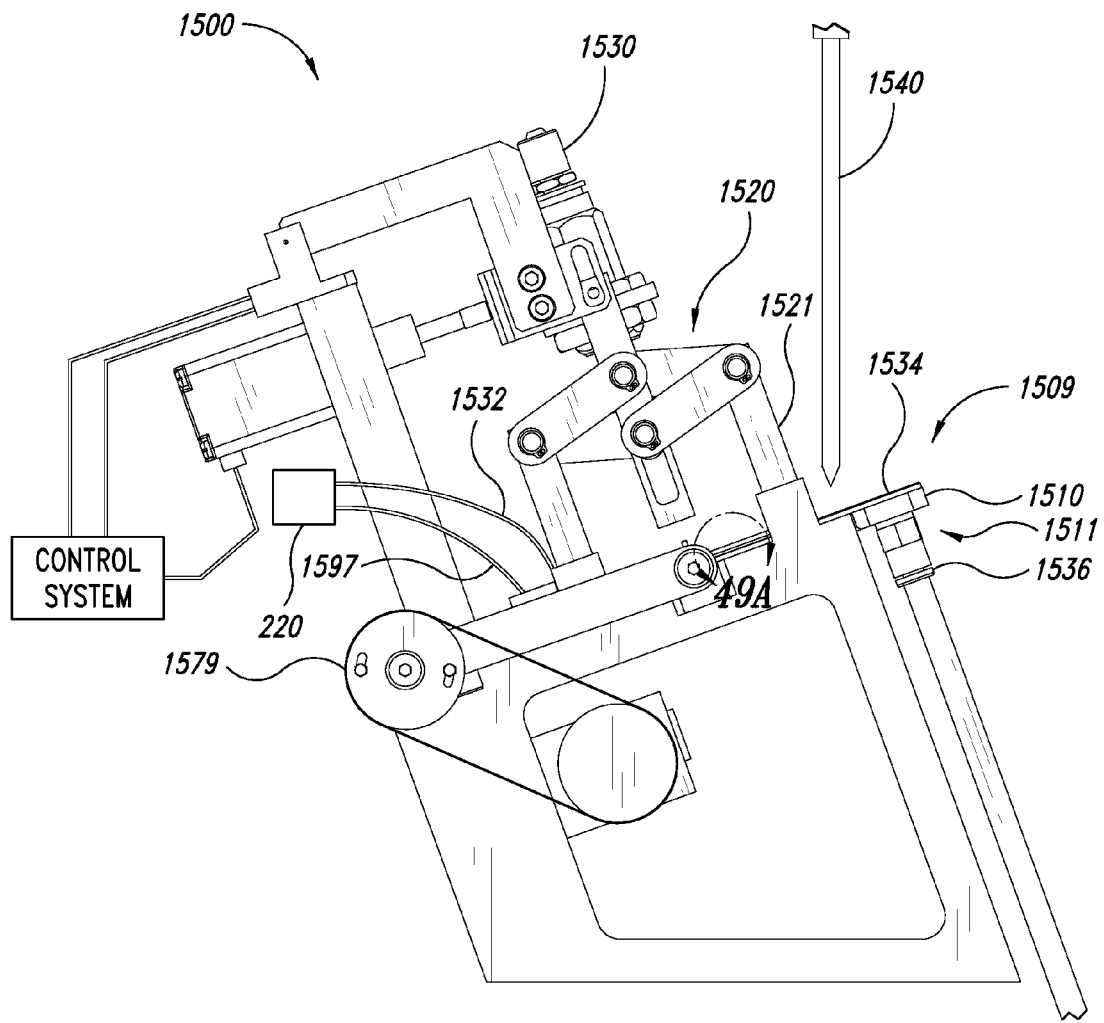
FIG. 49 is a side elevational view of a slide processing station and a fluid dispenser ready to dispense fluid onto a microscope slide.
Figure 49A:
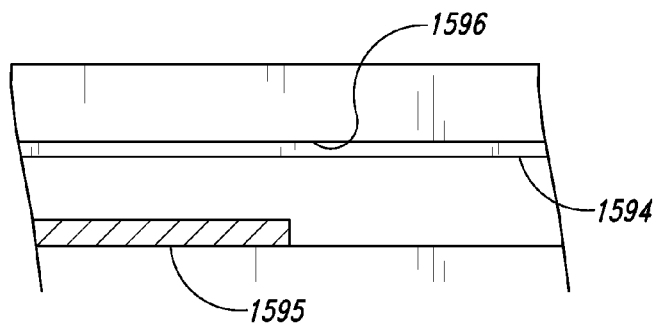
FIG. 49A is a detailed view of a portion of the slide processing station of FIG. 49.

FIGS. 49 and 49A shows an automated processing system 1500 including a platen assembly 1509, a roller unit 1520, and a drive mechanism 1530. A fluid dispenser 1540 can deliver a fluid onto a slide 1534 held by a slide positioning device 1510 of the platen assembly 1509. The roller unit 1520 can assume different configurations to process a specimen 1595 on the slide 1534. Waste can be removed via a waste line 1532. Samples can be rapidly processed without problems associated with manual processing.

Figure 50:
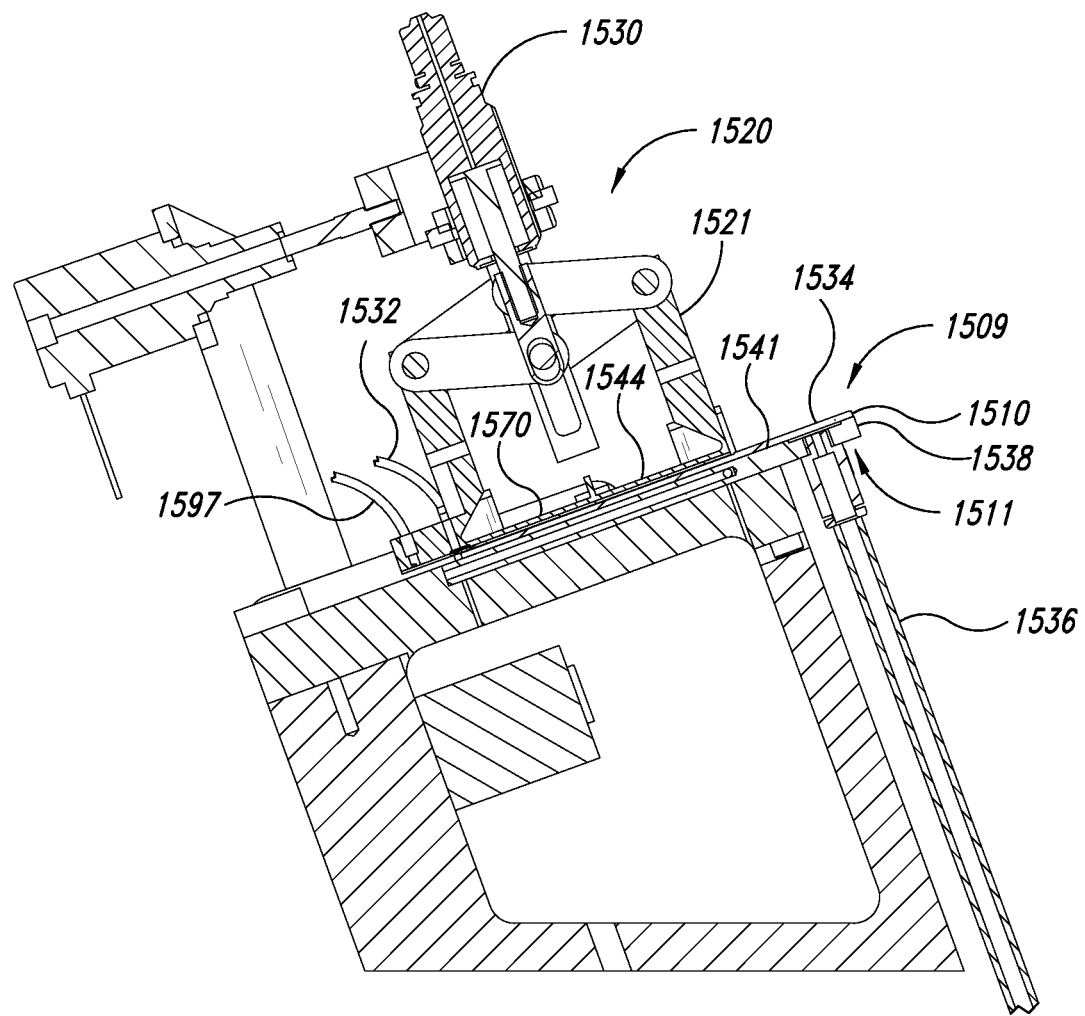
FIG. 50 is a side cross-sectional view of the slide processing station of FIG. 49.

Referring to FIG. 50, the slide positioning device 1510 can include a slide retaining device 1511 with a main body 1538 connected to a line 1536. When a vacuum is applied via the line 1536, the slide 1534 can be securely held against an upper surface 1541 of the main body 1538. The main body 1538 can include a network of passageways, throughholes, channels, or any other features suitable for applying a vacuum. In some embodiments, the slide retaining device 1511 includes a mechanical chuck and can include one or more clamps, adhesive layers, mechanical fasteners (e.g., clamps), or the like capable of selectively holding and releasing the slide 1534. Other types of slide holders can also be used. For example, the slide retaining device 1511 can be an electrostatic chuck.

Figure 51:
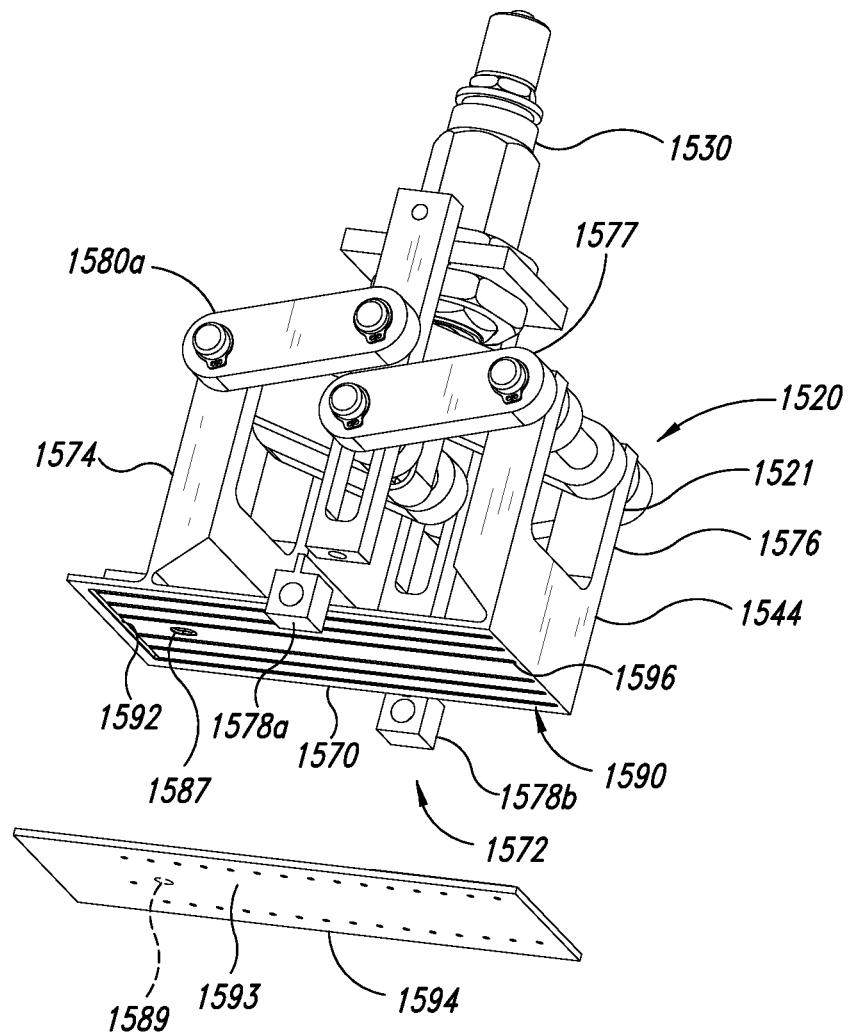
FIG. 51 is an isometric view of a convertible mechanism and a cover spaced apart from the convertible mechanism.
Figure 52:
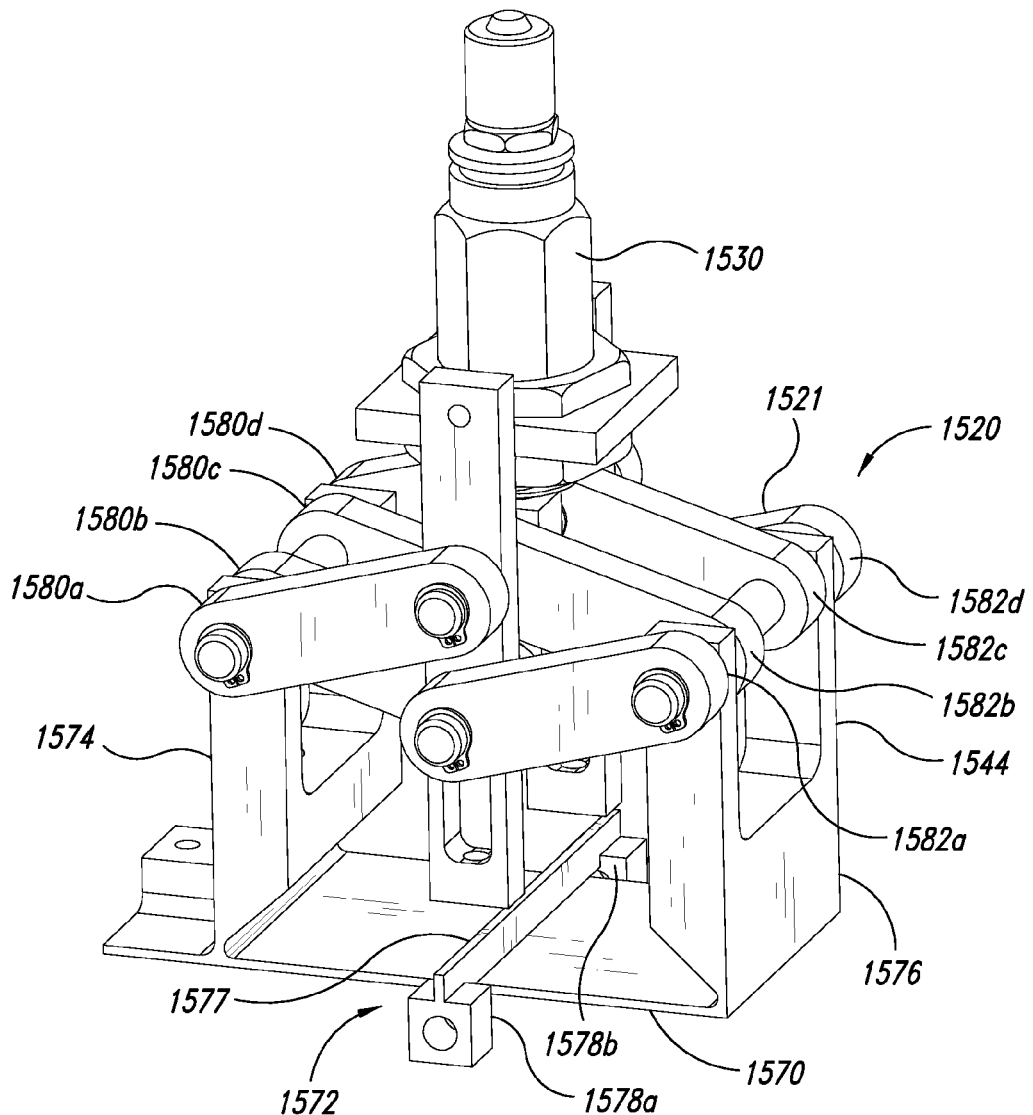
FIG. 52 is another isometric view of the convertible mechanism and the cover of FIG. 51.
Figure 52:
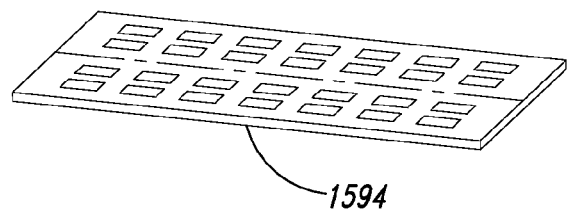
Figure 53:
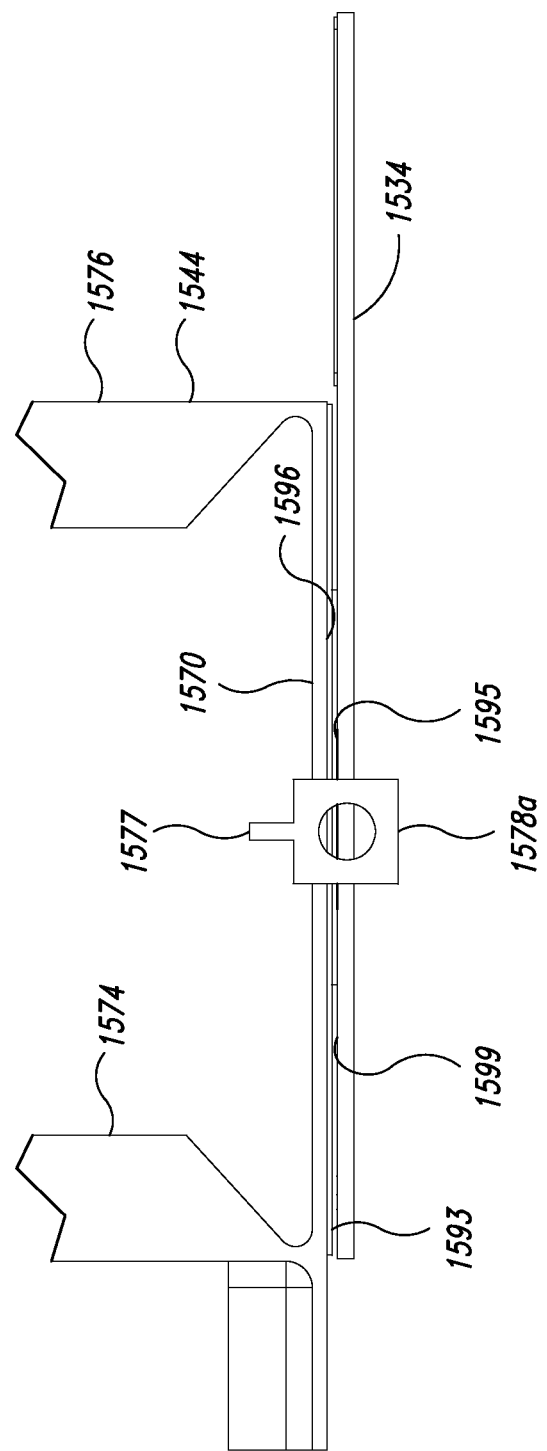
FIG. 53 is a front elevational view of a deformable applicator.

The roller unit 1520 of FIGS. 51 and 52 includes a platen assembly 1521 including a converting device 1577 and a deformable applicator 1544 movable between different configurations, including, without limitation, a substantially flat configuration (shown in FIGS. 51-53), a curved configuration (shown in FIG. 54), or any other suitable configuration. For dynamic processing, the deformable applicator 1544 can be in the curved configuration such that a cover 1594 is also in a curved configuration. For static processing, the deformable applicator 1544 can be in the substantially flat configuration such that the cover 1594 lays flat on the slide 1534. After the cover 1594 is used, it can be discarded or reused.

The deformable applicator 1544 can include a bendable member 1570 extending between two support members 1574, 1576 and a bracket 1572 physically connected to the bendable member 1570. Connectors 1580a-d are pivotally coupled to the support member 1574 of FIG. 52, and connectors 1582a-d are pivotally coupled to the support member 1576. The bracket 1572 includes a first member 1578a, a second member 1578b, and an elongate member 1577 extending between the first and second members 1578a, 1578b.

The bendable member 1570 can be made, in whole or in part, of metal (e.g., steel, aluminum, titanium, or the like), composites, plastics, or other resilient materials capable of undergoing relatively large elastic deformations. The bracket 1572 can be welded or otherwise coupled to the bendable member 1570.

As shown in FIG. 51, an outer face 1596 of the bendable member 1570 includes a network of channels 1590 and a vacuum port 1592. When the cover 1594 overlays the outer face 1596, a vacuum can be applied via the channels 1590 to hold the cover 1594. A vacuum line 1597 in FIG. 50 is in fluid communication with the channels 1590 and can apply the vacuum.

Figure 54:
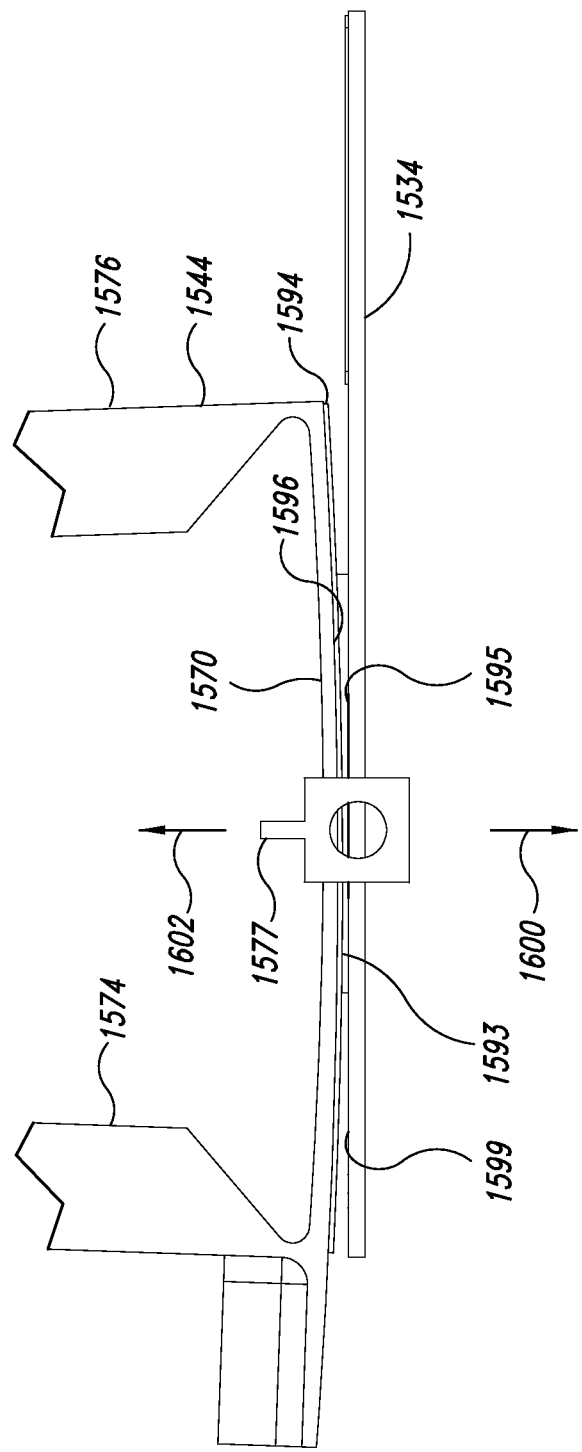
FIG. 54 is a side elevational view of a deformable application in a curved configuration.
Figure 55:
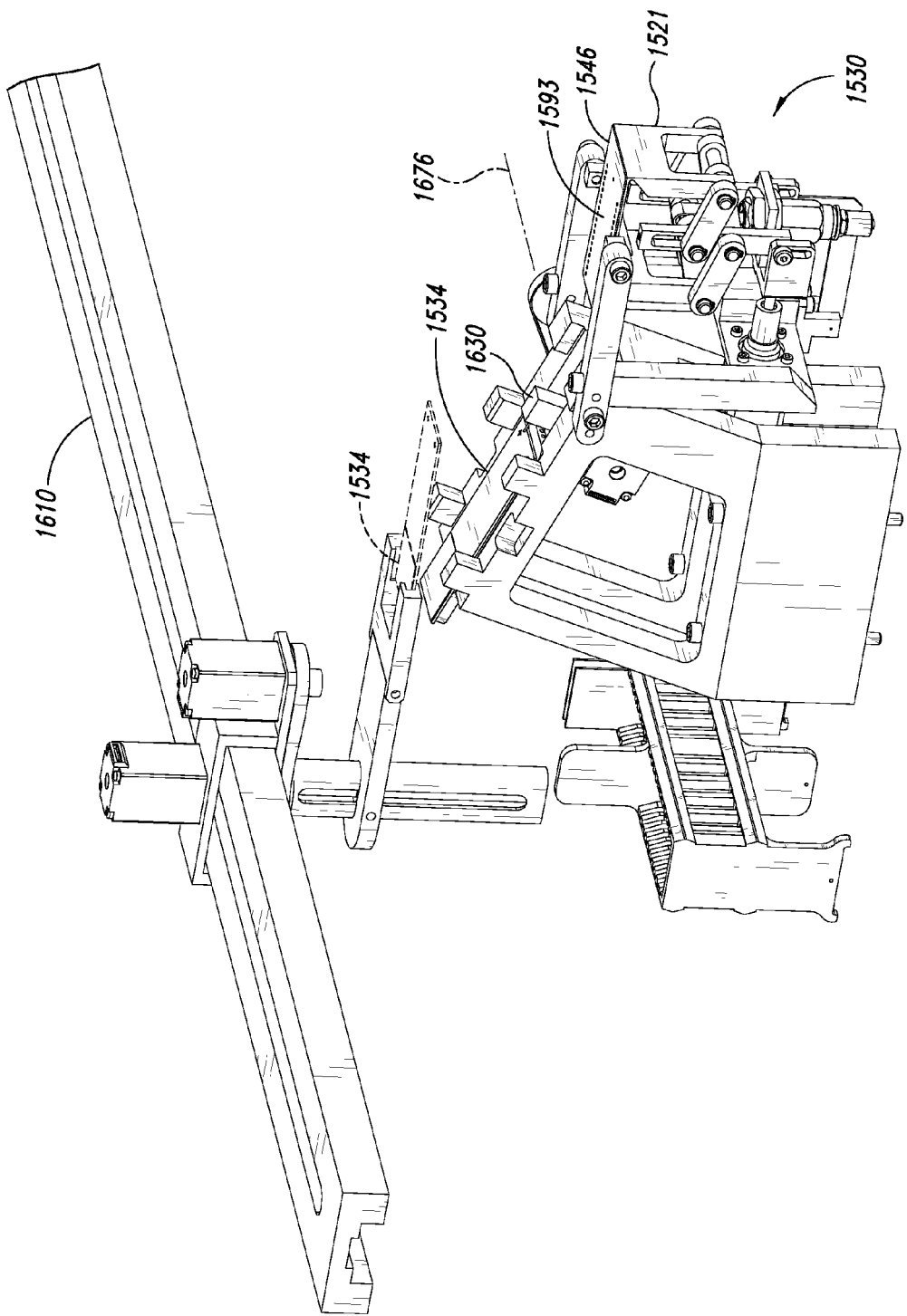
FIG. 55 is an isometric view of a slide processing station in an open position.

A drive 1579 of FIG. 49 is coupled to the bendable member 1570 via the members 1578a, 1578b, such that when the drive 1579 rotates, the middle of the bendable member 1570 bends downwardly or upwardly. FIG. 54 shows the bendable member 1570 with the face 1596 in a convex configuration by moving the first and second members 1578a, 1578b downwardly, as indicated by an arrow 1600 (FIG. 54). The cover 1594 has a curvature that generally matches the curvature of the face 1596. The convex face 1596 and the curved cover 1594 can roll together along the slide 1534. FIG. 55 shows the face 1596 in a concave configuration by moving the center of the bendable member 1570 away from the slide 1534, as indicated by an arrow 1602 (FIG. 54). The concave cover 1594 can cooperate with the slide 1534 to provide effective enchambering of a specimen 1595 using reagent 1599.

The processing system 1500 can be moved from a closed configuration (FIG. 50) to an open configuration (FIG. 55) to remove the used cover 1594 and/or the slide 1534. When the processing system 1500 is in the closed configuration, the platen assembly 1521 is in a processing position. When the processing system 1500 is in the open configuration, the platen assembly 1521 is in a standby position. An illustrated transporter 1610 of FIG. 55 can load and unload covers and/or slides. To move the processing system 1500 to the standby position, the drive mechanism 1530 can be rotated about an axis of rotation 1676 from the processing position to the standby position. After loading a slide, the drive mechanism 1530 can be rotated about the axis of rotation 1676 to the closed position.

Figure 56:
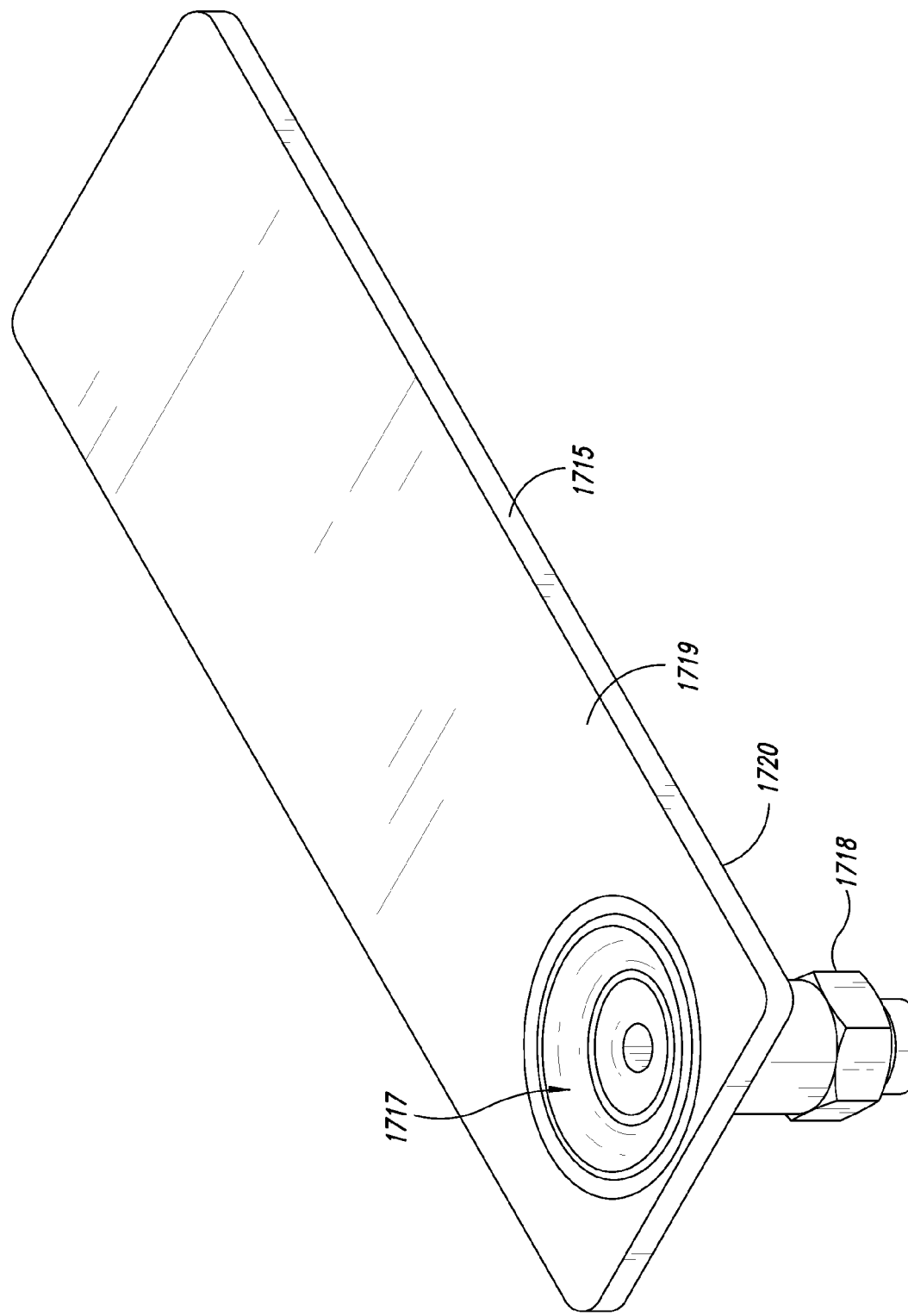
FIG. 56 is an isometric view of a slide holder, in accordance with one embodiment.
Figure 57:
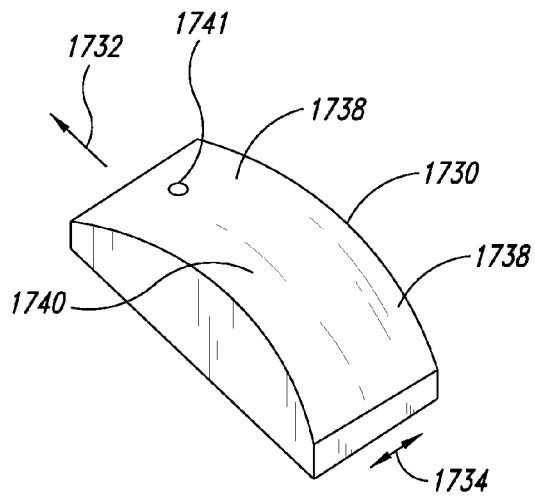
FIG. 57 is an isometric view of a saddle-shaped opposable.

FIG. 56 shows the positioning device 1510 in the form of a vacuum slide chuck or holder that includes a main body 1715 and a port 1717. A vacuum line can be coupled to a connector 1718. A vacuum can be drawn to hold the slide against a face 1719 of the main body 1715. The main body 1715 can include one or more thermal elements for controlling the slide temperature. Alternatively, one or more thermal elements can be coupled to a backside 1720 of the main body 1715.

To process a specimen, the dispenser 1540 of FIG. 49, illustrated in the form of a pipette, delivers a wash fluid onto the slide 1534. The wash fluid can be removed to apply a reagent. The roller unit 1520 can be moved to an open or standby configuration. The dispenser 1540 moves above the slide 1534 (e.g., above the middle of the slide 1734) and dispenses a reagent onto the slide 1534. The roller unit 1520 closes to begin incubation at the desired volume, roll distance, temperature, and CPM (speed). The roller unit 1520 can periodically roll (e.g., longitudinally, laterally, or both) to agitate the reagent. In some protocols, longitudinal or transverse rolling movement (e.g., longitudinal rolling movements and/or transverse rolling movements) of the specimen facing surface 1593 (FIG. 51) of the platen assembly 1521 relative to the retained slide 1534 can create a varying height gap. The drive mechanism 1530 can include, without limitation, one or more linear actuators, piston assemblies, cam mechanisms, motors, solenoids, and/or other components suitable for providing the desired movement of the cover 1594. On-slide-mixing can also be performed, if needed or desired. At the end of reagent incubation, the reagent is removed after moving the roller unit 1520 to an open position. The wash fluid is dispensed from a bulk dispenser to wash the slide 1534. The roller unit 1520 closes and begins the wash cycle.

The cover 1594 can include a waste port 1589 (shown in FIG. 51 in phantom line) that can mate with a waste passage or port 1587 to define a fluid path. The waste line 1532 (FIGS. 49 and 50) can draw waste substances away from the slide 1534 via the ports 1589, 1587. An optional device 1630 (see FIG. 55) can function as a waste remover to remove substances from the slide 1534. The device 1630 can operate similar to the waste remover 130 discussed in connection with FIGS. 7-13. In some protocols, waste substances are removed using both the waste line 1532 and the waste remover 1630. Additionally or alternatively, the device 1630 can serve as a liquid dispenser.

The roller unit 1520 can include other types of platen assemblies, including the platen assembly 180 (see FIG. 7), the platen assembly 361 (see FIG. 16), the platen assembly 1210 (see FIG. 33), the platen assembly 1220 (see FIG. 33), and the platen assembly 1443 (see FIG. 48). Components of the platen assemblies (e.g., bases, covers, etc.) can be mixed and matched based on the desired processing capabilities. Compliant, semi-compliant, and rigid covers or other types of components can be employed with the different types of platen assemblies.

FIGS. 57-60 show a saddle-shaped opposable 1730 that is convex in a first direction and convex in a second. The illustrated opposable 1730 has a surface 1738 that is concave in one direction (e.g., concave as viewed along an axis of concavity 1732 of FIG. 57), and convex in another direction (e.g., convex as viewed along an axis of convexity 1734 of FIG. 57).

Figure 58:
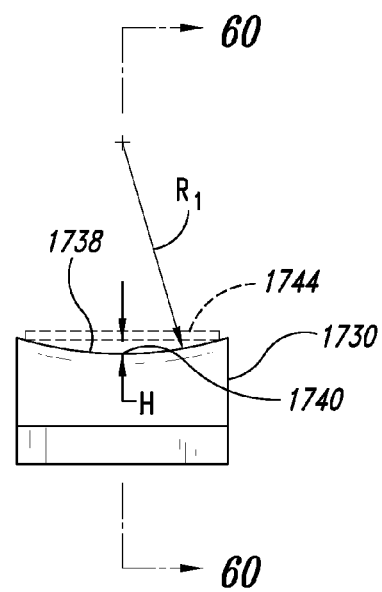
FIG. 58 is a front view of the opposable of FIG. 57.
Figure 59:
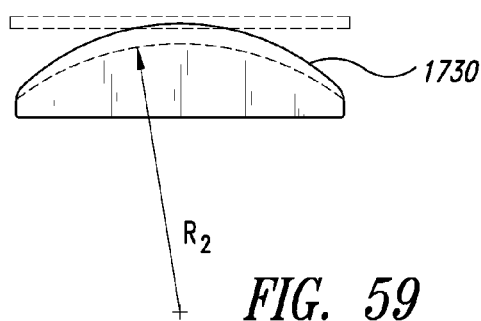
FIG. 59 is a side elevational view of the opposable of FIG. 57.

The curvature (e.g., a radius of curvature $R_1$ can be increased or decreased to decrease or increase a height H of a gap between a central region 1740 of the surface 1738 and a slide 1744 (shown in phantom line in FIGS. 58 and 59). The curvature $R_1$ can also vary along a length of the opposable 1730. The radius of curvature $R_2$ can be selected based on the desired rolling action. The opposable 1730 can be used with the embodiments disclosed herein. For example, the opposable 1730 can be used as the substrate 140 of FIGS. 16-18, the cover 1268 of FIG. 35, cover 1446 of FIG. 48, or cover 1594 of FIG. 51. The opposable 1730 may be compliant, semi-compliant, or rigid.

Figure 60:
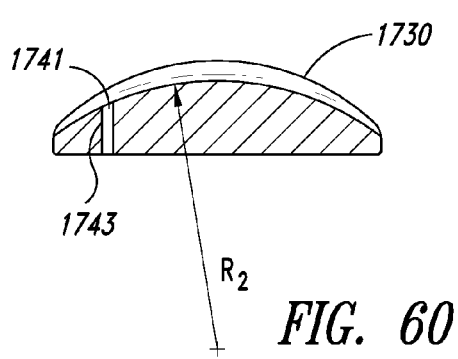
FIG. 60 is a cross-sectional view of the opposable of FIG. 58 taken along a line 60-60.

Referring to FIG. 60, a vacuum can be drawn through a waste port 1741 and a passage 1743 to remove substances. Any number of waste ports and passages can be positioned along the opposable 1730.

Figure 61:
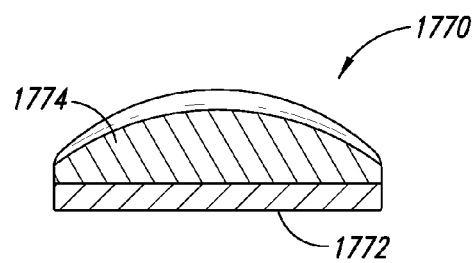
FIG. 61 is a longitudinal cross-sectional view of an opposable, in accordance with one embodiment.

FIG. 61 shows a saddle-shaped opposable 1770 that includes a base 1772 and a cover 1774. The cover 1774 can be disposable or reusable. In disposable embodiments, the cover 1774 can be made of a highly compliant material. In reusable embodiments, the cover 1774 can be made of a rigid material capable of withstanding repeated contact with slides. In yet other embodiments, the cover 1774 can have one section made of a compliant material and another section made of a rigid material.

The embodiments disclosed herein can perform a wide range of different types of processing, including flat mode processing, curved mode processing, or combinations thereof. In flat mode processing, a substrate can be in a generally flat configuration. The substrate can be held by a component (for example, a holder) and may or may not float on the applied fluid. U.S. Patent Application No. 61/222,046, filed Jun. 30, 2009, which is incorporated by reference in its entirety, discloses apparatuses, methods, and components suitable for floating a substrate on a liquid. In some embodiments, a substrate can be in a curved configuration and used to spread a fluid along a slide. The substrate can then be moved to a generally flat configuration and allowed to float on the fluid. In certain embodiments, the substrate is separated from a holder to allow the substrate to float. In other embodiments, a holder continuously holds the substrate as the substrate floats.

The embodiments, features, systems, devices, materials, methods and techniques described herein may, in some embodiments, be similar to any one or more of the embodiments, features, systems, devices, materials, methods and techniques described in U.S. patent application Ser. No. 11/187,183 (Publication No. 2006/0019302) and U.S. Patent Application No. 61/222,046, which are incorporated by reference in their entireties. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned U.S. patent application Ser. No. 11/187,183.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of processing a sample, comprising:
   delivering a first slide carrying a first sample to a slide positioning device of an automated slide processing station;
   delivering a first liquid to at least one of the first slide and a curved portion of a roller unit of the automated slide processing station; and
   rolling the curved portion of the roller unit relative to the first slide held by the slide positioning device to apply the first liquid to the first sample on the first slide while the first liquid is located in a varying height gap defined by the first slide and the curved portion.

2. The method of claim 1, further comprising:
   delivering a second liquid to at least one of the first slide and the curved portion of the roller unit after applying the first liquid to the first sample; and
   applying the second liquid to the first sample by moving the curved portion relative to the first slide to move the second liquid along the varying height gap.

3. The method of claim 1, further comprising:
   moving the first liquid towards a waste port of the roller unit by moving the curved portion relative to the first slide; and
   removing the first liquid from the varying height gap using the waste port while at least a portion of the first slide extends across the waste port.

4. The method of claim 1, further comprising rolling the curved portion along the first slide using a gapping element of the curved portion.

5. The method of claim 1, further comprising:
   removing the first liquid from between the first slide and the curved portion;
   removing a cover from a holder of the roller unit, the cover defining the curved portion; and
   placing another cover on the holder of the roller unit before processing a second sample on a second slide.

6. The method of claim 1, further comprising:
   delivering a second slide carrying a second sample to the slide positioning device after removing the first slide from the slide positioning device; and
   applying a second liquid to the second specimen on the second slide using a surface of the curved portion that contacted the first liquid.

7. The method of claim 1, further comprising:
   dispensing a second liquid onto at least one of the curved portion and the first slide after dispensing the first liquid; and
   mixing the first liquid and the second liquid using longitudinal or lateral movement of the curved portion relative to the first slide.

8. The method of claim 1, wherein delivering the first liquid comprises dispensing less than about 200 microliters of the first liquid.

9. The method of claim 1, wherein delivering the first liquid comprises dispensing about 50 microliters to about 120 microliters of the first liquid into the varying height gap.

10. The method of claim 1, further comprising:
    delivering a second liquid onto at least one of the curved portion and the first slide after delivering the first liquid; and
    mixing the first liquid and the second liquid using longitudinal or lateral movement of the curved portion relative to the first slide.

11. The method of claim 1, further comprising:
    mixing a first substance and a second substance to produce the first liquid; and
    outputting the first liquid from a liquid dispensing assembly to deliver the first liquid to at least one of the first slide and the curved portion.

12. The method of claim 1, further comprising:
    heating the first liquid using at least one of the slide positioning device and the roller unit.

13. The method of claim 1, further comprising adjusting a profile of the varying height gap by rolling the curved portion relatively to the first slide to move the first liquid along the varying height gap.

14. The method of claim 1, further comprising:
    rolling the curved portion away from the first slide such that the first liquid is delivered between the first slide and a section of the curved portion that has been rolled away from the first slide.

15. The method of claim 1, wherein rolling the curved portion of the roller unit relative to the first slide includes rolling the curved portion in a direction generally parallel to a longitudinal axis of the first slide.

16. The method of claim 1, further comprising heating the slide positioning device or the curved portion of the roller unit to heat the first sample.

17. The method of claim 1, wherein the curved portion of the roller unit is a cover with one or more gapping elements dimensioned to define the varying height gap between the first slide and the cover.

18. A method of processing a sample, comprising:
    delivering a first microscope slide carrying a first sample to an automated slide processing station, wherein the automated slide processing station includes at least one thermal element configured to receive electrical energy and to generate heat for heating the first microscope slide;

delivering a first liquid to the first microscope slide and/or a cover of a roller unit of the automated slide processing station; and rolling the cover of the roller unit along the first microscope slide to move the first liquid across the first sample while the first liquid is located in a varying height gap and while one or more of a plurality of discrete gapping elements of the cover contact the first microscope slide.

19. The method of claim 18, wherein the plurality of discrete gapping elements are positioned outside of a liquid application region and spaced apart from one another along a length of the liquid application region, wherein the plurality of discrete gapping elements are dimensioned to space the first microscope slide from the liquid application region to create the varying height gap.

20. The method of claim 18, further comprising:

removing the first liquid from between the first microscope slide and the cover;

removing the cover from a holder of the roller unit; and placing a second cover in the holder of the roller unit before processing a second sample on a second microscope slide using the second cover.

21. The method of claim 18, wherein rolling the cover of the roller unit along the first microscope slide includes rolling the cover back and forth across the first sample.

22. The method of claim 18, further comprising holding the first microscope slide using a vacuum chuck of the automated slide processing station while rolling the cover of the roller unit along the first microscope slide.

* * * * *